(12) United States Patent
Liu et al.

(10) Patent No.: US 10,800,776 B2
(45) Date of Patent: Oct. 13, 2020

(54) FLUORINE-CONTAINING TRIAZOLOPYRIDINE, AND MANUFACTURING METHOD, PHARMACEUTICAL COMPOSITION, AND APPLICATION THEREOF

(71) Applicant: SHANGHAI INSTITUTE OF MATERIA MEDICA, CHINESE ACADEMY OF SCIENCES, Shanghai (CN)

(72) Inventors: Hong Liu, Shanghai (CN); Yu Zhou, Shanghai (CN); Wenjing Xia, Shanghai (CN); Dong Zhang, Shanghai (CN); Hualiang Jiang, Shanghai (CN); Kaixian Chen, Shanghai (CN)

(73) Assignee: Shanghai Institute of Materia Medica, Chinese Academy of Sciences, Shanghai (CN)

( * ) Notice: Subject to any disclaimer, the term of this patent is extended or adjusted under 35 U.S.C. 154(b) by 0 days.

(21) Appl. No.: 16/302,154

(22) PCT Filed: May 17, 2017

(86) PCT No.: PCT/CN2017/084750
§ 371 (c)(1),
(2) Date: Mar. 22, 2019

(87) PCT Pub. No.: WO2017/198180
PCT Pub. Date: Nov. 23, 2017

(65) Prior Publication Data
US 2019/0202827 A1 Jul. 4, 2019

(30) Foreign Application Priority Data
May 17, 2016 (CN) .......................... 2016 1 0327058

(51) Int. Cl.
| | | |
|---|---|---|
| A61K 31/4196 | (2006.01) |
| A61K 31/437 | (2006.01) |
| C07D 471/04 | (2006.01) |
| A61P 25/18 | (2006.01) |
| A61P 25/28 | (2006.01) |
| A61K 31/5377 | (2006.01) |
| A61K 31/4545 | (2006.01) |
| A61K 31/506 | (2006.01) |
| A61K 31/4709 | (2006.01) |
| A61K 31/496 | (2006.01) |
| A61P 25/22 | (2006.01) |
| A61P 25/24 | (2006.01) |

(52) U.S. Cl.
CPC .......... *C07D 471/04* (2013.01); *A61K 31/437* (2013.01); *A61K 31/4545* (2013.01); *A61K 31/4709* (2013.01); *A61K 31/496* (2013.01); *A61K 31/506* (2013.01); *A61K 31/5377* (2013.01); *A61P 25/22* (2018.01); *A61P 25/24* (2018.01)

(58) Field of Classification Search
CPC .............. A61K 31/4196; A61K 31/437; C07D 471/04; A61P 25/18; A61P 25/28
See application file for complete search history.

(56) References Cited

U.S. PATENT DOCUMENTS 9,670,208 B2 * 6/2017 Blake .................. C07D 487/04

FOREIGN PATENT DOCUMENTS

| | | |
|---|---|---|
| CN | 102439009 A | 5/2012 |
| CN | 103298809 A | 9/2013 |
| WO | 2012062752 A1 | 5/2012 |

OTHER PUBLICATIONS

Int'l Search Report dated Aug. 23, 2017 in Int'l Application No. PCT/CN2017/084750.

* cited by examiner

*Primary Examiner* — Brenda L Coleman
(74) *Attorney, Agent, or Firm* — Panitch Schwarze Belisario & Nadel LLP

(57) ABSTRACT

A fluorine-containing triazolopyridine represented by formula (I) and a racemate, R-stereoisomer, S-stereoisomer, pharmaceutically acceptable salt, or mixture thereof are described. The triazolopyridine can be used as a positive allosteric modulator of an mGluR2, and is highly selective in activating the mGluR2, exerting no activation or very limited activation of other homologous metabotropic glutamate receptor. The triazolopyridine can thus be used to prepare a product for treating an mGluR2-related disease, such as a central nervous system disease or neurological disease.

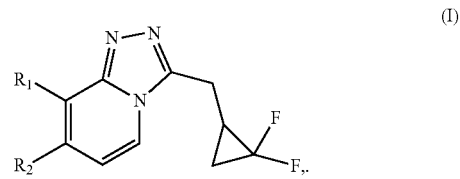

(I)

9 Claims, No Drawings

FLUORINE-CONTAINING TRIAZOLOPYRIDINE, AND MANUFACTURING METHOD, PHARMACEUTICAL COMPOSITION, AND APPLICATION THEREOF

CROSS-REFERENCE TO RELATED APPLICATION

This application is a Section 371 of International Application No. PCT/CN2017/084750, filed May 17, 2017, which was published in the Chinese language on Nov. 23, 2017, under International Publication No. WO 2017/198180 A1, which claims priority under 35 U.S.C. § 119(b) to Chinese Application No. 201610327058.6, filed May 17, 2016, the disclosures of which are incorporated herein by reference in their entirety.

FIELD OF THE INVENTION

The present invention relates to the field of pharmaceutical chemistry and pharmaceutical therapeutics, and more particularly to a class of fluorine-containing triazolopyridine, the preparation thereof, a pharmaceutical composition containing such a compound, and the use in as a positive allosteric modulator of second type metabotropic glutamate (MGluR2), in particular in preparation of medicines for the treatment of diseases such as central nervous system and psychiatric-related diseases such as schizophrenia, anxiety, depression, AD (Alzheimer disease), pain, epilepsy or drug addiction.

BACKGROUND OF THE INVENTION

Glutamate is the most important excitatory neurotransmitter in the central nervous system of mammals which plays an important role in the maintenance of the normal function of the nervous system, and plays an important role in the learning, memory, sensory perception, synaptic plasticity, regulation of cardiovascular function, and regulation of various physiological functions. Glutamate acts by activating its receptor. The massive release and accumulation thereof in the nervous system cause a variety of nerve damage and neurodegeneration, and these neurotoxic effects are key factors in causing many neurological and psychiatric diseases such as schizophrenia, anxiety, depression and the like. Therefore, glutamate receptors have become one of the important targets for the treatment of these diseases.

Glutamate receptors (GluRs) are mainly divided into ionotropic glutamate receptors (iGluRs) and metabotropic glutamate receptors (mGluRs). The ionotropic glutamate receptor includes fourteen subtypes such as aspartate receptor (NMDAR), aminomethyl phosphate receptor (AMDAR), and kainate receptor (KAR). Such receptors couple to ion channels to form receptor-channel complexes so as to mediate rapid excitatory synaptic transmission processes. The ionotropic receptor antagonist has achieved some therapeutic effect in the animal model by directly blocking the postsynaptic effect of glutamate, but it also blocks normal excitatory transmission and produces serious side effects, such as psychiatric symptoms, dizziness, fatigue, etc., thus limiting the clinical application of such compounds. Meanwhile, metabotropic glutamate receptor which mainly located in the presynaptic membrane inhibits the release of glutamate through the presynaptic mechanism, thus reducing the toxic and side effect of ionotropic glutamate receptor antagonist, which is expected to become a new target for the treatment of certain neurological diseases.

mGluRs is one member of the G protein coupled receptor (GPCRs) superfamily. In addition to seven characteristic transmembrane regions, the sequence of mGluRs has no homology with other G-protein coupled receptors, thus constituting a new family of G-protein coupled receptors. According to its amino acid sequence homology, receptor-coupled second messenger signal transduction mechanism and specificity for different agonists, it can also be divided into eight subtypes, which are classified into three groups. Among them, mGluR1 and mGluR5 belong to the first group (mGluRI), which mainly distribute in the postsynaptic, and activate phospholipase C (PLC) to make the phosphoinositide (PI) in the membrane hydrolyzed into intracellular second messenger diglyceride (DAG) and inositol 1,4,5-triphosphate (IP3), resulting in an increase in intracellular Ca2+ concentration. mGluR2 and mGluR3 belong to the second group (mGluRII), which mainly distribute in pre-synaptic, are activated after coupling with Gi/o, and inhibit the formation of cyclic adenosine and voltage-sensitive Ca2+ channels so as to activate K+ channels. mGluR4, mGluR6, mGluR7 and mGluR8 belong to the third group (mGluR III), also mainly distribute in presynaptic, and couple with Gi/o to inhibit adenylate cyclase activity after activation in order to reduce cAMP; or enhance activation of adenylate cyclase by Gs protein-coupled receptors to increase cAMP production. mGluR also stimulates the formulation of cGMP, activates phosphatase D and stimulates the release of arachidonic acid.

mGluR2 is abundantly expressed in presynaptic axons in the cortex, hippocampus, striatum, and amygdala of the brain, negatively regulating the release of Glu and GABA, and mediating the transduction of excitatory signals. Studies have shown that Glu hyperfunction is associated with diseases such as schizophrenia, anxiety, and depression. Therefore, it is of great significance to design and synthesis mGluR2 small molecule agonists or positive allosteric modulators (PAMs), and to treat such diseases by activating mGluR2 thus reducing the release of Glu.

The first generation of small molecule agonists acting on mGluR2 is an analog of Glu, which acts mainly on the extracellular N-terminal homologous capture domain (VFD), which lacks selectivity and simultaneously activates mGluR2 and mGluR3. It is called mGluR2/3 mixed agonist. The BBB permeability of such compounds is poor, and long-term use may desensitize the receptor, thus limiting its further development. The mGluR2 PAMs act on the seven transmembrane regions with low homology, which not only improves selectivity and reduces potential tolerance and the risk of receptor desensitization, but also has a variety of chemical structures and good BBB permeability as well as high drug-likeness. In addition, mGluR2 PAMs only play a role when a large amount of Glu is present, thus greatly improves the safety of drug use.

Since 2001, Eli Lilly has reported mGluR2 PAMs, and many pharmaceutical companies (such as Merck, Janssen, AstraZeneca) have also reported mGluR2 PAMs of different structural types. At present, there are two PAMs have entered clinical trials, which are AstraZeneca's AZD8529 and Janssen's JNJ-40411813. In January 2011, AstraZeneca discontinued clinical phase IIa studies of AZD8529 in patients with schizophrenia due to low activity. JNJ-40411813 meets the basic safety and tolerability requirements in the clinical phase IIa study of patients with schizophrenia (2011.3), and its clinical phase II trial as adjunctive therapy in patients with major depression with anxiety is also finished. In addition, the study found that negative symptoms in patients treated with antipsychotics can also be treated by using JNJ-40411813 as adjuvant therapy.

In summary, the design and development of novel mGluR2 positive allosteric modulators for the treatment of central nervous system and mental system related diseases is of great significance and good application prospects.

SUMMARY OF THE INVENTION

The object of the present invention is to provide novel mGluR2 positive allosteric modulator, in particular selectivity improved mGluR2 positive allosteric modulators.

In the first aspect of the invention, a fluorine-containing triazolopyridine represented by formula (I) and a racemate, R-stereoisomer, S-stereoisomer, pharmaceutically acceptable salt, or mixture thereof is provided:

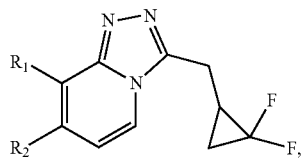

(I)

wherein:

$R_1$ is selected from the group consisting of a hydrogen, halogen, substituted or unsubstituted C1-C6 alkyl and cyano;

$R_2$ is select from the group consisting of a hydrogen, halogen, substituted or unsubstituted phenyl, substituted or unsubstituted heteroaryl, substituted or unsubstituted 3-7 membered heterocyclic group, substituted or unsubstituted 5-7 membered aryl-methylene and 3-7 membered heterocycle-methylene, while each of the heterocyclic groups independently contains 1 to 4 heteroatoms selected from oxygen, sulfur or nitrogen; and the "substituted" means one or more hydrogen atoms of the group are substituted by substituents selected from the group consisting of a halogen, C1-C6 alkyl, halogen-substituted C1-C6 alkyl, hydroxy-substituted C1-C6 alkyl, C1-C6 alkoxy, C1-C6 alkoxycarbonyl, halogen-substituted C1-C6 alkoxy, hydroxy-substituted C1-C6 alkoxy, cyano-substituted C1-C6 alkoxy, C2-C6 alkenyl, C2-C6 alkynyl, C3-C8 cycloalkyl, cyano, nitro, amino, hydroxy, hydroxymethyl, carboxy, mercapto, sulfonyl, C6-C10 aryl and 3-12 membered heterocyclic group; wherein the heterocyclic group each independently contain 1-4 heteroatoms selected from oxygen, sulfur or nitrogen;

The halogen is F, Cl, Br or I.

In another preferred embodiment, the $R_1$ is a halognated C1-C6 alkyl (e.g., trifluoromethyl).

In another preferred embodiment, the $R_2$ is selected from the group consisting of a hydrogen, halogen, substituted or unsubstituted phenyl, substituted or unsubstituted heteroaryl, substituted or unsubstituted 3-7 membered heterocyclic group, substituted or unsubstituted 5-7 membered aryl-methylene and 3-7 membered heterocyclyl-methylene, while each heterocyclic group independently contains 1-4 heteroatoms selected from oxygen, sulfur or nitrogen; wherein the substitute is defined as above;

In another preferred embodiment, the $R_1$ is selected from the group consisting of H, halogen, $CH_3$, CN and $CF_3$.

In another preferred embodiment, the $R_2$ is selected from the group consisting of a hydrogen, halogen, substituted or unsubstituted phenyl, substituted or unsubstituted heteroaryl, substituted or unsubstituted piperidinyl and substituted or unsubstituted piperazinyl; wherein the substitute is defined as above.

In another preferred embodiment, the $R_2$ is selected from the group consisting of:

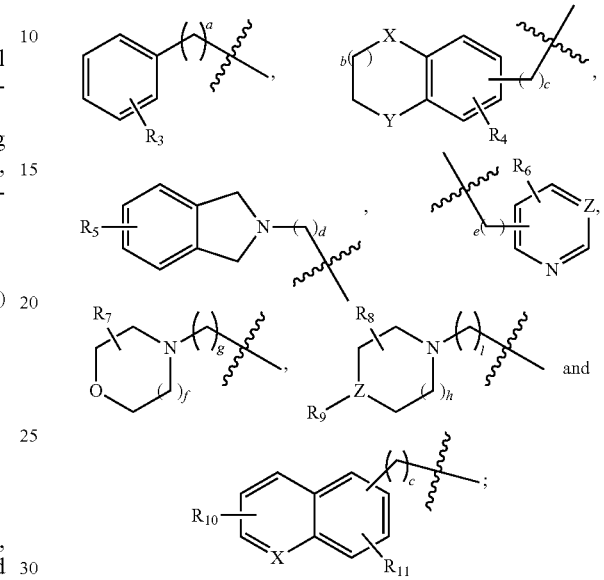

wherein the $R_3$, $R_4$, $R_5$, $R_6$, $R_7$ and $R_8$ each independently represents 0-4 substituents on any position of the ring, and each substituent is selected from the group consisting of a halogen, substituted or unsubstituted C1-C6 alkyl (preferably halogen-substituted C1-C6 alkyl, or hydroxy-substituted C1-C6 alkyl), substituted or unsubstituted C1-C6 alkoxy, C1-C6 alkoxycarbonyl, cyano and hydroxy; $R_9$ is selected from the group consisting of a hydrogen, halogen, substituted or unsubstituted C1-C6 alkyl, substituted or unsubstituted C2-C4 alkenyl, substituted or unsubstituted C2-C4 alkynyl, substituted or unsubstituted C3-C6 cycloalkyl, substituted or unsubstituted 3- to 9-membered heterocyclic group, substituted or unsubstituted aryl and substituted or unsubstituted heteroaryl; X, Y are each independently selected from C, O, N or S; Z is selected from C or N; a, b, c, d, e, f, g, h, and i are each independently selected from the group consisting of 0, 1 and 2.

In another preferred embodiment, the $R_2$ is

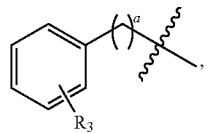

wherein $R_3$ represents 0-4 substituents (preferably 1-2 substituents) on any position of the ring, and each $R_3$ is independently selected from the group consisting of a halogen, substituted or unsubstituted C1-C6 alkyl (preferably halogen-substituted C1-C6 alkyl, or hydroxy-substituted C1-C6 alkyl), substituted or unsubstituted C1-C6 alkoxy, C1-C6 alkylcarbonyl, C1-C6 alkoxycarbonyl (preferably methoxycarbonyl), cyano and hydroxy; a is 0, 1 or 2.

In another preferred embodiment, the $R_2$ is

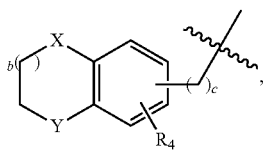

wherein $R_4$ represents 0-4 substituents (preferably 1-2 substituents) on any position of the ring, and each $R_4$ is independently selected from the group consisting of a halogen, substituted or unsubstituted C1-C6 alkyl (preferably halogen-substituted C1-C6 alkyl, or hydroxy-substituted C1-C6 alkyl), substituted or unsubstituted C1-C6 alkoxy, C1-C6 alkylcarbonyl, C1-C6 alkoxycarbonyl (preferably methoxycarbonyl), cyano and hydroxy; X, Y are each independently selected from C, O, N or S; b and c are independently selected from the group consisting of 0, 1 and 2.

In another preferred embodiment, the $R_2$ is

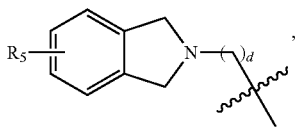

wherein $R_5$ represents 0-4 substituents (preferably 1-2 substituents) on any position of the ring, and each $R_5$ is independently selected from the group consisting of a halogen, substituted or unsubstituted C1-C6 alkyl (preferably halogen-substituted C1-C6 alkyl, or hydroxy-substituted C1-C6 alkyl), substituted or unsubstituted C1-C6 alkoxy, C1-C6 alkylcarbonyl, C1-C6 alkoxycarbonyl (preferably methoxycarbonyl), cyano and hydroxy; d is selected from the group consisting 0, 1 and 2.

In another preferred embodiment, the $R_2$ is

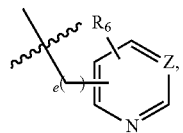

wherein $R_6$ represents 0-4 substituents (preferably 1-2 substituents) on any position of the ring, and each $R_6$ is independently selected from the group consisting of a halogen, substituted or unsubstituted C1-C6 alkyl (preferably halogen-substituted C1-C6 alkyl, or hydroxy-substituted C1-C6 alkyl), substituted or unsubstituted C1-C6 alkoxy, C1-C6 alkylcarbonyl, C1-C6 alkoxycarbonyl (preferably methoxycarbonyl), cyano and hydroxy; Z is selected from C or N; e is selected from the group consisting of 0, 1 and 2.

In another preferred embodiment, the $R_2$ is

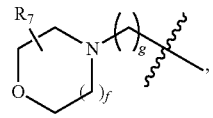

wherein $R_7$ represents 0-4 substituents (preferably 1-2 substituents) on any position of the ring, and each $R_7$ is independently selected from the group consisting of a halogen, substituted or unsubstituted C1-C6 alkyl (preferably halogen-substituted C1-C6 alkyl, or hydroxy-substituted C1-C6 alkyl), substituted or unsubstituted C1-C6 alkoxy, C1-C6 alkylcarbonyl, C1-C6 alkoxycarbonyl (preferably methoxycarbonyl), cyano and hydroxy; g and f are independently selected from the group consisting of 0, 1 and 2.

In another preferred embodiment, the $R_2$ is

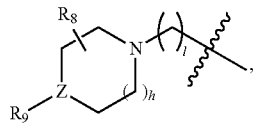

wherein $R_8$ represents 0-4 substituents (preferably 1-2 substituents) at any position on the ring, and each $R_8$ is independently selected from the group consisting of a halogen, substituted or unsubstituted C1-C6 alkyl (preferably halogen-substituted C1-C6 alkyl, or hydroxy-substituted C1-C6 alkyl), substituted or unsubstituted C1-C6 alkoxy, C1-C6 alkylcarbonyl, C1-C6 alkoxycarbonyl (preferably methoxycarbonyl), cyano and hydroxy; $R_9$ is selected from the group consisting of: a hydrogen, halogen, substituted or unsubstituted C1-C6 alkyl, substituted or unsubstituted C2-C4 alkenyl, substituted or unsubstituted C2-C4 alkynyl, substituted or unsubstituted C3-C6 cycloalkyl, substituted or unsubstituted 3- to 9-membered heterocyclic group, substituted or unsubstituted aryl and substituted or unsubstituted heteroaryl; Z is selected from C or N; h and i are independently selected from the group consisting of 0, 1 and 2.

In another preferred embodiment, the $R_2$ is

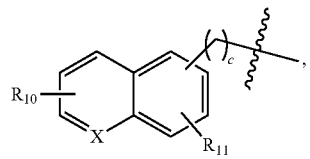

wherein $R_{10}$ and $R_{11}$ respectively represents 0-4 substituents (preferably 1-2 substituents) on any position of the ring, and each $R_{10}$ and $R_{11}$ is independently selected from the group consisting of a halogen, substituted or unsubstituted C1-C6 alkyl (preferably halogen-substituted C1-C6 alkyl, or hydroxy-substituted C1-C6 alkyl), substituted or unsubstituted C1-C6 alkoxy, C1-C6 alkylcarbonyl, C1-C6 alkoxycarbonyl (preferably methoxycarbonyl), cyano and hydroxy; X is C, O, N or S; c is 0, 1 or 2.

In another preferred embodiment, the compound of formula I is a compound selected from the table A.

TABLE A

| No. | Name | structure |
|---|---|---|
| 1 | 3-((2,2-difluorocyclopropyl)methyl)-7-(4-phenylpiperidin-1-yl)-[1,2,4]triazole[4,3-a]pyridine | 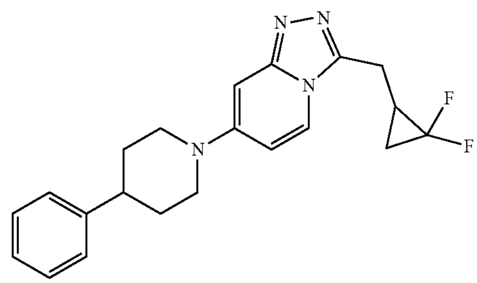 [SMILES: FC1(F)CC1Cc1nnc2cc(N3CCC(c4ccccc4)CC3)ccn12] |
| 2 | 3-((2,2-Difluorocyclopropyl)methyl)-7-(4-(4-fluorophenyl)piperidin-1-yl)-[1,2,4]triazole[4,3-a]pyridine | 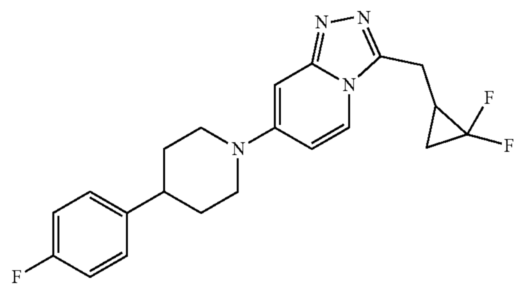 [SMILES: Fc1ccc(C2CCN(c3ccn4c(CC5CC5(F)F)nnc4c3)CC2)cc1] |
| 3 | 7-(4-(4-Chlorophenyl)piperidin-1-yl)-3-((2,2-difluorocyclopropyl)methyl)-[1,2,4]triazole[4,3-a]pyridine | 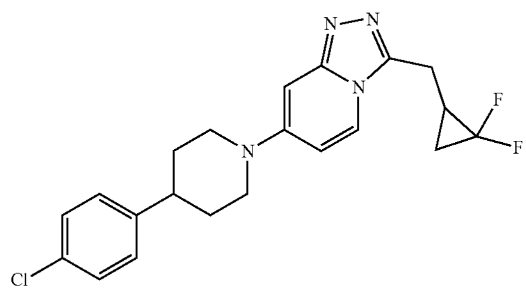 [SMILES: FC1(F)CC1Cc1nnc2cc(N3CCC(c4ccc(Cl)cc4)CC3)ccn12] |
| 4 | 7-(4-(3-Chlorophenyl)piperidin-1-yl)-3-((2,2-difluorocyclopropyl)methyl)-[1,2,4]triazole[4,3-a]pyridine | 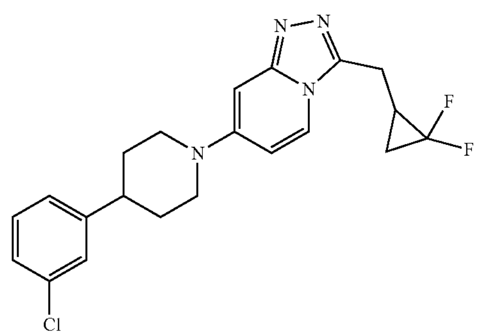 [SMILES: FC1(F)CC1Cc1nnc2cc(N3CCC(c4cccc(Cl)c4)CC3)ccn12] |
| 5 | 3-((2,2-Difluorocyclopropyl)methyl)-7-(4-(2-(trifluoromethyl)phenyl)piperidin-1-yl)-[1,2,4]triazole[4,3-a]pyridine | 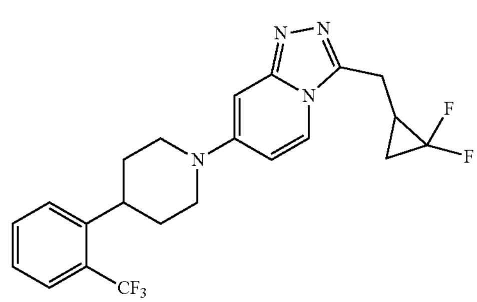 [SMILES: FC(F)(F)c1ccccc1C1CCN(c2ccn3c(CC4CC4(F)F)nnc3c2)CC1] |

TABLE A-continued

| No. | Name | structure |
|---|---|---|
| 6 | 1-(3-((2,2-difluorocyclopropyl)methyl)-[1,2,4]triazole[4,3-a]pyridin-7-yl)-4-phenylpiperidin-4-ol | 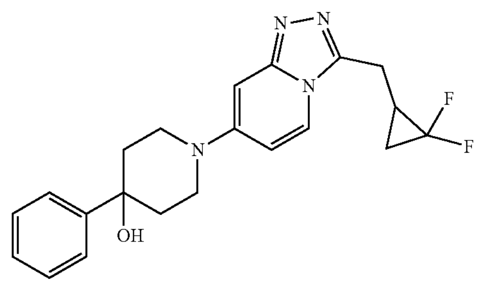 [SMILES: OC1(c2ccccc2)CCN(c2ccn3c(CC4CC4(F)F)nnc3c2)CC1] |
| 7 | 1-(3-((2,2-difluorocyclopropyl)methyl)-[1,2,4]triazole[4,3-a]pyridin-7-yl)-4-(4-fluorophenyl)piperidin-4-ol | 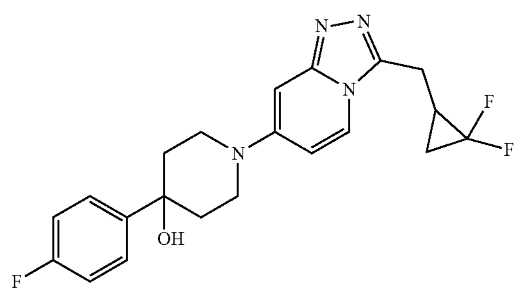 [SMILES: OC1(c2ccc(F)cc2)CCN(c2ccn3c(CC4CC4(F)F)nnc3c2)CC1] |
| 8 | 4-(4-Chlorophenyl)-1-(3-((2,2-difluorocyclopropyl)methyl)-[1,2,4]triazole[4,3-a]pyridine-7-yl)piperidin-4-ol | 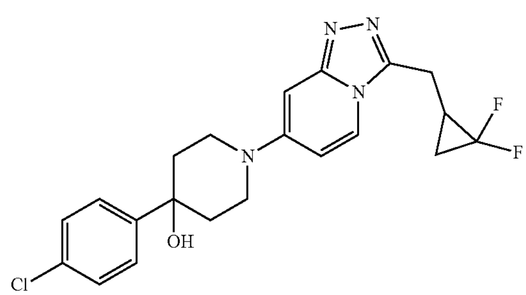 [SMILES: OC1(c2ccc(Cl)cc2)CCN(c2ccn3c(CC4CC4(F)F)nnc3c2)CC1] |
| 9 | 4-(4-chloro-3-(trifluoromethyl)phenyl)-1-(3-((2,2-difluorocyclopropyl)methyl)-[1,2,4]triazole[4,3-a]pyridin-7-yl)piperidin-4-ol | 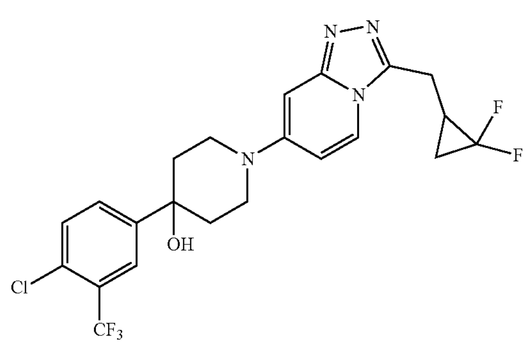 [SMILES: OC1(c2ccc(Cl)c(C(F)(F)F)c2)CCN(c2ccn3c(CC4CC4(F)F)nnc3c2)CC1] |
| 10 | 3-((2,2-difluorocyclopropyl)methyl)-7-(m-tolyl)-[1,2,4]triazole[4,3-a]pyridine | 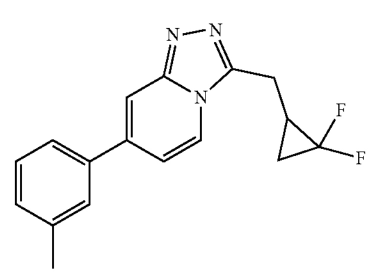 [SMILES: Cc1cccc(-c2ccn3c(CC4CC4(F)F)nnc3c2)c1] |

TABLE A-continued

| No. | Name | structure |
|---|---|---|
| 11 | 3-((2,2-Difluorocyclopropyl)methyl)-7-(3-fluorophenyl)-[1,2,4]triazole[4,3-a]pyridine | 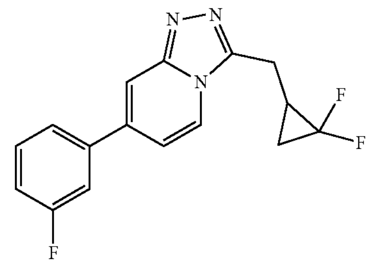 [SMILES: Fc1cccc(-c2ccn3c(CC4CC4(F)F)nnc3c2)c1] |
| 12 | 3-((2,2-Difluorocyclopropyl)methyl)-7-(3-(trifluoromethyl)phenyl)-[1,2,4]triazole[4,3-a]pyridine | 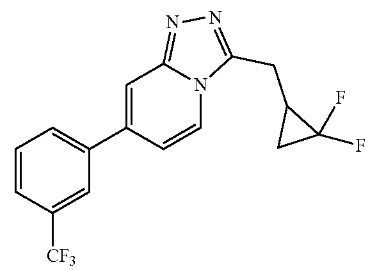 [SMILES: FC(F)(F)c1cccc(-c2ccn3c(CC4CC4(F)F)nnc3c2)c1] |
| 13 | 3-((2,2-difluorocyclopropyl)methyl)-7-(4-fluorophenyl)-[1,2,4]triazole[4,3-a]pyridine | 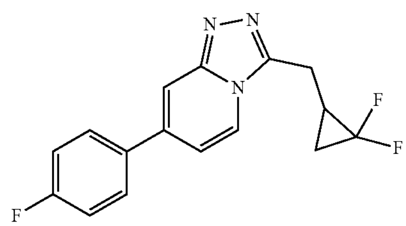 [SMILES: Fc1ccc(-c2ccn3c(CC4CC4(F)F)nnc3c2)cc1] |
| 14 | 3-((2,2-difluorocyclopropyl)methyl)-7-(4-(trifluoromethyl)phenyl)-[1,2,4]triazole[4,3-a]pyridine | 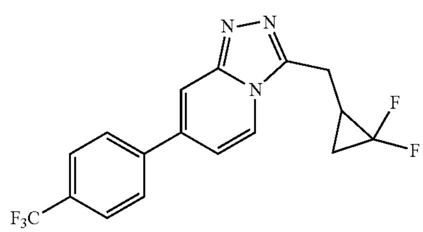 [SMILES: FC(F)(F)c1ccc(-c2ccn3c(CC4CC4(F)F)nnc3c2)cc1] |
| 15 | 4-(3-((2,2-difluorocyclopropyl)methyl)-[1,2,4]triazole[4,3-a]pyridin-7-yl)benzonitrile | 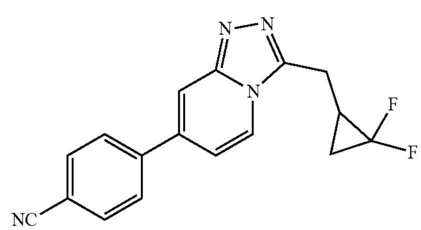 [SMILES: N#Cc1ccc(-c2ccn3c(CC4CC4(F)F)nnc3c2)cc1] |
| 16 | 1-(4-(3-((2,2-difluorocyclopropyl)methyl)-[1,2,4]triazole[4,3-a]pyridin-7-yl)phenyl)ethanone | 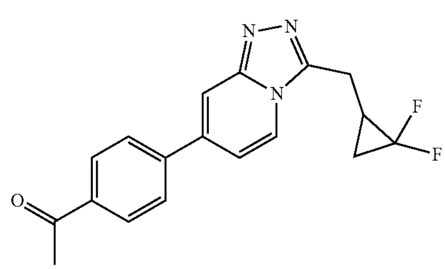 [SMILES: CC(=O)c1ccc(-c2ccn3c(CC4CC4(F)F)nnc3c2)cc1] |

TABLE A-continued

| No. | Name | structure |
|-----|------|-----------|
| 17 | methyl 4-(3-((2,2-difluorocyclopropyl)methyl)-[1,2,4]triazole[4,3-a]pyridin-7-yl)benzoate | 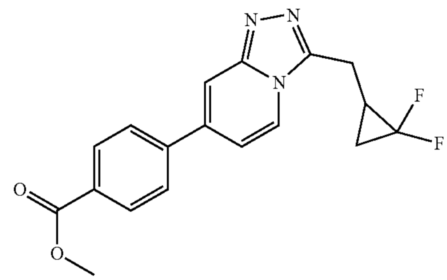 [SMILES: COC(=O)c1ccc(-c2ccn3c(CC4CC4(F)F)nnc3c2)cc1] |
| 18 | isopropyl 4-(3-((2,2-difluorocyclopropyl)methyl)-[1,2,4]triazole[4,3-a]pyridin-7-yl)benzonate | 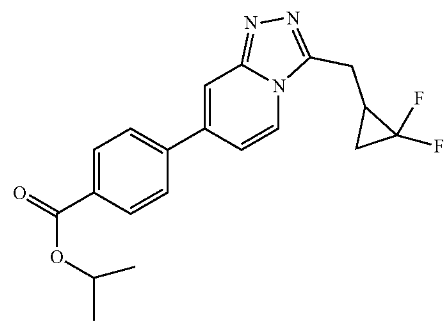 [SMILES: CC(C)OC(=O)c1ccc(-c2ccn3c(CC4CC4(F)F)nnc3c2)cc1] |
| 19 | 3-((2,2-Difluorocyclopropyl)methyl)-7-(4-methoxyphenyl)-[1,2,4]triazole[4,3-a]pyridine | 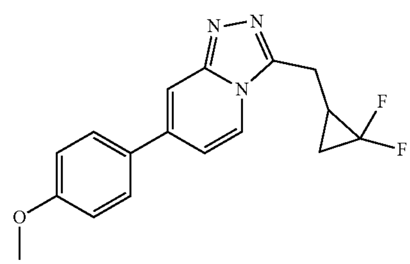 [SMILES: COc1ccc(-c2ccn3c(CC4CC4(F)F)nnc3c2)cc1] |
| 20 | (4-(3-((2,2-difluorocyclopropyl)methyl)-[1,2,4]triazole[4,3-a]pyridin-7-yl)phenyl)methanol | 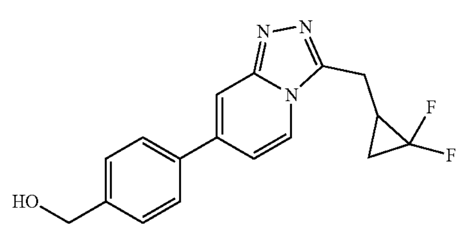 [SMILES: OCc1ccc(-c2ccn3c(CC4CC4(F)F)nnc3c2)cc1] |
| 21 | 2-(4-(3-((2,2-difluorocyclopropyl)methyl)-[1,2,4]triazole[4,3-a]pyridin-7-yl)phenyl)propan-2-ol | 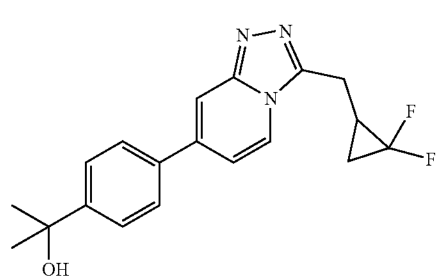 [SMILES: CC(C)(O)c1ccc(-c2ccn3c(CC4CC4(F)F)nnc3c2)cc1] |

TABLE A-continued

| No. | Name | structure |
|---|---|---|
| 22 | 3-((2,2-difluorocyclopropyl)methyl)-7-(3,4-dimethylphenyl)-[1,2,4]triazole[4,3-a]pyridine | 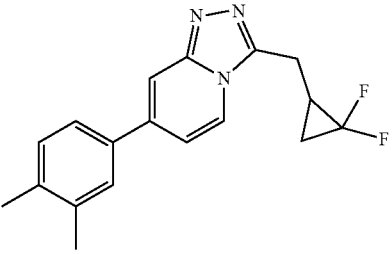 [SMILES: Cc1ccc(-c2ccn3c(CC4CC4(F)F)nnc3c2)cc1C] |
| 23 | 3-((2,2-difluorocyclopropyl)methyl)-7-(3-fluoro-4-methoxyphenyl)-[1,2,4]triazole[4,3-a]pyridine | 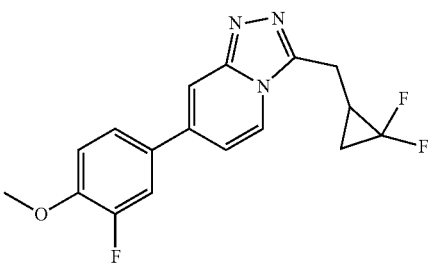 [SMILES: COc1ccc(-c2ccn3c(CC4CC4(F)F)nnc3c2)cc1F] |
| 24 | 3-((2,2-difluorocyclopropyl)methyl)-7-(2-fluoro-4-methoxyphenyl)-[1,2,4]triazole[4,3-a]pyridine | 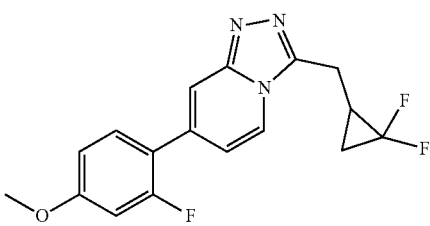 [SMILES: COc1ccc(-c2ccn3c(CC4CC4(F)F)nnc3c2)c(F)c1] |
| 25 | 3-((2,2-difluorocyclopropyl)methyl)-7-(4-fluoro-2-methoxyphenyl)-[1,2,4]triazole[4,3-a]pyridine | 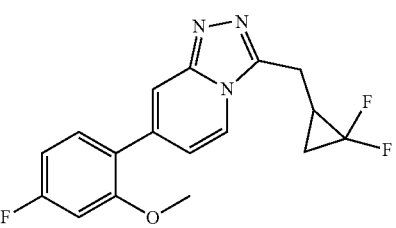 [SMILES: COc1cc(F)ccc1-c1ccn2c(CC3CC3(F)F)nnc2c1] |
| 26 | 3-((2,2-difluorocyclopropyl)methyl)-7-(4-fluoro-2-methylphenyl)-[1,2,4]triazole[4,3-a]pyridine | 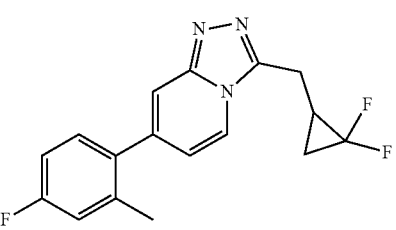 [SMILES: Cc1cc(F)ccc1-c1ccn2c(CC3CC3(F)F)nnc2c1] |
| 27 | 3-((2,2-difluorocyclopropyl)methyl)-7-(4-fluoro-3-methylphenyl)-[1,2,4]triazole[4,3-a]pyridine | 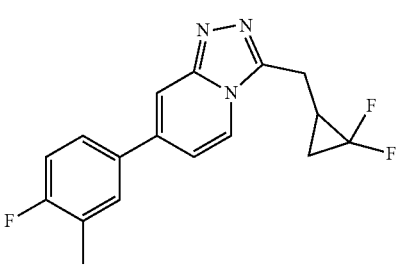 [SMILES: Cc1cc(-c2ccn3c(CC4CC4(F)F)nnc3c2)ccc1F] |

TABLE A-continued

| No. | Name |
|---|---|
| 28 | 7-(2-Chloro-4-fluorophenyl)-3-((2,2-difluorocyclopropyl)methyl)-[1,2,4]triazole[4,3-a]pyridine |
| 29 | Methyl 4-(3-((2,2-difluorocyclopropyl)methyl)-[1,2,4]triazolo[4,3-a]pyridin-7-yl)-3-fluorobenzonate |
| 30 | Methyl 3-Chloro-4-(3-((2,2-difluorocyclopropyl)methyl)-[1,2,4]triazole[4,3-a]pyridin-7-yl)benzonate |
| 31 | 3-((2,2-difluorocyclopropyl)methyl)-7-(2,3-benzodihydrofuran-5-yl)-[1,2,4]triazole[4,3-a]pyridine |
| 32 | 3-((2,2-difluorocyclopropyl)methyl)-7-(2,3-benzodihydrofuran-7-yl)-[1,2,4]triazole[4,3-a]pyridine |
| 33 | 6-(3-((2,2-difluorocyclopropyl)methyl)-[1,2,4]triazole[4,3-a]pyridin-7-yl)quinoline |

TABLE A-continued

| No. | Name | structure |
|---|---|---|
| 34 | 8-(3-((2,2-difluorocyclopropyl)methyl)-[1,2,4]triazole[4,3-a]pyridin-7-yl)quinoline | 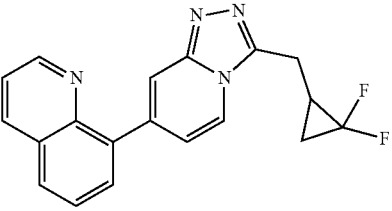 [SMILES: FC1(F)CC1Cc1nnc2cc(-c3cccc4cccnc34)ccn12] |
| 35 | 7-(Benzo[d][1,3]dioxol-5-yl)-3-((2,2-difluorocyclopropyl)methyl)-[1,2,4]triazole[4,3-a]pyridine | 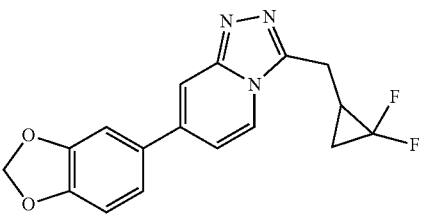 [SMILES: FC1(F)CC1Cc1nnc2cc(-c3ccc4c(c3)OCO4)ccn12] |
| 36 | 8-chloro-3-((2,2-difluorocyclopropyl)methyl)-7-(m-tolyl)-[1,2,4]triazole[4,3-a]pyridine | 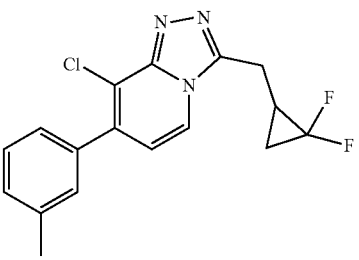 [SMILES: Cc1cccc(-c2ccn3c(CC4CC4(F)F)nnc3c2Cl)c1] |
| 37 | 8-chloro-3-((2,2-difluorocyclopropyl)methyl)-7-(3-fluorophenyl)-[1,2,4]triazole[4,3-a]pyridine | 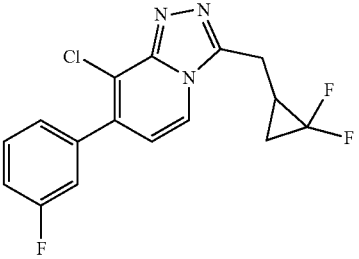 [SMILES: Fc1cccc(-c2ccn3c(CC4CC4(F)F)nnc3c2Cl)c1] |
| 38 | 8-chloro-3-((2,2-difluorocyclopropyl)methyl)-7-(4-fluorophenyl)-[1,2,4]triazole[4,3-a]pyridine | 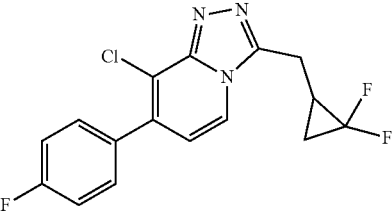 [SMILES: Fc1ccc(-c2ccn3c(CC4CC4(F)F)nnc3c2Cl)cc1] |
| 39 | 4-(8-chloro-3-((2,2-difluorocyclopropyl)methyl)-[1,2,4]triazole[4,3-a]pyridin-7-yl)cyanobenzene | 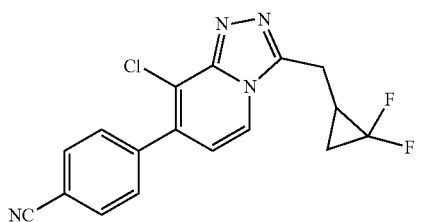 [SMILES: N#Cc1ccc(-c2ccn3c(CC4CC4(F)F)nnc3c2Cl)cc1] |

TABLE A-continued

| No. | Name | structure |
|---|---|---|
| 40 | 2-(4-(8-chloro-3-((2,2-difluorocyclopropyl)methyl)-[1,2,4]triazole[4,3-a]pyridine-7-yl)phenyl)isopropyl-2-ol | 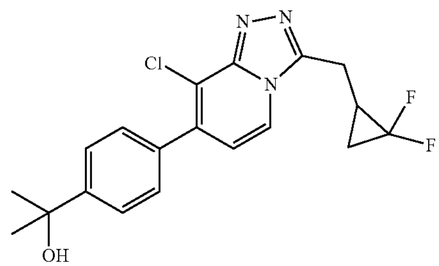 |
| 41 | 8-chloro-3-((2,2-difluorocyclopropyl)methyl)-7-(4-fluoro-2-methylphenyl)-[1,2,4]triazole[4,3-a]pyridine | 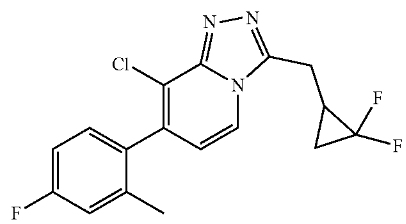 |
| 42 | 8-chloro-3-((2,2-difluorocyclopropyl)methyl)-7-(4-fluoro-3-methylphenyl)-[1,2,4]triazole[4,3-a]pyridine | 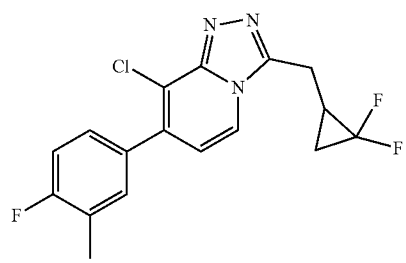 |
| 43 | 8-chloro-3-((2,2-difluorocyclopropyl)methyl)-7-(4-fluoro-2-methoxyphenyl)-[1,2,4]triazole[4,3-a]pyridine | 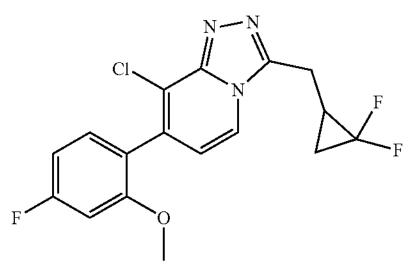 [SMILES: COc1cc(F)ccc1-c1ccn2c(CC3CC3(F)F)nnc2c1Cl] |
| 44 | 8-chloro-3-((2,2-difluorocyclopropyl)methyl)-7-(3-fluoro-4-methoxyphenyl)-[1,2,4]triazole[4,3-a]pyridine | 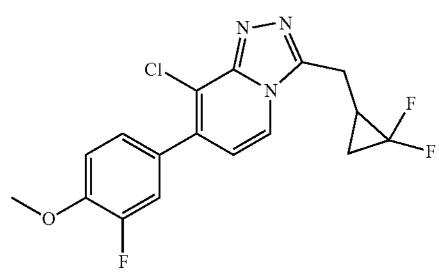 [SMILES: COc1ccc(-c2ccn3c(CC4CC4(F)F)nnc3c2Cl)cc1F] |
| 45 | Methyl 4-(8-Chloro-3-((2,2-difluorocyclopropyl)methyl)-[1,2,4]triazole[4,3-a]pyridin-7-yl)-3-fluorobenzoate | 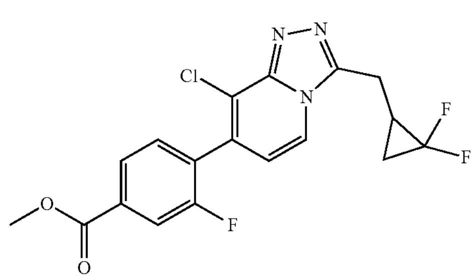 [SMILES: COC(=O)c1ccc(-c2ccn3c(CC4CC4(F)F)nnc3c2Cl)c(F)c1] |

TABLE A-continued

| No. | Name | structure |
|---|---|---|
| 46 | Methyl 3-Chloro-4-(8-chloro-3-((2,2-difluorocyclopropyl)methyl)-[1,2,4]triazole[4,3-a]pyridine-7-yl)benzoate | 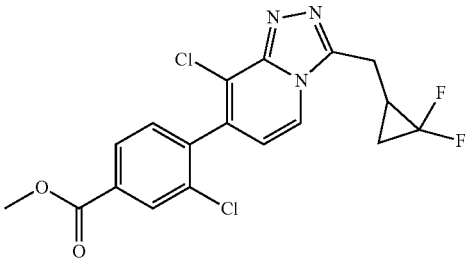 [SMILES: COC(=O)c1ccc(-c2ccn3c(CC4CC4(F)F)nnc3c2Cl)c(Cl)c1] |
| 47 | 8-chloro-3-((2,2-difluorocyclopropyl)methyl)-7-(2,3-benzodihydrofuran-5-yl)-[1,2,4]triazole[4,3-a]pyridine | 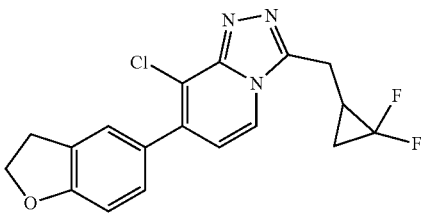 [SMILES: FC1(F)CC1Cc1nnc2c(Cl)c(-c3ccc4c(c3)CCO4)ccn12] |
| 48 | 8-chloro-3-((2,2-difluorocyclopropyl)methyl)-7-(2,3-benzodihydrofuran-7-yl)-[1,2,4]triazole[4,3-a]pyridine | 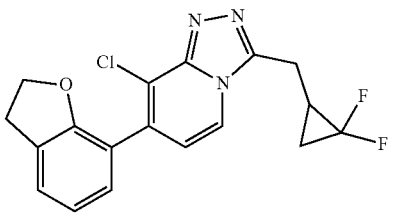 [SMILES: FC1(F)CC1Cc1nnc2c(Cl)c(-c3cccc4c3OCC4)ccn12] |
| 49 | 8-(8-chloro-3-((2,2-difluorocyclopropyl)methyl)-[1,2,4]triazole[4,3-a]pyridin-7-yl)quinoline | 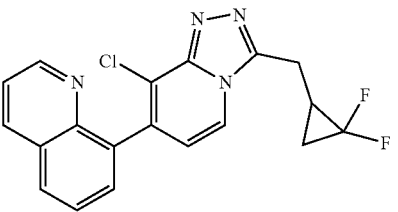 [SMILES: FC1(F)CC1Cc1nnc2c(Cl)c(-c3cccc4cccnc34)ccn12] |
| 50 | 7-(Benzo[d][1,3]dioxol-5-yl)-8-chloro-3-((2,2-difluorocyclopropyl)methyl)-[1, 2,4]triazole[4,3-a]pyridine | 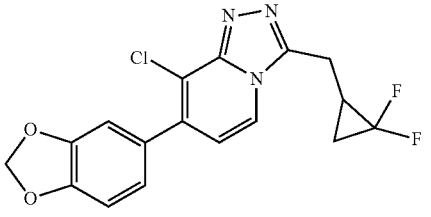 [SMILES: FC1(F)CC1Cc1nnc2c(Cl)c(-c3ccc4c(c3)OCO4)ccn12] |
| 51 | 3-((2,2-difluorocyclopropyl)methyl)-8-methyl-7-(m-tolyl)-[1,2,4]triazole[4,3-a]pyridine | 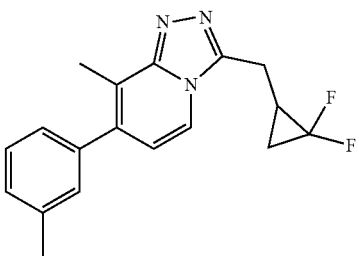 |

TABLE A-continued

| No. | Name | structure |
|---|---|---|
| 52 | 3-((2,2-difluorocyclopropyl)methyl)-8-methyl-7-(3-fluorophenyl)-[1,2,4]triazole[4,3-a]pyridine | 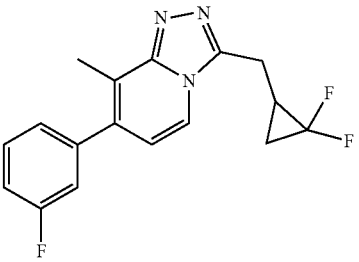 [SMILES: Cc1c(-c2cccc(F)c2)ccn2c(CC3CC3(F)F)nnc12] |
| 53 | 3-((2,2-difluorocyclopropyl)methyl)-8-methyl-7-(4-fluorophenyl)-[1,2,4]triazole[4,3-a]pyridine | 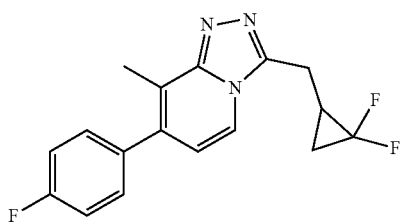 [SMILES: Cc1c(-c2ccc(F)cc2)ccn2c(CC3CC3(F)F)nnc12] |
| 54 | 2-(4-(3-((2,2-difluorocyclopropyl)methyl)-8-methyl-[1,2,4]triazole[4,3-a]pyridine-7-yl)phenyl)propan-2-ol | 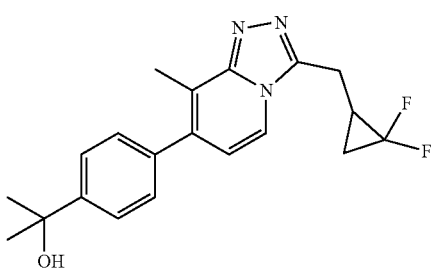 [SMILES: Cc1c(-c2ccc(C(C)(C)O)cc2)ccn2c(CC3CC3(F)F)nnc12] |
| 55 | 3-((2,2-difluorocyclopropyl)methyl)-7-(4-fluoro-2-methylphenyl)-8-methyl-[1,2,4]triazole[4,3-a]pyridine | 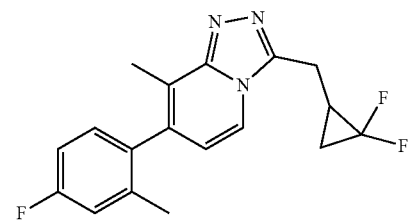 [SMILES: Cc1cc(F)ccc1-c1ccn2c(CC3CC3(F)F)nnc2c1C] |
| 56 | 3-((2,2-difluorocyclopropyl)methyl)-7-(4-fluoro-3-methylphenyl)-8-methyl-[1,2,4]triazole[4,3-a]pyridine | 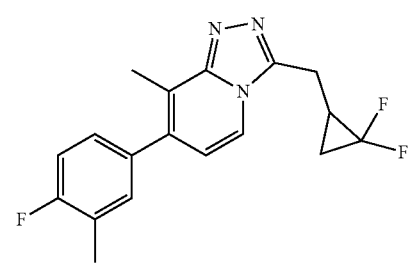 [SMILES: Cc1cc(-c2ccn3c(CC4CC4(F)F)nnc3c2C)ccc1F] |
| 57 | 3-((2,2-difluorocyclopropyl)methyl)-7-(3-fluoro-4-methoxyphenyl)-8-methyl-[1,2,4]triazole[4,3-a]pyridine | 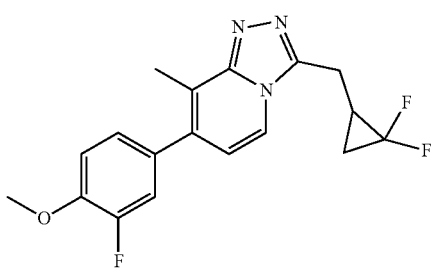 [SMILES: COc1ccc(-c2ccn3c(CC4CC4(F)F)nnc3c2C)cc1F] |

TABLE A-continued

| No. | Name | structure |
|---|---|---|
| 58 | Methyl 4-(3-((2,2-Difluorocyclopropyl)methyl)-8-methyl-[1,2,4]triazole[4,3-a]pyridin-7-yl)-3-fluorobenzoate | 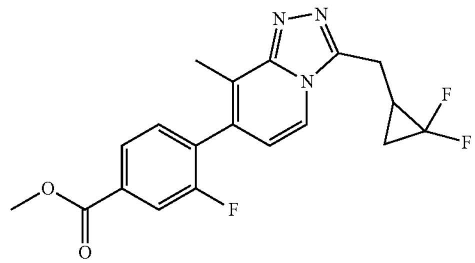 [SMILES: COC(=O)c1ccc(-c2ccn3c(CC4CC4(F)F)nnc3c2C)c(F)c1] |
| 59 | methyl 3-Chloro-4-(3-((2,2-difluorocyclopropyl)methyl))-8-methyl-[1,2,4]triazole[4,3-a]pyridin-7-yl)-benzonate | 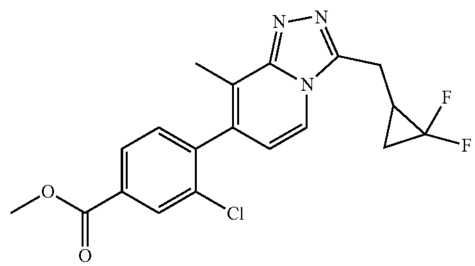 [SMILES: COC(=O)c1ccc(-c2ccn3c(CC4CC4(F)F)nnc3c2C)c(Cl)c1] |
| 60 | 3-((2,2-difluorocyclopropyl)methyl)-7-(2,3-benzodihydrofuran-5-yl)-8-methyl-[1,2,4]triazole[4,3-a]pyridine | 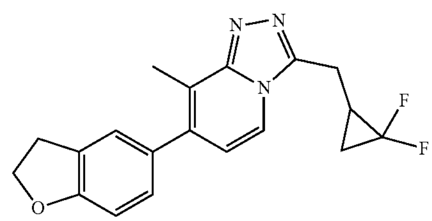 [SMILES: Cc1c(-c2ccc3c(c2)CCO3)ccn2c(CC3CC3(F)F)nnc12] |
| 61 | 7-(Benzo[d][1,3]dioxol-5-yl)-3-((2,2-difluorocyclopropyl)methyl)-8-methyl-[1,2,4]triazole[4,3-a]pyridine | 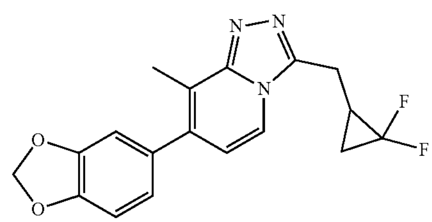 [SMILES: Cc1c(-c2ccc3c(c2)OCO3)ccn2c(CC3CC3(F)F)nnc12] |
| 62 | 3-((2,2-difluorocyclopropyl)methyl)-8-fluoro-7-(4-phenylpiperidin-1-yl)-[1,2,4]triazole[4,3-a]pyridine | 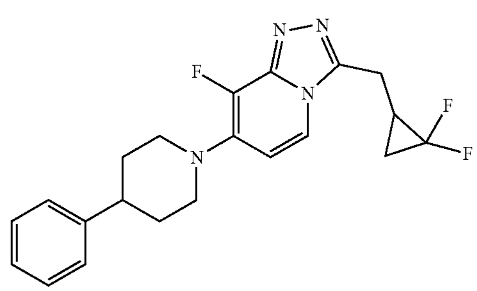 [SMILES: Fc1c(N2CCC(c3ccccc3)CC2)ccn2c(CC3CC3(F)F)nnc12] |
| 63 | 7-(4-(4-Chlorophenyl)piperidin-1-yl)-3-((2,2-difluorocyclopropyl)methyl)-8-fluoro-[1,2,4]triazole[4,3-a]pyridine | 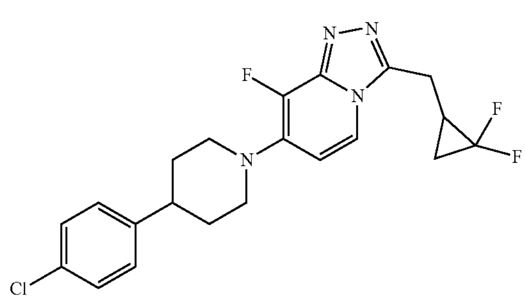 [SMILES: Fc1c(N2CCC(c3ccc(Cl)cc3)CC2)ccn2c(CC3CC3(F)F)nnc12] |

TABLE A-continued

| No. | Name | structure |
|-----|------|-----------|
| 64 | 4-(1-(3-((2,2-difluorocyclopropyl)methyl)-8-fluoro-[1,2,4]triazole[4,3-a]pyridin-7-yl)piperidin-4-yl)benzonitrile | 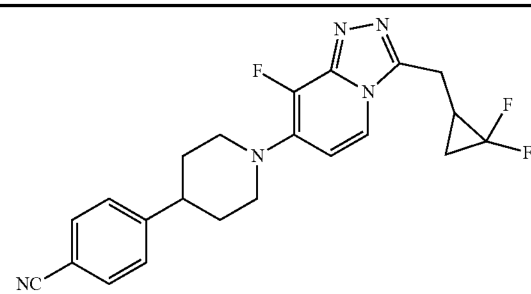 |
| 65 | 3-((2,2-difluorocyclopropyl)methyl)-8-fluoro-7-(4-(2-(trifluoromethyl)phenyl)piperidin-1-yl)-[1,2,4]triazole[4,3-a]pyridine | 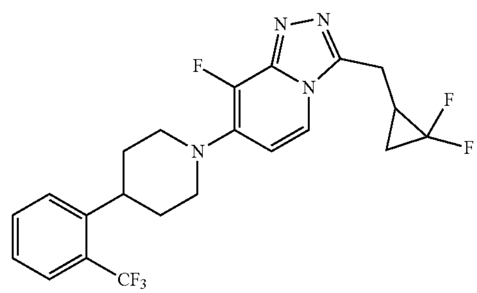 |
| 66 | 1-(3-((2,2-difluorocyclopropyl)methyl)-8-fluoro-[1,2,4]triazole[4,3-a]pyridin-7-yl)-4-phenylpiperidine-4-ol | 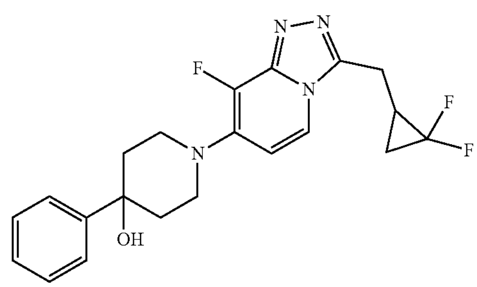 [SMILES: OC1(c2ccccc2)CCN(c2ccn3c(CC4CC4(F)F)nnc3c2F)CC1] |
| 67 | 3-((2,2-difluorocyclopropyl)methyl)-8-fluoro-7-(4-phenylpiperazin-1-yl)-[1,2,4]triazole[4,3-a]pyridine | 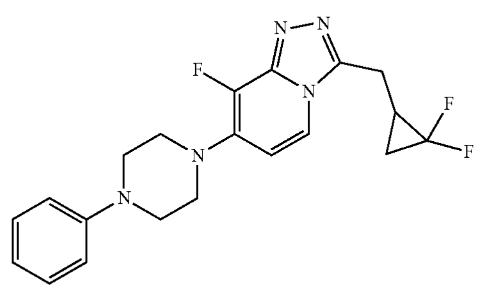 [SMILES: Fc1c(N2CCN(c3ccccc3)CC2)ccn2c(CC3CC3(F)F)nnc12] |
| 68 | 3-((2,2-difluorocyclopropyl)methyl)-8-fluoro-7-(m-tolyl)-[1,2,4]triazole[4,3-a]pyridine | 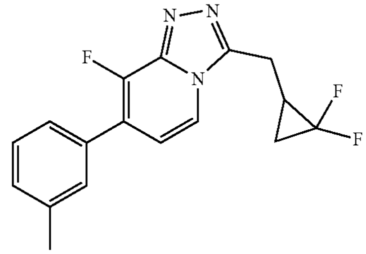 [SMILES: Cc1cccc(-c2ccn3c(CC4CC4(F)F)nnc3c2F)c1] |

TABLE A-continued

| No. | Name | structure |
| --- | --- | --- |
| 69 | 3-((2,2-difluorocyclopropyl)methyl)-8-fluoro-7-(4-(trifluoromethyl)phenyl)-[1,2,4]triazole[4,3-a]pyridine | 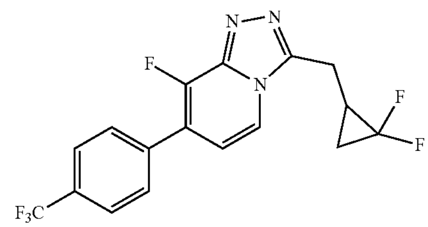 [SMILES: Fc1c(-c2ccc(C(F)(F)F)cc2)ccn2c(CC3CC3(F)F)nnc12] |
| 70 | 4-(3-((2,2-difluorocyclopropyl)methyl)-8-fluoro-[1,2,4]triazole[4,3-a]pyridin-7-yl)benzonitrile | 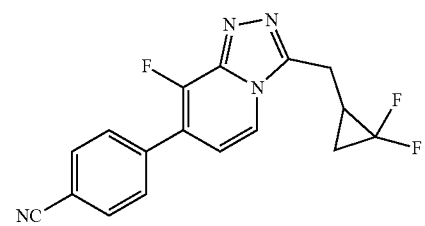 [SMILES: N#Cc1ccc(-c2ccn3c(CC4CC4(F)F)nnc3c2F)cc1] |
| 71 | 2-(4-(3-((2,2-difluorocyclopropyl)methyl)-8-fluoro-[1,2,4]triazole[4,3-a]pyridine-7-yl)phenyl)propan-2-ol | 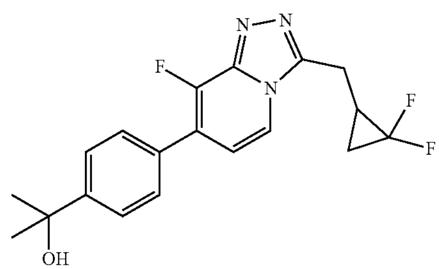 [SMILES: CC(C)(O)c1ccc(-c2ccn3c(CC4CC4(F)F)nnc3c2F)cc1] |
| 72 | 3-((2,2-difluorocyclopropyl)methyl)-8-fluoro-7-(4-fluoro-2-methylphenyl)-[1,2,4]triazole[4,3-a]pyridine | 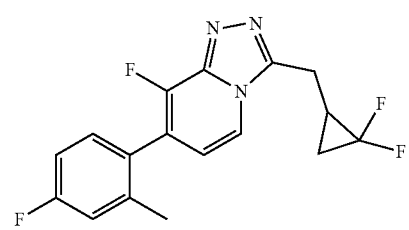 [SMILES: Cc1cc(F)ccc1-c1ccn2c(CC3CC3(F)F)nnc2c1F] |
| 73 | Methyl 4-(3-((2,2-difluorocyclopropyl)methyl)-8-fluoro)-8-fluoro-[1,2,4]triazole[4,3-a]pyridin-7-yl)-3-fluorobenzonate | 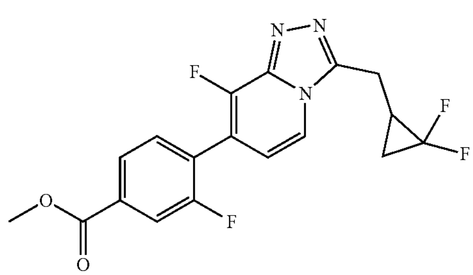 [SMILES: COC(=O)c1ccc(-c2ccn3c(CC4CC4(F)F)nnc3c2F)c(F)c1] |
| 74 | 3-((2,2-difluorocyclopropyl)methyl)-7-(2,3-benzodihydroruran-5-yl)-8-fluoro-[1,2,4]triazole[4,3-a]pyridine | 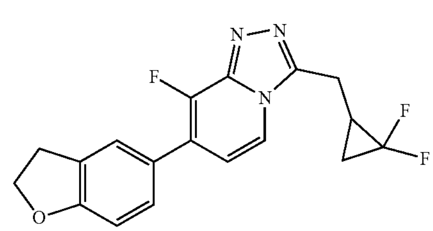 [SMILES: Fc1c(-c2ccc3c(c2)CCO3)ccn2c(CC3CC3(F)F)nnc12] |

TABLE A-continued

| No. | Name |
|---|---|
| 75 | 6-(3-((2,2-difluorocyclopropyl)methyl)-8-fluoro-[1,2,4]triazole[4,3-a]pyridine-7-yl)quinoline |
| 76 | 7-(Benzo[d][1,3]dioxole-5-yl)-3-((2,2-difluorocyclopropyl)methyl)-8-fluoro-[1,2,4]triazolo[4,3-a]pyridine |
| 77 | 8-bromo-3-((2,2-difluorocyclopropyl)methyl)-7-(4-(2-methylphenyl)piperidin-1-yl)-[1,2,4]triazolo[4,3-a]pyridine |
| 78 | 4-(1-(8-bromo-3-((2,2-difluorocyclopropyl)methyl))-[1,2,4]triazole[4,3-a]pyridine-7-yl)piperidin-4-yl)benzonitrile |
| 79 | 8-Bromo-3-((2,2-difluorocyclopropyl)methyl)-7-(4-(2-(trifluoromethylphenyl)piperidin-1-yl)-[1,2,4]triazolo[4,3-a]pyridine |
| 80 | 1-(8-Bromo-3-((2,2-difluorocyclopropyl)methyl)-[1,2,4]triazolo[4,3-a]pyridin-7-yl)-4-phenylpiperidin-4-ol |

TABLE A-continued

| No. | Name | structure |
|---|---|---|
| 81 | 8-bromo-7-(4-(2-chlorophenyl) piperazin-1-yl)-3-((2,2-difluorocyclopropyl) methyl)-[1,2,4]triazolo[4,3-a]pyridine | 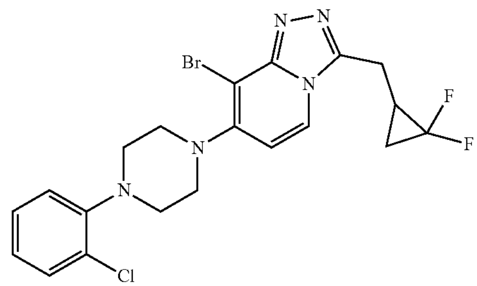 [SMILES: FC1(F)CC1Cc1nnc2c(Br)c(N3CCN(c4ccccc4Cl)CC3)ccn12] |
| 82 | 4-(8-Bromo-3-((2,2-difluorocyclopropyl) methyl)-[1,2,4]triazole[4,3-a] pyridine-7-benzonitrile | 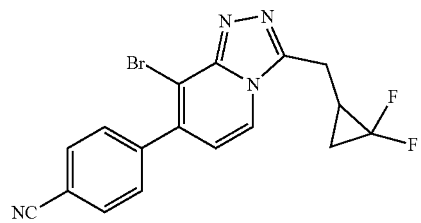 [SMILES: N#Cc1ccc(-c2ccn3c(CC4CC4(F)F)nnc3c2Br)cc1] |
| 83 | 8-Bromo-3-((2,2-difluorocyclopropyl)methyl)-7-(2-methyl-4-(trifluoromethyl)phenyl)-[1,2,4]triazole[4,3-a]pyridine | 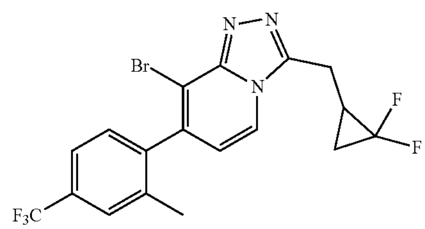 [SMILES: Cc1cc(C(F)(F)F)ccc1-c1ccn2c(CC3CC3(F)F)nnc2c1Br] |
| 84 | 2-(4-(8-bromo-3-((2,2-difluorocyclopropyl)methyl)-[1,2,4]triazole[4,3-a]pyridin-7-yl)-3-fluorophenyl)propan-2-ol | 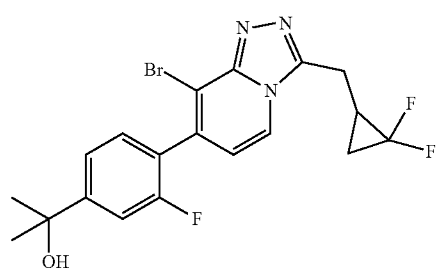 [SMILES: CC(C)(O)c1ccc(-c2ccn3c(CC4CC4(F)F)nnc3c2Br)c(F)c1] |
| 85 | Methyl 4-(8-Bromo-3-((2,2-difluorocyclopropyl) methyl)-[1,2,4]triazole[4,3-a] pyridine-7-yl)-3-chlorobenzoate | 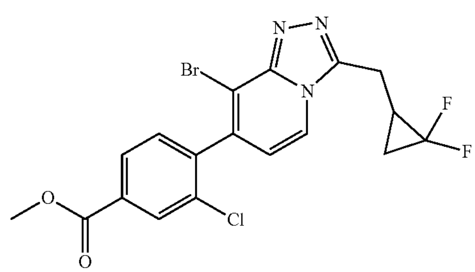 [SMILES: COC(=O)c1ccc(-c2ccn3c(CC4CC4(F)F)nnc3c2Br)c(Cl)c1] |
| 86 | 8-Bromo-3-((2,2-difluorocyclopropyl) methyl)-7-(2,3-benzodihydrofuran-5-yl)-[1,2,4]triazole[4,3-a]pyridine | 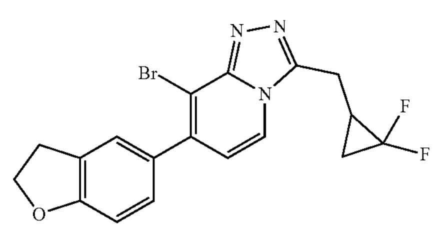 |

TABLE A-continued

| No. | Name | structure |
|-----|------|-----------|
| 87 | 6-(8-Bromo-3-((2,2-difluorocyclopropyl)methyl)-[1,2,4]triazole[4,3-a]pyridine-7-quinoline | 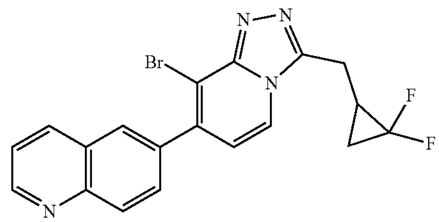 [SMILES: FC1(F)CC1Cc1nnc2c(Br)c(-c3ccc4ncccc4c3)ccn12] |
| 88 | 7-(Benzo[d][1,3]dioxole-5-yl)-8-bromo-3-((2,2-difluorocyclopropyl)methyl)-[1,2,4]triazole[4,3-a]pyridine | 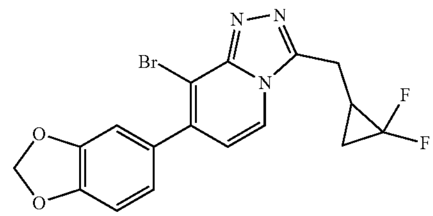 |
| 89 | 3-((2,2-difluorocyclopropyl)methyl)-7-(4-(2-(trifluoromethyl)phenyl)piperidin-1-yl)-[1,2,4]triazole[4,3-a]pyridine-8-carbonitrile | 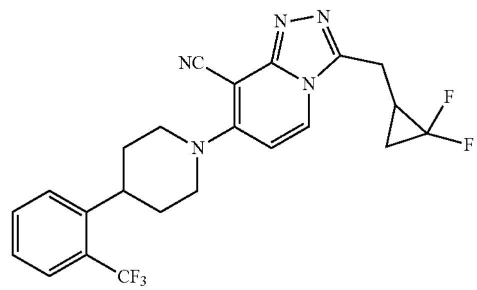 [SMILES: N#Cc1c(N2CCC(c3ccccc3C(F)(F)F)CC2)ccn2c(CC3CC3(F)F)nnc12] |
| 90 | 3-((2,2-difluorocyclopropyl)methyl)-7-(4-hydroxy-4-phenylpiperidin-1-yl)-[1,2,4]triazole[4,3-a]pyridine-8-carbonitrile | 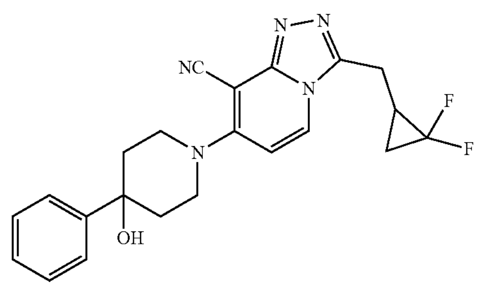 [SMILES: N#Cc1c(N2CCC(O)(c3ccccc3)CC2)ccn2c(CC3CC3(F)F)nnc12] |
| 91 | 7-(4-(2-Chlorophenyl)piperazin-1-yl)-3-((2,2-difluorocyclopropyl)methyl)-[1,2,4]triazole[4,3-a]pyridine-8-carbonitrile | 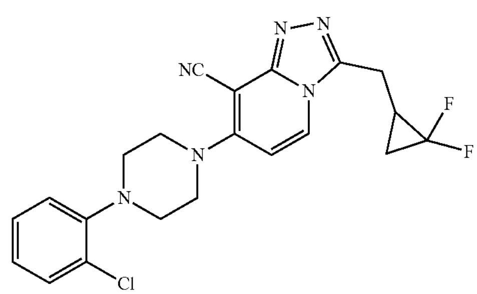 |
| 92 | 3-((2,2-difluorocyclopropyl)methyl)-7-(3-fluorophenyl)-[1,2,4]triazole[4,3-a]pyridine-8-carbonitrile | 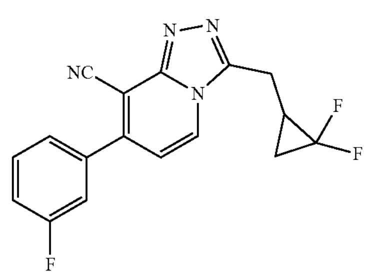 |

TABLE A-continued

| No. | Name | structure |
|---|---|---|
| 93 | 3-((2,2-difluorocyclopropyl)methyl)-7-(4-(2-hydroxypropan-2-yl)phenyl)-[1,2,4]triazole[4,3-a]pyridine-8-carbonitrile | 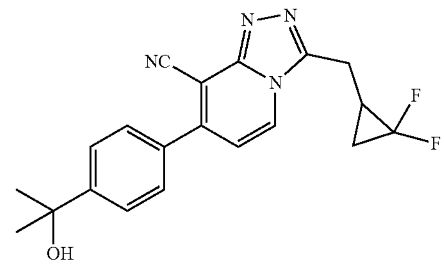 |
| 94 | 3-((2,2-difluorocyclopropyl)methyl)-7-(2,3-benzodihydrofuran-5-yl)-[1,2,4]triazole[4,3-a]pyridine-8-carbonitrile | 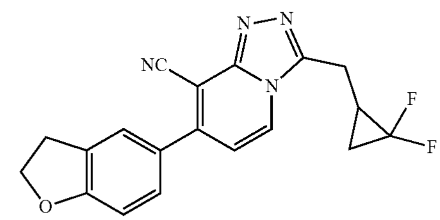 |
| 95 | 3-((2,2-difluorocyclopropyl)methyl)-7-(quinolin-6-yl)-[1,2,4]triazole[4,3-a]pyridine-8-carbonitrile | 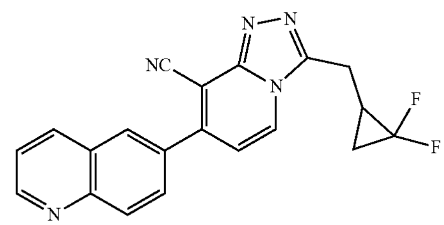 |
| 96 | 7-(Benzo[d][1,3]dioxole-5-yl)-3-((2,2-difluorocyclopropyl)methyl)-[1,2,4]triazole[4,3-a]pyridine-8-carbonitrile | 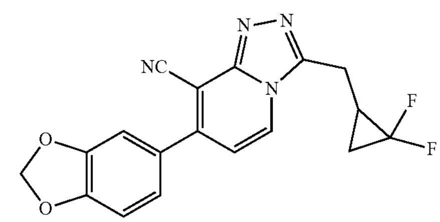 [SMILES: N#Cc1c(-c2ccc3c(c2)OCO3)ccn2c(CC3CC3(F)F)nnc12] |
| 97 | 3-((2,2-difluorocyclopropyl)methyl)-7-(3-fluorophenyl)-8-(trifluoromethyl)-[1,2,4]triazole[4,3-a]pyridine | 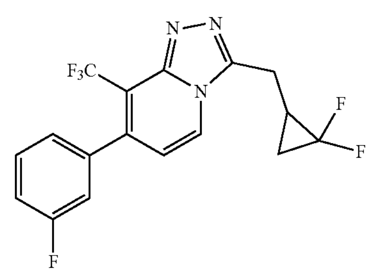 |
| 98 | 2-(4-(3-((2,2-difluorocyclopropyl)methyl)-8-(trifluoromethyl)-[1,2,4]triazole[4,3-a]pyridine-7-yl)phenyl)propan-2-ol | 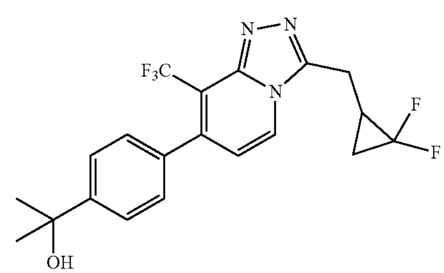 |

TABLE A-continued

| No. | Name | structure |
|---|---|---|
| 99 | 3-((2,2-difluorocyclopropyl)methyl)-7-(3-fluoro-4-methoxyphenyl)-8-(trifluoromethyl)-[1,2,4]triazole[4,3-a]pyridine | 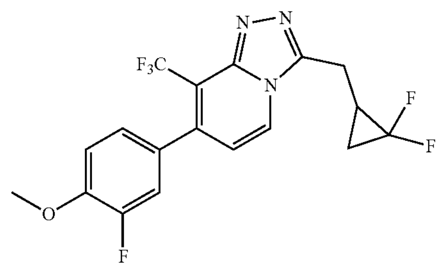 |
| 100 | Methyl 4-(3-((2,2-difluorocyclopropyl)methyl)-8-(trifluoromethyl)-[1,2,4]triazole[4,3-a]pyridin-7-yl)-3-fluorobenzonate | 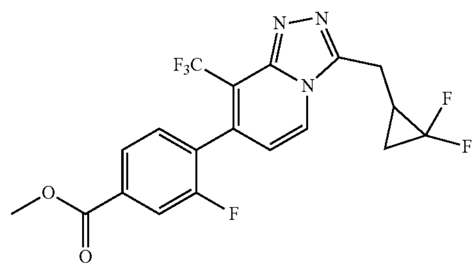 [SMILES: COC(=O)c1ccc(-c2ccn3c(CC4CC4(F)F)nnc3c2C(F)(F)F)c(F)c1] |
| 101 | 3-((2,2-difluorocyclopropyl)methyl)-7-(2,3-benzodihydrofuran-5-yl)-8-(trifluoromethyl)-[1,2,4]triazole[4,3-a]pyridine | 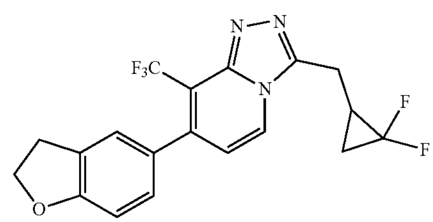 [SMILES: FC(F)(F)c1c(-c2ccc3c(c2)CCO3)ccn2c(CC3CC3(F)F)nnc12] |
| 102 | 6-(3-((2,2-difluorocyclopropyl)methyl)-8-(trifluoromethyl)-[1,2,4]triazole[4,3-a]pyridin-7-yl)quinoline | 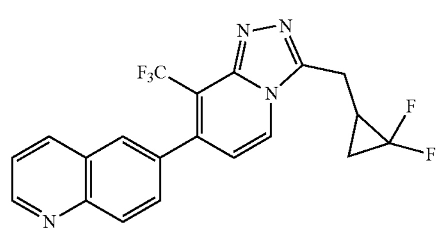 |
| 103 | 7-(Benzo[d][1,3]dioxol-5-yl)-3-((2,2-difluorocyclopropyl)methyl)-8-(trifluoromethyl)-[1,2,4]triazole[4,3-a]pyridine | 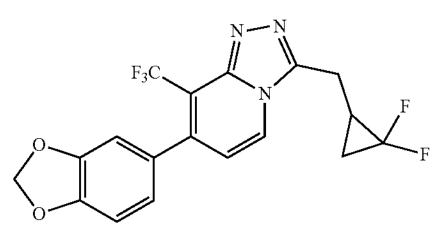 [SMILES: FC(F)(F)c1c(-c2ccc3c(c2)OCO3)ccn2c(CC3CC3(F)F)nnc12] |
| 104 | 3-((2,2-difluorocyclopropyl)methyl)-7-(pyrimidin-2-yl)-8-(trifluoromethyl)-[1,2,4]triazole[4,3-a]pyridine | 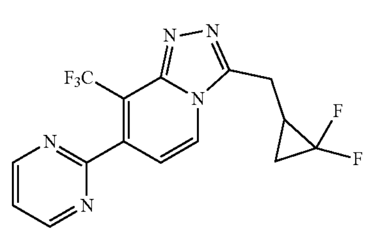 [SMILES: FC(F)(F)c1c(-c2ncccn2)ccn2c(CC3CC3(F)F)nnc12] |

TABLE A-continued

| No. | Name | structure |
|---|---|---|
| 105 | 3-((2,2-difluorocyclopropyl)methyl)-7-(isoindoline-2-yl)-8-(trifluoromethyl)-[1,2,4]triazole[4,3-a]pyridine | 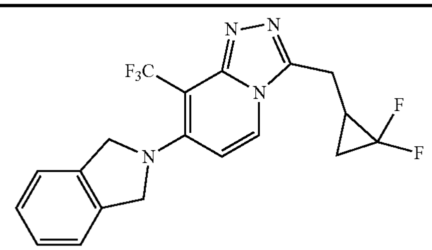 |
| 106 | 4-(3-((2,2-difluorocyclopropyl)methyl)-8-(trifluoromethyl)-[1,2,4]triazole[4,3-a]pyridin-7-yl)morpholine | 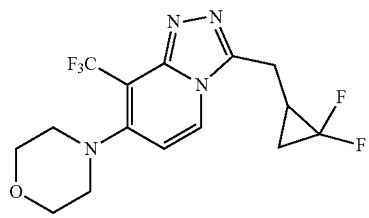 [SMILES: FC(F)(F)c1c(N2CCOCC2)ccn2c(CC3CC3(F)F)nnc12] |

In the second aspect of the present invention, a pharmaceutical composition is provided, wherein the pharmaceutical composition comprises: (a) therapeutically effective amount of compound of the first aspect of the invention, or the pharmaceutically acceptable salt, racemate, R-isomer, S-isomer thereof, or the combinations thereof, and (b) pharmaceutically acceptable carriers.

In another preferred embodiment, the pharmaceutical composition can be used in the treatment of a central nervous system and psychiatric system-related disease, preferably for the treatment of a disease selected from the group consisting of schizophrenia, anxiety, depression, AD, pain, epilepsy and drug addiction.

In another preferred embodiment, the composition is in a injection form.

In another preferred embodiment, the composition is in an oral dosage form.

In the third aspect of the present invention, a mGluR2 positive allosteric modulator is provided, comprising a compound of the first aspect of the invention, a pharmaceutically acceptable salt thereof, racemate, R-isomer, S-isomer, or combination thereof.

In the fourth aspect of the present invention, the use of a compound as described in the first aspect of the invention, or a pharmaceutically acceptable salt thereof, racemate, R-isomer, S-isomer thereof, or mixture thereof in preparing medicines for the treatment of diseases associated with mGluR2 (metabotropic glutamate receptor second subtype) is provided.

In another preferred embodiment, the disease is a disease associated with the central nervous system and psychiatric disorder, preferably a disease selected from the group consisting of schizophrenia, anxiety, depression, AD, pain, epilepsy and drug addiction.

In the fifth aspect of the present invention, the use of compound of the first aspect of the present invention or the pharmaceutically acceptable salt thereof, racemate, R-isomer, S-isomer thereof, or mixture thereof is provided, in the preparation of mGluR2 positive allosteric modulators.

In the sixth aspect of the present invention, a method for treating and/or preventing diseases associated with mGLuR2 is provided, comprising administering to a subject in need thereof with a therapeutically effective amount of a compound as described in the first aspect, or a racemate, R-isomer, S-isomer thereof, pharmaceutically acceptable salt thereof, or mixture thereof.

In another preferred embodiment, the disease is a disease associated with the central nervous system and/or psychiatric disorder, preferably a disease selected from the group consisting of schizophrenia, anxiety, depression, AD, pain, epilepsy and drug addiction.

It should be understood that, in the present invention, each of the technical features specifically described above and below (such as those in the Examples) can be combined with each other, thereby constituting new or preferred technical solutions which need not be specified again herein.

EMBODIMENTS FOR CARRYING OUT THE INVENTION

Through long-term and intensive study, the applicant has provided a mGluR2 positive allosteric modulators as shown in Formula I. The modulators can highlt selectively activate mGluR2 without activating other homologous metabolites Glutamate receptors, or of weak activating effect, thus can be used for the preparation of medicine for treatment of mGluR2-related diseases, such as the central nervous system and psychiatric system-related diseases. The present invention is completed on this basis.

Before the present invention is described, it is to be understood that the invention is not limited to the specific methods and experimental conditions described, as such methods and conditions may vary. It also should be understood that the terminology used herein is for the purpose of describing the particular embodiments, and is not intended to being limitation. The scope of the invention should only be restricted by the attached claims.

Unless otherwise defined, all technical and scientific terms used herein have the same meaning as commonly understood by one of ordinary skill in the art to which this invention belongs. As used herein, when used in reference to a particular recited value, the term "about" means that the value can vary by no more than 1% from the recited value. For example, as used herein, the expression "about 100" includes all the values between 99 and 101 and (eg, 99.1, 99.2, 99.3, 99.4, etc.).

Although any methods and materials similar or equivalent to those described in the present invention can be used in the practice or testing of the present invention, the preferred methods and materials are exemplified herein.

mGluR2 Positive Allosteric Modulators Related Diseases

Schizophrenia is a clinical syndrome consisting of a group of symptomatic groups. It is often slow or subacute onset in young and middle-aged patients. It is often clinically syndromes characterized by different symptoms, involving various obstacles such as perception, thinking, emotion and behavior, and disharmony of mental activity. The patient is generally conscious and possesses basically normal intelligence, but some patients may suffer from cognitive impairment during the course of the disease. The course of the disease is generally delayed, recurrent, aggravated or worsened, and some patients eventually experience recession and mental disability. Among them, emotional disorders such as anxiety and depression, as well as cognitive impairment and will decline, are the most common, which seriously affect the daily life of patients. In recent years, with the rapid development of society, pressures from various aspects such as economic and emotional have made the incidence of schizophrenia higher and higher, and about 1% of the world's population suffers from schizophrenia. At present, antipsychotic drugs are the most preferred clinical treatment for schizophrenia, and it is ineffective to 10% to 30% of patients with schizophrenia (called refractory schizophrenia).

Traditional antipsychotic drugs (such as chlorpromazine), which act on D2, can cause side effects such as extrapyramidal symptoms and have no therapeutic effect on negative symptoms. Non-traditional antipsychotic drugs (such as clozapine), in addition to D2, can also act on 5-HT2A, thus reducing extrapyramidal symptoms, and being effective to both negative and positive symptoms. However, weight gain is a major side effect, meanwhile, there are side effects such as elevated prolactin and glucose, and sedation (which reduced patient compliance). Using mGluR2 positive allosteric modulator for the treatment of schizophrenia is the first new mechanism with important therapeutic effects in recent years.

Anxiety is one of the most common emotional states, such as stressful fears that encourage people to actively do things that alleviate anxiety. This anxiety is a protective response, also known as physiological anxiety. When the severity of anxiety is clearly inconsistent with an objective event or situation, or if the duration is too long, it becomes a pathological anxiety called anxiety symptom. According to foreign reports, the incidence rate in the general population is about 4%, and it accounts for 6 to 27% of psychiatric outpatient clinics. In the United States, it was estimated that the lifetime risk in normal population is 5%, and the domestic incidence is lower, 7‰ in average. Wartime anxiety accounts for 1% of wartime neurosis. It often started in adolescence, and the ratio of male to female is 2:3.

There are many opinions about the pathogenesis of anxiety disorders. At present, the long-term use of anti-anxiety drugs such as benzodiazepines in clinical use leads to physical dependence. And it must be carried out slowly when stopping the drug, and it is not advisable to withdraw the drug suddenly. Another class of drugs that are effective in the treatment of this disease is buspirones, which does not cause physical dependence, but it takes more than two weeks to work. At present, clinical studies have shown that the activation of mGluR2 has an anxiolytic effect.

Drug dependence is a chronic recurrent brain disease characterized by loss of control and compulsive continuous medication, in which opioid abuse is more common in China. Long-term abuse of opioids can lead to serious physical and mental dependence and is highly socially harmful. Studies have shown that mGluR2 couples with Gi/o, which inhibits the activity of adenylate cyclase after activation, reduces cAMP, and directly regulates ion channels and their downstream signaling pathways. The activation of mGluR2 negatively regulates the reward loop in the brain, participates in the formation of conditional aversive reactions during drug dependence and withdrawal, and reduces the reward and drug-seeking behavior after long-term drug treatment. According to reports in the literature, activation of mGluR2 can reduce the drug-seeking behavior induced by cocaine. The mGluR2/3 agonist LY379268 can reduce the recurrence of clue-induced drug-seeking behavior of methamphetamine. The mGluR2 positive allosteric modulator provides a new direction for solving drug dependence problems.

Depression is a form of seizure of manic depression. It is characterized by low mood, slow thinking, reduced speech movement and sluggish. Depression seriously afflicts patients' lives and work, and places a heavy burden on families and society. About 15% of depressed patients die from suicide. A joint study by the World Health Organization, the World Bank and Harvard University shows that depression has become the second most common disease burden in China. The physiological cause of the disease may be related to the decreased concentration of synaptic interstitial neurotransmitter (5-HT) and norepinephrine (NE) in the synaptic cleft of the brain. After using many antidepressants, such as selective serotonin reuptake inhibitors (S SRI) or selective serotonin and norepinephrine reuptake inhibitors (SNRI), etc., although the synaptic cleft concentration of these neurotransmitters rises quickly, the antidepressant effect usually takes about 2 weeks to work. Clinical studies have shown that mGluR2 and 5-HT2A receptors can form dimers, and the activation of mGluR2 can further link with some physiological functions of 5-HT2A, and it has a certain effect on depression. Therefore, mGluR2 positive allosteric modulators have a good prospect for the treatment of depression. In addition, many animal experiments have demonstrated that activation of mGluR2 is a novel approach to the treatment of various diseases such as epilepsy, Parkinson's disease, pain, and Huntington's disease. It is highly needed to develop safe, effective and highly selective mGluR5 negative allosteric regulators.

Terms

As used herein, the halogen is F, Cl, Br or I.

As used herein, the term "C1-C6 alkyl" refers to a linear or branched alkyl with 1 to 6 carbon atoms, which non-limiting comprises methyl, ethyl, propyl, isopropyl, butyl, isobutyl, sec-butyl, tert-butyl, pentyl and hexyl, or the like.

The term "C1-C6 alkoxy" refers to a straight or branched chain alkoxy group having 1 to 6 carbon atoms, which non-limiting comprises methoxy, ethoxy, propoxy, isopropoxy, butoxy, iso-butoxy, butoxy, or the like.

As used herein, the term "C2-C6 alkenyl" refers to a straight or branched alkenyl group having one double bond having 2-6 carbon atoms, which non-limiting comprises vinyl, propenyl, butenyl, isobutenyl, pentenyl and hexenyl.

As used herein, the term "C2-C6 alkynyl" refers to a straight or branched alkynyl group having one triple bond having from 2 to 6 carbon atoms, including, without limitation, ethynyl, propynyl, butynyl, Isobutynyl, pentynyl and hexynyl.

As used herein, the term "C3-C10 cycloalkyl" refers to a cyclic alkyl group having 3 to 10 carbon atoms on the ring, which non-limiting comprises cyclopropyl, cyclobutyl, cyclopentyl, cyclohexyl, cycloheptyl, cyclooctyl and cyclodecyl. The terms "C3-C8 cycloalkyl", "C3-C7 cycloalkyl" and "C3-C6 cycloalkyl" have similar meanings.

As used herein, the term "C6-C12 aryl" refers to an aryl group having 6 to 12 carbon atoms which do not comprise heteroatoms on the ring, such as phenyl, naphthyl and the like. The term "C6-C10 aryl" has a similar meaning.

As used herein, the term "3-12 membered heterocyclyl" refers to a saturated or unsaturated 3-12 membered ring group having 1 to 3 heteroatoms selected from oxygen, sulfur or nitrogen on the ring, such as oxepanyl. The term "3-7 membered heterocyclyl" has a similar meaning.

As used herein, the term "substituted" means that one or more hydrogen atoms on a particular group are replaced by a specific substituent. The specific substituent is a substituent which is correspondingly described in the foregoing, or a substituent which appears in each embodiment. Unless otherwise indicated, an optionally substituted group may have a substituent selected from a particular group at any substitutable position of the group, wherein the substituents may be the same or different at each position. A cyclic substituent, such as a heterocycloalkyl group, may be attached to another ring, such as a cycloalkyl group, to form a spirobicyclic ring system, for example, two rings having a common carbon atom. Those skilled in the art will appreciate that the combinations of substituents contemplated by the present invention are those that are stable or chemically achievable. The substituents are, for example but not limited to, C1-C8 alkyl, C2-C8 alkenyl, C2-C8 alkynyl, C3-C8 cycloalkyl, 3- to 12-membered heterocyclic group, aryl, heteroaryl, halogen, hydroxy, carboxy (—COOH), C1-C8 aldehyde, C2-C10 acyl, C2-C10 ester group, amino, cyano.

For convenience and in accordance with conventional understanding, the term "optional substituted" or "optionally substituted" applies only to sites which are capable of being substituted by a substituent, and does not include those which are not chemically achievable.

In the present invention, unless otherwise specified, the terms used have the general meaning known by those skilled in the art.

Pharmaceutically Acceptable Salts

The present invention provides a pharmaceutically acceptable salt of a compound of formula I, in particular a compound of formula I, with an inorganic or organic acid to form a conventional pharmaceutically acceptable salt. For example, conventional pharmaceutically acceptable salts may be prepared by reacting a compound of formula I with an inorganic mineral acid, such as hydrochloric acid, hydrobromic acid, sulfuric acid, nitric acid, aminosulfonic acid and phosphoric acid, and the like, and organic acids include citric acid, tartaric acid, lactic acid, pyruvic acid, acetic acid, benzenesulfonic acid, p-toluenesulfonic acid, methanesulfonic acid, naphthalenesulfonic acid, ethanesulfonic acid, naphthalene disulfonic acid, maleic acid, malic acid, malonic acid, fumaric acid, succinic acid, propionic acid, oxalic acid, trifluoroacetic acid, stearic acid, pamoic acid, hydroxymaleic acid, phenylacetic acid, benzoic acid, salicylic acid, glutamic acid, ascorbic acid, p-anilinesulfonic acid, 2-acetoxybenzoic acid and isethionic acid; or sodium, potassium, calcium, aluminum or ammonium salts of the compound of formula I with an inorganic base; or a salt formed by compound of formula I with an organic base, such as methanamine salt, ethylamine salt or ethanolamine salt.

The Preparation of Compound of Formula I

In a preferred embodyment of the present invention, the preparation of a compound of formula I is carried out according to the following scheme (example):

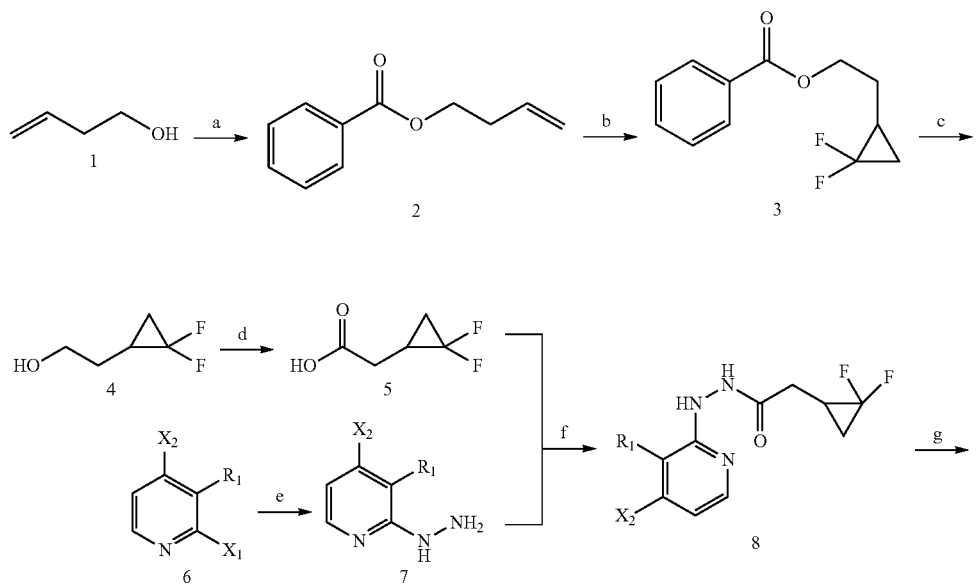

-continued

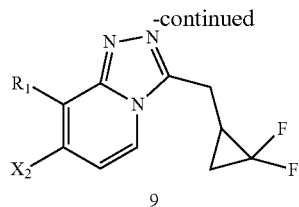

9 h

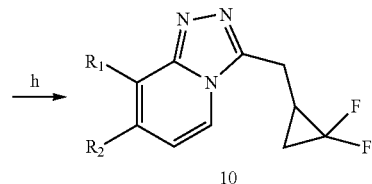

10

Step a: Compound 1 is dissolved in anhydrous dichloromethane, and triethylamine and benzoyl chloride are added with stirring at 0° C. After the addition is completed, the reaction is transferred to room temperature and stirred for 16 hours to obtain intermediate 2;

Step b: the intermediate 2 and sodium fluoride are added to a two-necked flask, sealed and purged with nitrogen. A certain amount of trimethylsilyldifluoro(fluorosulfonyl)acetate is added under heating and stirring at 125° C. After the addition is completed, the reaction solution is stirred at 125° C. for 12 hours to obtain intermediate 3;

Step c: Intermediate 3 is dissolved in a certain amount of sodium hydroxide solution, and heated to reflux to obtain compound 4;

Step d: The chromium trioxide is dissolved in a sulfuric acid solution, and the acetone solution of the compound 4 is added dropwise with stirring at 0° C. The reaction is maintained at 0° C. until the reaction is completed to obtain intermediate 5;

Step e: Compound 6 is dissolved in 1,4-dioxane and a certain amount of hydrazine hydrate is added. The reaction solution is refluxed at 70° C. to obtain intermediate 7;

Step f: the intermediate 5 is dissolved in anhydrous dichloromethane, a certain amount of EDCI, HOBT and triethylamine is added, and then condensed with intermediate 7 to obtain intermediate 8;

Step g: intermediate 8 is heated to obtain intermediate 9;

Step h: Intermediate 9 is dissolved in an organic solvent with another substituted piperidine or aromatic boronic acid substrate, a certain amount of alkali or tetrakistriphenylphosphine palladium is added thereto, the coupling reaction is carried out by microwave heating, and compound 10 is obtained through purification. The organic solvent is acetonitrile, toluene, ethylene glycol dimethyl ether, dioxane or a mixture thereof; the base is sodium carbonate, sodium hydrogencarbonate, triethylamine or diisopropylethylenediamine; and the temperature range of microwave heating is from 120 to 180° C.

The other compounds may be prepared by similar methods by selecting different starting materials.

Pharmaceutical Composition and the Administration Thereof

The compounds of the present invention possess outstanding activity of regulating mGluR2 positive allosteric. Therefore, the compound of the present invention, and the crystal forms, pharmaceutically acceptable inorganic or organic salts, hydrates or solvates thereof, and the pharmaceutical composition comprising the compound of the present invention as a main active ingredient can be used for treating, preventing and alleviating diseases related to mGluR2 positive allosteric, such as central nervous system and psychiatric related diseases, etc.

The pharmaceutical composition of the invention comprises the compound of the present invention or the pharmaceutically acceptable salts thereof in a safe and effective dosage range and pharmaceutically acceptable excipients or carriers. Wherein the "safe and effective dosage" means that the amount of compound is sufficient to significantly ameliorate the condition without causing significant side effects. Generally, the pharmaceutical composition contains 1-3000 (active dose range 3-30 mg/kg) mg compound of the invention per dose, preferably, 10-2000 mg compound of the invention per dose. Preferably, the "dose" is a capsule or tablet. "Pharmaceutically acceptable carrier" means one or more compatible solid or liquid fillers, or gelatinous materials which are suitable for human use and should be of sufficient purity and sufficiently low toxicity. "Compatibility" means that each component in the composition can be admixed with the compounds of the present invention and with each other without significantly reducing the efficacy of the compounds. Some examples of pharmaceutically acceptable carriers include cellulose and the derivatives thereof (such as sodium carboxymethyl cellulose, sodium ethyl cellulose, cellulose acetate, etc.), gelatin, talc, solid lubricants (such as stearic acid, magnesium stearate), calcium sulfate, vegetable oils (such as soybean oil, sesame oil, peanut oil, olive oil, etc.), polyols (such as propylene glycol, glycerol, mannitol, sorbitol, etc.), emulsifiers (such as Tween®), wetting agent (such as sodium dodecyl sulfate), coloring agents, flavoring agents, stabilizers, antioxidants, preservatives, pyrogen-free water, etc.

There is no special limitation of administration mode for the compound or pharmaceutical compositions of the present invention, and the representative administration mode includes (but is not limited to): oral, intratumoral, rectal, parenteral (intravenous, intramuscular or subcutaneous), and topical administration.

Solid dosage forms for oral administration include capsules, tablets, pills, powders and granules. In these solid dosage forms, the active compounds are mixed with at least one conventional inert excipient (or carrier), such as sodium citrate or CaHPO4, or mixed with any of the following components: (a) fillers or compatibilizer, for example, starch, lactose, sucrose, glucose, mannitol and silicic acid; (b) binders, for example, hydroxymethyl cellulose, alginates, gelatin, polyvinylpyrrolidone, sucrose and arabic gum; (c) humectant, such as, glycerol; (d) disintegrating agents such as agar, calcium carbonate, potato starch or tapioca starch, alginic acid, certain composite silicates, and sodium carbonate; (e) dissolution-retarding agents, such as paraffin; (0 absorption accelerators, for example, quaternary ammonium compounds; (g) wetting agents, such as cetyl alcohol and glyceryl monostearate; (h) adsorbents, for example, kaolin; and (i) lubricants such as talc, stearin calcium, magnesium stearate, solid polyethylene glycol, sodium lauryl sulfate, or the mixtures thereof. In capsules, tablets and pills, the dosage forms may also contain buffering agents.

The solid dosage forms such as tablets, sugar pills, capsules, pills and granules can be prepared by using coating and shell materials, such as enteric coatings and any other materials known in the art. They can contain an opaque agent. The release of the active compounds or compounds in the compositions can be released in a delayed mode in a given portion of the digestive tract. Examples of the embedding components include polymers and waxes. If necessary, the active compounds and one or more above excipients can form microcapsules.

Liquid dosage forms for oral administration include pharmaceutically acceptable emulsions, solutions, suspensions, syrups or tinctures. In addition to the active compounds, the liquid dosage forms may contain any conventional inert diluents known in the art such as water or other solvents, solubilizers and emulsifiers, for example, ethanol, isopropanol, ethyl carbonate, ethyl acetate, propylene glycol, 1,3-butanediol, dimethyl formamide, as well as oil, in particular, cottonseed oil, peanut oil, corn germ oil, olive oil, castor oil and sesame oil, or the combination thereof.

Besides these inert diluents, the composition may also contain additives such as wetting agents, emulsifiers, and suspending agent, sweetener, flavoring agents and perfume.

In addition to the active compounds, the suspension may contain suspending agent, for example, ethoxylated isooctadecanol, polyoxyethylene sorbitol and sorbitan esters, microcrystalline cellulose, methanol aluminum and agar, or the combination thereof.

The compositions for parenteral injection may comprise physiologically acceptable sterile aqueous or anhydrous solutions, dispersions, suspensions or emulsions, and sterile powders which can be re-dissolved into sterile injectable solutions or dispersions. Suitable aqueous and non-aqueous carriers, diluents, solvents or excipients include water, ethanol, polyols and any suitable mixtures thereof.

The dosage forms for topical administration of compounds of the invention include ointments, powders, patches, aerosol, and inhalants. The active ingredients are mixed with physiologically acceptable carriers and any preservatives, buffers, or propellant if necessary, under sterile conditions.

Compounds of the present invention can be administrated alone, or in combination with any other pharmaceutically acceptable compounds.

When the pharmaceutical compositions are used, a safe and effective amount of compound of the present invention is applied to a mammal (such as human) in need of, wherein the dose of administration is a pharmaceutically effective dose. For a person weighed 60 kg, the daily dose is usually 1-2000 mg, preferably 6-600 mg. Of course, the particular dose should also depend on various factors, such as the route of administration, patient healthy status, which are well within the skills of an experienced physician.

The main advantages of the present invention are:

(1) A compound of formula I is provided for the first time.

(2) The compound of the formula I of the present invention can work as a mGluR2 positive allosteric modulator.

(3) The activity of the fluorine-containing triazolopyridine compound according to the present invention to mGluR2 is about 10 times higher than that of the fluorine-free triazolopyridine compound corresponding to each compound.

(4) The compound I of the present invention can activate mGluR2 in high selectively without activating other homologous metabolites Glutamate receptors, or of weak activating effect, thus can be used for the preparation of medicine for treatment of mGluR2-related diseases, such as the central nervous system and psychiatric system-related diseases.

The present invention will be further illustrated below with reference to the specific examples. It should be understood that these examples are only to illustrate the invention but not to limit the scope of the invention. The experimental methods with no specific conditions described in the following examples are generally performed under the conventional conditions, or according to the manufacturer's instructions. Unless indicated otherwise, parts and percentage are calculated by weight. The starting materials used in the present invention are commercially available without being specifically described.

Example 1 Preparation of 3-((2,2-Difluorocyclopropyl)methyl)-7-(4-phenylpiperidin-1-yl)-[1,2,4]triazole[4,3-a]pyridine (1)

1.1 Preparation of but-3-en-1-ylbenzoic acid 3.4 g (47.2 mmol) of 3-buten-1-ol was dissolved in 30 mL of anhydrous dichloromethane, and 7.9 mL (56.6 mmol) of triethylamine and 6.5 mL (56.6 mmol) of benzoyl chloride were added with stirring at 0° C. After the addition was completed, the reaction was transferred at room temperature and stirred for 16 hours. After 30 mL of a saturated sodium hydrogencarbonate solution was added to the reaction mixture, the methylene chloride layer was separated by separating funnel, and the aqueous layer was extracted with dichloromethane (30 mL×3). The combined organic layer was dried over anhydrous sodium sulfate. After filtration, the filtrate was concentrated and purified by rapid preparative liquid phase ($V_{petroleum\ ether}$: $V_{ethyl\ acetate}$=1:99) to obtain 6.9 g of colorless liquid as but-3-ene-1-ylbenzoic acid, yield 83%.

1.2 Preparation of 2-(2,2-difluorocyclopropyl)ethanol 6.9 g (39.2 mmol) of but-3-en-1-ylbenzoic acid and 19.8 mg (0.47 mmol) dry sodium fluoride were placed in a two-necked flask, sealed and purged with nitrogen. 14.7 g (58.8 mmol) of trimethylsilyl difluoro(fluorosulfonyl) acetate was slowly added dropwise with a dropping funnel under heating and stirring at 125° C. After the addition was completed, the reaction solution was stirred at 125° C. for 12 hours. After cooling the reaction solution to room temperature, 75 mL of 10% sodium hydroxide solution was added, and the reaction was refluxed for 3 hours. After the reaction solution was cooled to room temperature, diethyl ether (30 mL×5) was added to extract the organic layer. The organic layers were combined, washed with water and a 0.1 M hydrochloric acid solution, and then washed with water and saturated saline. The organic layer was dried over anhydrous sodium sulfate and filtered, and the filtrate was concentrated to give 3.3 g colorless liquid 2-(2,2-difluorocyclopropyl)ethanol in 70% yield.

1.3 Preparation of 2-(2,2-difluorocyclopropyl)acetic acid 5.41 g (54.1 mmol) of chromium trioxide was dissolved in 90.2 mL of 1.5 M sulfuric acid solution, and cooled at with stirring 0° C. 3.3 g (27.1 mmol) of 2-(2,2-difluorocyclopropyl)ethanol was dissolved in 90.2 mL of acetone. The mixture was added dropwise to a chromium trioxide-sulfuric acid solution with stirring at 0° C. After the addition was completed, the reaction solution was stirred at 0° C. for 4 hours. The organic layer was extracted with diethyl ether (50 mL×4). The combined organic layers were washed with brine. It was then extracted with 2 M sodium hydroxide solution (50 mL×4) and the aqueous layers were combined. The aqueous layer was acidified to pH<1 with sulfuric acid with stirring in an ice bath. The organic layer was extracted with diethyl ether (50 mL×4), and the combined organic layers were washed with water and saturated brine. The organic layer was dried over anhydrous sodium sulfate and filtered, and the filtrate was concentrated to give 3.4 g colorless liquid 2-(2,2-difluorocyclopropyl)acetic acid in 92% yield.

1.4 Preparation of 4-chloro-2-hydrazonepyridine 4.2 g (32 mmol) of 2-fluoro-4-chloropyridine was dissolved in 100 mL of 1,4-dioxane, and 15.5 mL of hydrazine hydrate was added with stirring. The reaction solution was refluxed at 70° C. for 16 hours. The reaction solution was cooled to room temperature, added with a 32% aqueous hydroxylamine solution, and concentrated in vacuo. The obtained residue was dissolved in ethanol, and the suspension was heated to reflux. The insoluble material was filtered off when it was hot, while the filtrate was filtered again after cooled to remove the newly formed precipitate. The filtrate was concentrated under reduced pressure to give 4.4 g of tan solids 4-chloro-2-mercaptopyridine, yield 95%.

1.5 N'-(4-chloropyridin-2-yl)-2-(2,2-difluorocyclopropyl)acetylhydrazine 3.4 g (25 mmol) of 2-(2,2-difluorocyclopropyl)acetic acid was dissolved in 120 mL of anhydrous dichloromethane, and then 4.3 g (30 mmol) of 4-chloro-2-mercaptopyridine, 9 g (50 mmol) EDCI, and 6.8 g (50 mmol) HOBT and 20.9 mL (150 mmol) triethylamine were added successively. The reaction solution was stirred at room temperature overnight. After 30 mL of a saturated sodium hydrogencarbonate solution was added, the methylene chloride layer was separated by separating funnel, and the aqueous layer was extracted with dichloromethane (50 mL×3). The combined organic layer is dried over anhydrous sodium sulfate. After filtration, the filtrate was concentrated and purified by rapid preparative liquid phase ($V_{petroleum\ ether}:V_{ethyl\ acetate}$=3:1) to provide 4.0 g pale yellow solids N'-(4-chloropyridin-2-yl)-2-(2,2-difluorocyclopropyl)acetyl hydrazine, yield 61%.

1.6 Preparation of 7-chloro-3-((2,2-difluorocyclopropyl)methyl)-[1,2,4]triazole[4,3-a]pyridine 4.0 g (15.3 mmol) of N'-(4-chloropyridin-2-yl)-2-(2,2-difluorocyclopropyl)acetylhydrazine was placed in a reaction flask, and heated at 160° C. for 3 hours after sealing. The obtained tan viscous material was isolated and purified by rapid preparative liquid phase ($V_{petroleum\ ether}:V_{ethyl\ acetate}$=1:1 to give 1.1 g white solids 7-chloro-3-((2,2-difluorocyclopropyl)methyl)-[1,2,4]triazole[4,3-a]pyridine, yield 30%.

1.7 Preparation of Final Product Compound 1

0.1 g (0.41 mmol) of 7-chloro-3-((2,2-difluorocyclopropyl)methyl)-[1,2,4]triazole[4,3-a]pyridine, 0.50 mmol 4-Phenylpiperidine and 0.11 g (0.82 mmol) of N,N-diisopropylethylenediamine were placed in a microwave reaction tube, and 1 mL of acetonitrile was added thereto, and the mixture was reacted in microwave at 180° C. for 30 minutes. The reaction solution was cooled to room temperature, concentrated under reduced pressure, and purified by column chromatography ($V_{petroleum\ ether}:V_{ethyl\ acetate}$=1:4) to provide compound 1, yield 38%. $^1$H NMR (400 MHz, CDCl$_3$) δ7.76 (d, J=4 Hz, 1H), 7.34 (m, 2H), 7.24 (m, 3H), 6.86 (s, 1H), 6.77 (dd, J=8 Hz, J=4 Hz, 1H), 3.92 (m, 2H), 3.19 (m, 2H), 2.98 (m, 2H), 2.76 (m, 1H), 2.09 (m, 1H), 2.01 (m, 2H), 1.88 (m, 2H), 1.64 (m, 1H), 1.25 (m, 1H). LRMS (ESI) m/z 369 ([M+H]$^+$).

Example 2 Preparation of 3-((2,2-difluorocyclopropyl)methyl)-7-(4-(4-fluorophenyl)piperidin-1-yl)-[1,2,4]triazole[4,3-a]pyridine (Compound 2)

4-Phenylpiperidine was replaced with 4-fluorophenylpiperidine, while the remaining starting materials, reagents and preparation methods were the same as in Example 1 to obtain compound 2 in 36% yield. $^1$H NMR (400 MHz, CDCl$_3$) δ7.96 (d, J=8 Hz, 1H), 7.17 (m, 2H), 7.00 (m, 3H), 6.90 (d, J=8 Hz, 1H), 4.03 (m, 2H), 3.27 (m, 2H), 3.08 (m, 2H), 2.79 (m, 1H), 2.10 (m, 1H), 2.00 (m, 2H), 1.80 (m, 2H), 1.66 (m, 1H), 1.25 (m, 1H). LRMS (ESI) m/z 387 ([M+H]$^+$).

Example 3 Preparation of 7-(4-(4-Chlorophenyl)piperidin-1-yl)-3-((2,2-difluorocyclopropyl)methyl)-[1,2,4]triazole[4,3-a]pyridine (compound 3)

4-phenylpyridine was replaced by 4-chlorophenylpiperidine, while the remaining raw materials, reagents and the preparation method was the same as in example 1 to give compound 3, yield 35%. $^1$H NMR (400 MHz, CDCl$_3$) δ7.91 (d, J=8 Hz, 1H), 7.17 (m, 2H), 7.15 (m, 2H), 6.97 (s, 1H), 6.88 (dd, J=8 Hz, J=4 Hz, 1H), 4.02 (m, 2H), 3.22 (m, 2H), 3.08 (m, 2H), 2.67 (m, 1H), 2.12 (m, 1H), 2.02 (m, 2H), 1.83 (m, 2H), 1.66 (m, 1H), 1.28 (m, 1H). LRMS (ESI) m/z 403 ([M+H]$^+$).

Example 4 Preparation of 7-(4-(3-Chlorophenyl)piperidin-1-yl)-3-((2,2-difluorocyclopropyl)methyl)-[1,2,4]triazole[4,3-a]pyridine (Compound 4)

4-Phenylpiperidine was replaced with 3-chlorophenylpiperidine, while the remaining starting materials, reagents and preparation methods were the same as in Example 1 to obtain compound 4 in 33% yield. $^1$H NMR (400 MHz, CDCl$_3$) δ7.81 (d, J=8 Hz, 1H), 7.24 (m, 1H), 7.21 (m, 2H), 7.10 (m, 1H), 6.86 (s, 1H), 6.78 (dd, J=8 Hz, J=8 Hz, 1H), 3.92 (m, 2H), 3.18 (m, 2H), 2.97 (m, 2H), 2.74 (m, 1H), 2.10 (m, 1H), 1.99 (m, 2H), 1.82 (m, 2H), 1.64 (m, 1H), 1.24 (m, 1H). LRMS (ESI) m/z 403 ([M+H]$^+$).

Example 5 Preparation of 3-((2,2-Difluorocyclopropyl)methyl)-7-(4-(2-(trifluoromethyl)phenyl)piperidin-1-yl)-[1,2,4]triazole[4,3-a]pyridine (Compound 5)

4-Phenylpiperidine was replaced with 4-(2-trifluoromethylphenyl)piperidine, while the remaining starting materials, reagents and preparation methods were the same as in Example 1 to obtain compound 5 in 31% yield. $^1$H NMR (400 MHz, CDCl$_3$) δ7.63 (m, 2H), 7.53 (m, 2H), 7.41 (d, J=8 Hz, 1H), 7.33 (d, J=8 Hz, 1H), 6.88 (m, 1H), 4.00 (d, J=8 Hz, 2H), 3.27 (m, 2H), 3.04 (m, 2H), 2.64 (m, 1H), 2.10 (m, 1H), 2.01 (d, J=4 Hz, 2H), 1.87 (m, 2H), 1.64 (m, 1H), 1.25 (m, 1H). LRMS (ESI) m/z 437 ([M+H]$^+$).

Example 6 Preparation of 1-(3-((2,2-difluorocyclopropyl)methyl)-[1,2,4]triazole[4,3-a]pyridin-7-yl)-4-phenylpiperidin-4-ol (Compound 6)

4-phenylpyridine was replaced by 4-phenylpiperidin-4-ol, while the remaining raw materials, reagents and the preparation method was the same as in example 1 to give compound 6, yield 29%. $^1$H NMR (400 MHz, CDCl$_3$) δ7.74 (d, J=8 Hz, 1H), 7.51 (m, 2H), 7.39 (m, 3H), 6.85 (s, 1H), 6.76 (m, 1H), 5.34 (s, 1H), 3.71 (m, 2H), 3.42 (m, 2H), 3.18 (m, 2H), 2.22 (m, 1H), 2.01 (m, 2H), 1.92 (m, 2H), 1.64 (m, 1H), 1.25 (m, 1H). LRMS (ESI) m/z 385 ([M+H]$^+$).

Example 7 Preparation of 1-(3-((2,2-Difluorocyclopropyl)methyl)-[1,2,4]triazole[4,3-a]pyridin-7-yl)-4-(4-fluoropheny1)piperidin-4-ol (Compound 7)

4-phenylpyridine was replaced by 4-(4-fluorophenylpiperidin-4-ol), while the remaining raw materials, reagents and the preparation method was the same as in example 1 to give compound 7, yield 29%. $^1$H NMR (400 MHz, DMSO-d$_6$) δ8.24 (d, J=8 Hz, 1H), 7.52 (m, 2H), 7.13 (m, 2H), 7.05 (d, J=8 Hz, 1H), 6.79 (s, 1H), 5.25 (s, 1H), 3.79 (d, J=12 Hz, 2H), 3.16 (m, 4H), 2.19 (m, 1H), 1.98 (m, 2H), 1.70 (m, 3H), 1.32 (m, 1H). LRMS (ESI) m/z 403 ([M+H]$^+$).

Example 8 Preparation of 4-(4-Chlorophenyl)-1-(3-((2,2-difluorocyclopropyl)methyl)-[1,2,4]triazole[4,3-a]pyridin-7-yl)piperidin-4-ol (Compound 8)

4-phenylpyridine was replaced by 4-(4-chlorophenylpiperidinyl)-4-ol, while the remaining raw materials, reagents and the preparation method was the same as in example 1 to give compound 8, yield 29%. $^1$H NMR (400 MHz, DMSO-d$_6$) δ8.23 (d, J=4 Hz, 1H), 7.53 (d, J=4 Hz, 2H), 7.40 (d, J=8 Hz, 2H), 7.03 (m, 1H), 6.77 (s, 1H), 5.28 (s, 1H), 3.81 (d, J=8 Hz, 2H), 3.22 (m, 4H), 2.23 (m, 1H), 2.03 (m, 2H), 1.71 (m, 3H), 1.35 (m, 1H). LRMS (ESI) m/z 419 ([M+H]$^+$).

Example 9 Preparation of 4-(4-Chloro-3-(trifluoromethyl)phenyl)-1-(3-((2,2-difluorocyclopropyl)methyl)-[1,2,4]triazole[4,3-a]pyridin-7-yl)piperidin-4-ol (Compound 9)

4-phenylpyridine was replaced by 4-(4-chloro-3-trifluoromethylphenylpiperidine)-4-ol, while the remaining raw materials, reagents and the preparation method was the same as in example 1 to give compound 9, yield 27%. $^1$H NMR (400 MHz, DMSO-d$_6$) δ8.23 (d, J=4 Hz, 1H), 7.97 (d, J=4 Hz, 1H), 7.78 (dd, J=4 Hz, J=8 Hz, 1H), 7.68 (d, J=8 Hz, 1H), 7.02 (dd, J=8 Hz, J=8 Hz, 1H), 6.76 (d, J=4 Hz, 1H), 5.51 (s, 1H), 3.81 (d, J=8 Hz, 2H), 3.22 (m, 4H), 2.21 (m, 1H), 2.09 (m, 2H), 1.68 (m, 3H), 1.35 (m, 1H). LRMS (ESI) m/z 487 ([M+H]$^+$).

Example 10 Preparation of 3-((2,2-difluorocyclopropyl)methyl)-7-(m-tolyl)-[1,2,4]triazole[4,3-a]pyridine (Compound 10)

4-phenylpiperidine was replaced by 3-methylbenzeneboronic acid, N,N-diisopropylethylenediamine was replaced by sodium bicarbonate, and acetonitrile was replaced with 1,4-dioxane, and reacted in microwave at 150° C. for 90 minutes. The remaining starting materials, reagents and preparation methods were the same as in Example 1 to obtain compound 10 in 43% yield. $^1$H NMR (400 MHz, CDCl$_3$) δ7.99 (dd, J=8 Hz, J=4 Hz, 1H), 7.88 (m, 1H), 7.43 (d, J=8 Hz, 2H), 7.37 (m, 1H), 7.24 (m, 1H), 7.16 (dd, J=4 Hz, J=8 Hz, 1H), 3.30 (m, 2H), 2.43 (s, 3H), 2.15 (m, 1H), 1.64 (m, 1H), 1.27 (m, 1H). LRMS (ESI) m/z 300 ([M+H]$^+$).

Example 11 Preparation of 3-((2,2-Difluorocyclopropyl)methyl)-7-(3-fluorophenyl)-[1,2,4]triazole[4,3-a]pyridine (Compound 11)

3-methylbenzeneboronic acid was replaced by 3-fluorobenzeneboronic acid, while the remaining starting materials, reagents and preparation methods were the same as in Example 10 to obtain compound 11 in 41% yield. $^1$H NMR (400 MHz, CDCl$_3$) δ8.03 (d, J=8 Hz, 1H), 7.90 (s, 1H), 7.45 (m, 2H), 7.32 (m, 1H), 7.14 (m, 2H), 3.30 (m, 2H), 2.15 (m, 1H), 1.66 (m, 1H), 1.27 (m, 1H). LRMS (ESI) m/z 304 ([M+H]$^+$).

Example 12 Preparation of 3-((2,2-Difluorocyclopropyl)methyl)-7-(3-(trifluoromethyl)phenyl)-[1,2,4]triazole[4,3-a]pyridine (Compound 12)

3-methylbenzeneboronic acid was replaced by 3-trifluoromethylbenzeneboronic acid, while the remaining starting materials, reagents and preparation methods were the same as in example 10 to obtain compound 12 in 40% yield. $^1$H NMR (400 MHz, CDCl$_3$) δ8.08 (d, J=4 Hz, 1H), 8.00 (s, 1H), 7.91 (s, 1H), 7.87 (d, J=8 Hz, 1H), 7.75 (d, J=4 Hz, 1H), 7.76 (m, 1H), 7.21 (dd, J=4 Hz, J=8 Hz, 1H), 3.37 (m, 2H), 2.19 (m, 1H), 1.71 (m, 1H), 1.30 (m, 1H). LRMS (ESI) m/z 354 ([M+H]$^+$).

Example 13 Preparation of 3-((2,2-Difluorocyclopropyl)methyl)-7-(4-fluorophenyl)-[1,2,4]triazole[4,3-a]pyridine (Compound 13)

3-methylbenzeneboronic acid was replaced by 4-fluorobenzeneboronic acid, while the remaining starting materials, reagents and preparation methods were the same as in Example 10 to obtain compound 13 in 41% yield. $^1$H NMR (400 MHz, CDCl$_3$) δ8.03 (d, J=4 Hz, 1H), 7.92 (s, 1H), 7.64 (m, 2H), 7.21 (m, 2H), 7.16 (dd, J=4 Hz, J=4 Hz, 1H), 3.33 (m, 2H), 2.18 (m, 1H), 1.68 (m, 1H), 1.25 (m, 1H). LRMS (ESI) m/z 304 ([M+H]$^+$).

Example 14 Preparation of 3-((2,2-Difluorocyclopropyl)methyl)-7-(4-(trifluoromethyl)phenyl)-[1,2,4]triazole[4,3-a]pyridine (Compound 14)

3-methylbenzeneboronic acid was replaced by 4-trifluoromethylbenzeneboronic acid, while the remaining starting materials, reagents and preparation methods were the same as in example 10 to obtain compound 14 in 40% yield. $^1$H NMR (400 MHz, CDCl$_3$) δ8.08 (d, J=4 Hz, 1H), 7.96 (s, 1H), 7.77 (m, 4H), 7.18 (dd, J=8 Hz, J=4 Hz, 1H), 3.29 (m, 2H), 2.18 (m, 1H), 1.68 (m, 1H), 1.28 (m, 1H). LRMS (ESI) m/z 354 ([M+H]$^+$).

Example 15 Preparation of 4-(3-((2,2-difluorocyclopropyl)methyl)-[1,2,4]triazo[4,3-a]pyridin-7-yl)benzonitrile (Compound 15)

3-methylbenzeneboronic acid was replaced by 4-cyanobenzeneboronic acid, while the remaining starting materials, reagents and preparation methods were the same as in Example 10 to obtain compound 15 in 37% yield. $^1$H NMR (400 MHz, CDCl$_3$) δ8.10 (d, J=4 Hz, 1H), 7.97 (s, 1H), 7.78 (dd, J=12 Hz, J=12 Hz, 2H), 7.17 (dd, J=4 Hz, J=4 Hz, 1H), 3.29 (m, 2H), 2.17 (m, 1H), 1.68 (m, 1H), 1.28 (m, 1H). LRMS (ESI) m/z 311 ([M+H]+).

Example 16 Preparation of 1-(4-(3-(((2,2-difluorocyclopropyl)methyl)-[1,2,4]triazole[4,3-a]pyridin-7-yl)phenyl)ethano ne (Compound 16)

3-methylbenzeneboronic acid was replaced by 4-acetylphenylboronic acid, while the remaining starting materials, reagents and preparation methods were the same as in Example 10 to obtain compound 16 in 33% yield. $^1$H NMR (400 MHz, CDCl$_3$) δ8.11 (d, J=4 Hz, 1H), 8.07 (d, J=4 Hz, 1H), 8.04 (s, 1H), 7.78 (d, J=8 Hz, 2H), 7.23 (d, J=4 Hz, 1H), 3.33 (m, 2H), 2.68 (s, 3H), 2.19 (m, 1H), 1.69 (m, 1H), 1.29 (m, 1H). LRMS (ESI) m/z 328 ([M+H]+).

Example 17 Preparation of methyl 4-(3-((2,2-Difluorocyclopropyl)methyl)-[1,2,4]triazole[4,3-a]pyridin-7-yl)benzonate (Compound 17)

3-methylbenzeneboronic acid was replaced by 4-methoxycarbonylbenzeneboronic acid, while the remaining starting materials, reagents and preparation methods were the same as in Example 10 to obtain compound 17 in 35% yield. $^1$H NMR (400 MHz, CDCl$_3$) δ8.17 (d, J=8 Hz, 2H), 8.04 (d, J=4 Hz, 1H), 8.00 (s, 1H), 7.73 (d, J=4 Hz, 2H), 7.20 (dd, J=4 Hz, J=8 Hz, 1H), 3.96 (s, 3H), 3.33 (m, 2H), 2.17 (m, 1H), 1.68 (m, 1H), 1.28 (m, 1H). LRMS (ESI) m/z 344 ([M+H]+).

Example 18 Preparation of isopropyl 4-(3-((2,2-Difluorocyclopropyl)methyl)-[1,2,4]triazole[4,3-a]pyridin-7-yl)benzonate (Compound 18)

3-methylbenzeneboronic acid was replaced by 4-isopropyloxycarbonylbenzeneboronic acid, while the remaining starting materials, reagents and preparation methods were the same as in Example 10 to obtain compound 18 in 34% yield. $^1$H NMR (400 MHz, CDCl$_3$) δ8.14 (d, J=8 Hz, 2H), 8.04 (d, J=8 Hz, 1H), 7.97 (s, 1H), 7.70 (d, J=8 Hz, 2H), 7.19 (m, 1H), 5.26 (m, 1H), 3.32 (m, 2H), 2.16 (m, 1H), 1.65 (m, 1H), 1.38 (d, J=8 Hz, 6H), 1.27 (m, 1H). LRMS (ESI) m/z 372 ([M+H]+).

Example 19 Preparation of 3-((2,2-Difluorocyclopropyl)methyl)-7-(4-methoxyphenyl)-[1,2,4]triazole[4,3-a]pyridine (Compound 19)

3-methylbenzeneboronic acid was replaced by 4-methoxybenzeneboronic acid, while the remaining starting materials, reagents and preparation methods were the same as in Example 10 to obtain compound 19 in 34% yield. $^1$H NMR (400 MHz, CDCl$_3$) δ7.96 (d, J=4 Hz, 1H), 7.87 (s, 1H), 7.61 (d, J=8 Hz, 2H), 7.15 (d, J=8 Hz, 1H), 7.03 (d, J=8 Hz, 2H), 3.88 (s, 3H), 3.28 (m, 2H), 2.16 (m, 1H), 1.67 (m, 1H), 1.26 (m, 1H). LRMS (ESI) m/z 316 ([M+H]+).

Example 20 Preparation of (4-(3-((2,2-Difluorocyclopropyl)methyl)-[1,2,4]triazole[4,3-a]pyridin-7-yl)phenyl)methanol (Compound 20)

3-methylbenzeneboronic acid was replaced by 4-hydroxymethylbenzeneboronic acid, while the remaining starting materials, reagents and preparation methods were the same as in Example 10 to obtain compound 20 in 31% yield. $^1$H NMR (400 MHz, CDCl$_3$) δ8.02 (d, J=4 Hz, 1H), 7.79 (s, 1H), 7.60 (d, J=4 Hz, 2H), 7.50 (d, J=4 Hz, 2H), 7.18 (d, J=4 Hz, 1H), 4.77 (s, 2H), 3.73 (s, 1H), 3.27 (m, 2H), 2.16 (m, 1H), 1.66 (m, 1H), 1.28 (m, 1H). LRMS (ESI) m/z 316 ([M+H]+).

Example 21 Preparation of 2-(4-(3-((2,2-difluorocyclopropyl)methyl)-[1,2,4]triazole[4,3-a]pyridin-7-yl)phenyl)propan-2-ol (Compound 21)

The 3-methylbenzeneboronic acid was replaced by 4-(2-hydroxypropan-2-yl)-benzeneboronic acid, while the remaining starting materials, reagents and preparation methods were the same as in Example 10 to obtain compound 21 in 32% yield. $^1$H NMR (400 MHz, DMSO-d$_6$) δ8.51 (d, J=4 Hz, 1H), 8.04 (s, 1H), 7.81 (d, J=8 Hz, 2H), 7.60 (d, J=8 Hz, 2H), 7.39 (dd, J=8 Hz, J=8 Hz, 1H), 5.13 (s, 1H), 3.31 (m, 2H), 2.50 (m, 1H), 2.27 (m, 1H), 1.71 (m, 1H), 1.46 (s, 6H). LRMS (ESI) m/z 344 ([M+H]+).

Example 22 Preparation of 3-((2,2-Difluorocyclopropyl)methyl)-7-(3,4-dimethylphenyl)-[1,2,4]triazole[4,3-a]pyridine (Compound 22)

3-methylbenzeneboronic acid was replaced by 3,4-dimethylboronic acid, while the remaining starting materials, reagents and preparation methods were the same as in Example 10 to obtain compound 22 in 37% yield. $^1$H NMR (400 MHz, CDCl$_3$) δ7.97 (d, J=8 Hz, 1H), 7.90 (s, 1H), 7.39 (m, 2H), 7.25 (d, J=8 Hz, 1H), 7.17 (d, J=8 Hz, 1H), 3.26 (m, 2H), 2.33 (d, J=8 Hz, 6H), 2.14 (m, 1H), 1.65 (m, 1H), 1.27 (m, 1H). LRMS (ESI) m/z 314 ([M+H]+).

Example 23 Preparation of 3-((2,2-Difluorocyclopropyl)methyl)-7-(3-fluoro-4-methoxyphenyl)-[1,2,4]triazole[4,3-a]pyridine (Compound 23)

3-methylbenzeneboronic acid was replaced by 3-fluoro-4-methoxybenzeneboronic acid, while the remaining starting materials, reagents and preparation methods were the same as in Example 10 to obtain compound 23 in 38% yield. $^1$H NMR (400 MHz, CDCl$_3$) δ7.98 (d, J=8 Hz, 1H), 7.83 (s, 1H), 7.37 (m, 2H), 7.09 (m, 2H), 3.94 (s, 3H), 3.30 (m, 2H), 2.16 (m, 1H), 1.66 (m, 1H), 1.28 (m, 1H). LRMS (ESI) m/z 334 ([M+H]+).

Example 24 Preparation of 3-((2,2-Difluorocyclopropyl)methyl)-7-(2-fluoro-4-methoxyphenyl)-[1,2,4]triazole[4,3-a]pyridine (Compound 24)

3-methylbenzeneboronic acid was replaced by 2-fluoro-4-methoxybenzeneboronic acid, while the remaining starting materials, reagents and preparation methods were the same as in Example 10 to obtain compound 24 in 38% yield. $^1$H NMR (400 MHz, CDCl$_3$) δ7.94 (d, J=8 Hz, 1H), 7.85 (s, 1H), 7.35 (dd, J=4 Hz, J=8 Hz, 1H), 7.12 (dd, J=8 Hz, J=4 Hz, 1H), 6.78 (m, 2H), 3.86 (s, 3H), 3.29 (m, 2H), 2.12 (m, 1H), 1.68 (m, 1H), 1.27 (m, 1H). LRMS (ESI) m/z 334 ([M+H]+).

Example 25 Preparation of 3-((2,2-Difluorocyclopropyl)methyl)-7-(4-fluoro-2-methoxyphenyl)-[1,2,4]triazole[4,3-a]pyridine (Compound 25)

3-methylbenzeneboronic acid was replaced by 4-fluoro-2-methoxybenzeneboronic acid, while the remaining starting materials, reagents and preparation methods were the same as in Example 10 to obtain compound 25 in 38% yield. $^1$H NMR (400 MHz, CDCl$_3$) δ7.95 (d, J=4 Hz, 1H), 7.85 (s, 1H), 7.35 (m, 1H), 7.12 (d, J=4 Hz, 1H), 6.78 (m, 2H), 3.86 (s, 3H), 3.29 (m, 2H), 2.16 (m, 1H), 1.68 (m, 1H), 1.28 (m, 1H). LRMS (ESI) m/z 334 ([M+H]$^+$).

Example 26 Preparation of 3-((2,2-Difluorocyclopropyl)methyl)-7-(4-fluoro-2-methylphenyl)-[1,2,4]triazole[4,3-a]pyridine (Compound 26)

3-methylbenzeneboronic acid was replaced by 4-fluoro-2-methylbenzeneboronic acid, while the remaining starting materials, reagents and preparation methods were the same as in Example 10 to obtain compound 26 in 39% yield. $^1$H NMR (400 MHz, CDCl$_3$) δ8.00 (d, J=4 Hz, 1H), 7.67 (s, 1H), 7.26 (dd, J=8 Hz, J=8 Hz, 1H), 7.03 (m, 2H), 6.88 (d, J=4 Hz, 1H), 3.33 (m, 2H), 2.34 (s, 3H), 2.20 (m, 1H), 1.70 (m, 1H), 1.30 (m, 1H). LRMS (ESI) m/z 318 ([M+H]$^+$).

Example 27 Preparation of 3-((2,2-Difluorocyclopropyl)methyl)-7-(4-fluoro-3-methylphenyl)-[1,2,4]triazole[4,3-a]pyridine (Compound 27)

3-methylbenzeneboronic acid was replaced by 4-fluoro-3-methylbenzeneboronic acid, while the remaining starting materials, reagents and preparation methods were the same as in Example 10 to obtain compound 27 in 39% yield. $^1$H NMR (400 MHz, CDCl$_3$) δ8.05 (d, J=4 Hz, 1H), 7.99 (s, 1H), 7.66 (m, 2H), 7.47 (m, 1H), 7.14 (t, J=10 Hz, 1H), 3.28 (m, 2H), 2.38 (s, 3H), 2.16 (m, 1H), 1.68 (m, 1H), 1.27 (m, 1H). LRMS (ESI) m/z 318 ([M+H]$^+$).

Example 28 Preparation of 7-(2-Chloro-4-fluorophenyl)-3-((2,2-difluorocyclopropyl)methyl)-[1,2,4]triazole[4,3-a]pyridine (Compound 28)

3-methylbenzeneboronic acid was replaced by 2-chloro-4-fluorobenzeneboronic acid, while the remaining starting materials, reagents and preparation methods were the same as in Example 10 to obtain compound 28 in 39% yield. $^1$H NMR (400 MHz, CDCl$_3$) δ8.00 (d, J=4 Hz, 1H), 7.78 (s, 1H), 7.40 (dd, J=8 Hz, J=8 Hz, 1H), 7.29 (dd, J=8 Hz, J=4 Hz, 1H), 7.13 (m, 1H), 7.02 (dd, J=8 Hz, J=4 Hz, 1H), 3.33 (m, 2H), 2.18 (m, 1H), 1.68 (m, 1H), 1.25 (m, 1H). LRMS (ESI) m/z 338 ([M+H]$^+$).

Example 29 Preparation of methyl 4-(3-((2,2-Difluorocyclopropyl)methyl)-[1,2,4]triazole[4,3-a]pyridin-7-yl)-3-fluorobenzona to (Compound 29)

3-methylbenzeneboronic acid was replaced by 2-fluoro-4-methoxycarbonylbenzeneboronic acid, while the remaining starting materials, reagents and preparation methods were the same as in Example 10 to obtain compound 29 in 44% yield. $^1$H NMR (400 MHz, CDCl$_3$) δ8.05 (d, J=4 Hz, 1H), 7.99 (s, 1H), 7.96 (dd, J=8 Hz, J=4 Hz, 1H), 7.87 (dd, J=8 Hz, J=12 Hz, 1H), 7.62 (t, J=6 Hz, 1H), 7.18 (m, 1H), 3.98 (s, 3H), 3.32 (m, 2H), 2.19 (m, 1H), 1.69 (m, 1H), 1.29 (m, 1H). LRMS (ESI) m/z 362 ([M+H]$^+$).

Example 30 Preparation of methyl 3-chloro-4-(3-((2,2-difluorocyclopropyl)methyl)-[1,2,4]triazole[4,3-a]pyridin-7-yl)benzonat e (Compound 30)

3-methylbenzeneboronic acid was replaced by 2-chloro-4-methoxycarbonylbenzeneboronic acid, while the remaining starting materials, reagents and preparation methods were the same as in Example 10 to obtain compound 30 in 46% yield. $^1$H NMR (400 MHz, CDCl$_3$) δ8.09 (d, J=8 Hz, 1H), 7.93 (m, 2H), 7.70 (d, 1H), 7.58 (m, 1H), 7.15 (dd, J=4 Hz, J=4 Hz, 1H), 3.94 (s, 3H), 3.29 (m, 2H), 2.16 (m, 1H), 1.65 (m, 1H), 1.27 (m, 1H). LRMS (ESI) m/z 378 ([M+H]$^+$).

Example 31 Preparation of 3-((2,2-Difluorocyclopropyl)methyl)-7-(2,3-benzodihydrofuran-5-yl)-[1,2,4]triazole[4,3-a]pyridine (Compound 31)

3-methylbenzeneboronic acid was replaced by 2,3-dihydrobenzofuran-5-benzeneboronic acid, while the remaining starting materials, reagents and preparation methods were the same as in Example 10 to obtain compound 31 in 41% yield. $^1$H NMR (400 MHz, CDCl$_3$) δ7.96 (dd, J=8 Hz, 1H), 7.86 (s, 1H), 7.51 (s, 1H), 7.43 (dd, J=8 Hz, J=8 Hz, 1H), 7.15 (dd, J=8 Hz, J=4 Hz, 1H), 6.90 (d, J=8 Hz, 1H), 4.67 (t, J=10 Hz, 2H), 3.29 (m, 4H), 2.16 (m, 1H), 1.67 (m, 1H), 1.28 (m, 1H). LRMS (ESI) m/z 328 ([M+H]$^+$).

Example 32 Preparation of 3-((2,2-Difluorocyclopropyl)methyl)-7-(2,3-benzodihydrofuran-7-yl)-[1,2,4]triazole[4,3-a]pyridine (Compound 32)

3-methylbenzeneboronic acid was replaced by 2,3-dihydrobenzofuran-7-benzeneboronic acid, while the remaining starting materials, reagents and preparation methods were the same as in Example 10 to obtain compound 32 in 40% yield. $^1$H NMR (400 MHz, CDCl$_3$) δ8.17 (s, 1H), 7.94 (d, J=8 Hz, 1H), 7.38 (m, 2H), 7.28 (m, 1H), 6.99 (m, 1H), 4.68 (t, J=8 Hz, 2H), 3.29 (m, 4H), 2.16 (m, 1H), 1.66 (m, 1H), 1.28 (m, 1H). LRMS (ESI) m/z 328 ([M+H]$^+$).

Example 33 Preparation of 6-(3-((2,2-difluorocyclopropyl)methyl)-[1,2,4]triazo[4,3-a]pyridin-7-yl)quinoline (Compound 33)

3-methylbenzeneboronic acid was replaced by quinoline-6-boronic acid, while the remaining starting materials, reagents and preparation methods were the same as in Example 10 to obtain compound 33 in 41% yield. $^1$H NMR (400 MHz, CDCl$_3$) δ8.97 (dd, J=4 Hz, J=4 Hz, 1H), 8.24 (m, 2H), 8.07 (m, 3H), 8.00 (dd, J=8 Hz, J=12 Hz, 1H), 7.48 (dd, J=8 Hz, J=8 Hz, 1H), 7.30 (m, 1H), 3.33 (m, 2H), 2.18 (m, 1H), 1.69 (m, 1H), 1.28 (m, 1H). LRMS (ESI) m/z 337 ([M+H]$^+$).

Example 34 Preparation of 8-(3-((2,2-difluorocyclopropyl)methyl)-[1,2,4]triazo[4,3-a]pyridin-7-yl)quinoline (Compound 34)

3-methylbenzeneboronic acid was replaced by quinoline-8-boronic acid, while the remaining starting materials, reagents and preparation methods were the same as in Example 10 to obtain compound 34 in 40% yield. $^1$H NMR (400 MHz, CDCl$_3$) δ8.93 (dd, J=8 Hz, J=4 Hz, 1H), 8.27 (dd, J=8 Hz, J=12 Hz, 1H), 8.06 (s, 1H), 8.02 (dd, J=4 Hz, 1H), 7.95 (dd, J=8 Hz, J=8 Hz, 1H), 7.85 (dd, J=8 Hz, J=4 Hz, 1H), 7.67 (m, 1H), 7.50 (dd, J=8 Hz, J=8 Hz, 1H), 7.45 (dd, J=4 Hz, J=8 Hz, 1H), 3.32 (m, 2H), 2.19 (m, 1H), 1.67 (m, 1H), 1.28 (m, 1H). LRMS (ESI) m/z 337 ([M+H]$^+$).

Example 35 Preparation of 7-(Benzo[d][1,3]dioxol-5-yl)-3-((2,2-difluorocyclopropyl)methyl)-[1,2,4]triazole[4,3-a]pyridine (Compound 35)

3-methylbenzeneboronic acid was replaced by benzo[d][1,3]dioxol-5-boronic acid, while the remaining starting materials, reagents and preparation methods were the same as in Example 10 to obtain compound 35 in 40% yield. $^1$H NMR (400 MHz, CDCl$_3$) δ8.01 (d, J=4 Hz, 1H), 7.92 (s, 1H), 7.19 (dd, J=8 Hz, J=8 Hz, 1H), 7.16 (dd, J=8 Hz, J=8 Hz, 1H), 7.11 (d, J=4 Hz, 1H), 6.93 (d, J=8 Hz, 1H), 6.06 (s, 2H), 3.30 (m, 2H), 2.19 (m, 1H), 1.69 (m, 1H), 1.28 (m, 1H). LRMS (ESI) m/z 330 ([M+H]$^+$).

Example 36 Preparation of 8-chloro-3-((2,2-difluorocyclopropyl)methyl)-7-(m-tolyl)-[1,2,4]triazole[4,3-a]pyridine (Compound 36)

2-fluoro-4-chloropyridine was replaced by 4-bromo-3-chloro-2-fluoropyridine, and 4-phenylpiperidine was replaced by 3-methylbenzeneboronic acid, N,N-diisopropylethylenediamine was replaced by sodium bicarbonate, and acetonitrile was replaced with 1,4-dioxane, and reacted in microwave at 150° C. for 90 minutes. The remaining starting materials, reagents and preparation methods were the same as in Example 1 to obtain compound 36 in 45% yield. $^1$H NMR (400 MHz, CDCl$_3$) δ8.02 (m, 1H), 7.42 (m, 1H), 7.35 (m, 2H), 7.30 (m, 1H), 6.98 (d, J=8 Hz, 1H), 3.35 (m, 2H), 2.46 (s, 3H), 2.17 (m, 1H), 1.68 (m, 1H), 1.30 (m, 1H). LRMS (ESI) m/z 333 ([M+H]$^+$).

Example 37 Preparation of 8-chloro-3-((2,2-difluorocyclopropyl)methyl)-7-(3-fluorophenyl)-[1,2,4]triazole[4,3-a]pyridine (Compound 37)

3-methylbenzeneboronic acid was replaced by 3-fluorobenzeneboronic acid, while the remaining starting materials, reagents and preparation methods were the same as in Example 36 to obtain compound 37 in 40% yield. $^1$H NMR (400 MHz, CDCl$_3$) δ8.02 (d, J=4 Hz, 1H), 7.55 (m, 2H), 7.23 (m, 2H), 6.97 (d, J=4 Hz, 1H), 3.35 (m, 2H), 2.17 (m, 1H), 1.70 (m, 1H), 1.32 (m, 1H). LRMS (ESI) m/z 338 ([M+H]$^+$).

Example 38 Preparation of 8-chloro-3-((2,2-difluorocyclopropyl)methyl)-7-(4-fluorophenyl)-[1,2,4]triazole[4,3-a]pyridine (Compound 38)

3-methylbenzeneboronic acid was replaced 4-fluorobenzeneboronic acid, while the remaining starting materials, reagents and preparation methods were the same as in Example 36 to obtain compound 38 in 41% yield. $^1$H NMR (400 MHz, CDCl$_3$) δ8.04 (d, J=8 Hz, 1H), 7.50 (m, 1H), 7.34 (d, J=8 Hz, 1H), 7.27 (d, J=8 Hz, 1H), 7.20 (m, 1H), 6.99 (d, J=8 Hz, 1H), 3.35 (m, 2H), 2.17 (m, 1H), 1.71 (m, 1H), 1.32 (m, 1H). LRMS (ESI) m/z 338 ([M+H]$^+$).

Example 39 Preparation of 4-(8-Chloro-3-((2,2-difluorocyclopropyl)methyl)-[1,2,4]triazole[4,3-a]pyridin-7-yl cyanobenzene (Compound 39)

3-methylbenzeneboronic acid was replaced by 4-cyanobenzeneboronic acid, while the remaining starting materials, reagents and preparation methods were the same as in Example 36 to obtain compound 39 in 34% yield. $^1$H NMR (400 MHz, CDCl$_3$) δ8.07 (d, J=8 Hz, 1H), 7.80 (d, J=4 Hz, 2H), 7.66 (d, J=8 Hz, 2H), 6.91 (d, J=8 Hz, 1H), 3.35 (m, 2H), 2.14 (m, 1H), 1.66 (m, 1H), 1.30 (m, 1H). LRMS (ESI) m/z 345 ([M+H]$^+$).

Example 40 Preparation of 2-(4-(8-Chloro-3-((2,2-difluorocyclopropyl)methyl)-[1,2,4]triazole[4,3-a]pyridine-7-yl)phenyl)isopropyl-2-ol (Compound 40)

The 3-methylbenzeneboronic acid was replaced by 4-(2-hydroxypropan-2-yl)-benzeneboronic acid, while the remaining starting materials, reagents and preparation methods were the same as in Example 36 to obtain compound 40 in 31% yield. $^1$H NMR (400 MHz, DMSO-d$_6$) δ8.51 (d, J=4 Hz, 1H), 7.63 (m, 2H), 7.52 (m, 2H), 7.08 (d, J=4 Hz, 1H), 5.13 (s, 1H), 3.32 (m, 2H), 2.28 (m, 1H), 1.48 (s, 6H), 1.38 (m, 1H). LRMS (ESI) m/z 378 ([M+H]$^+$).

Example 41 Preparation of 8-chloro-3-((2,2-difluorocyclopropyl)methyl)-7-(4-fluoro-2-methylphenyl)-[1,2,4]triazole[4,3-a]pyridine (Compound 41)

3-methylbenzeneboronic acid was replaced by 4-fluoro-2-methylbenzeneboronic acid, while the remaining starting materials, reagents and preparation methods were the same as in Example 36 to obtain compound 41 in 35% yield. $^1$H NMR (400 MHz, CDCl$_3$) δ8.01 (d, J=4 Hz, 1H), 7.19 (dd, J=4 Hz, J=4 Hz, 1H), 7.08 (d, J=8 Hz, 1H), 7.04 (m, 1H), 6.83 (d, J=4 Hz, 1H), 3.37 (m, 2H), 2.20 (m, 4H), 1.71 (m, 1H), 1.33 (m, 1H). LRMS (ESI) m/z 352 ([M+H]$^+$).

Example 42 Preparation of 8-chloro-3-((2,2-difluorocyclopropyl)methyl)-7-(4-fluoro-3-methylphenyl)-[1,2,4]triazole[4,3-a]pyridine (Compound 42)

3-methylbenzeneboronic acid was replaced by 4-fluoro-3-methylbenzeneboronic acid, while the remaining starting materials, reagents and preparation methods were the same as in Example 36 to obtain compound 42 in 36% yield. $^1$H NMR (400 MHz, CDCl$_3$) δ7.97 (d, J=4 Hz, 1H), 7.34 (m, 2H), 7.13 (t, J=8 Hz, 1H), 6.94 (d, J=4 Hz, 1H), 3.30 (m, 2H), 2.36 (s, 3H), 2.14 (m, 1H), 1.67 (m, 1H), 1.30 (m, 1H). LRMS (ESI) m/z 352 ([M+H]$^+$).

Example 43 Preparation of 8-chloro-3-((2,2-difluorocyclopropyl)methyl)-7-(4-fluoro-2-methoxyphenyl)-[1,2,4]triazole[4,3-a]pyridine (Compound 43)

3-methylbenzeneboronic acid was replaced by 4-fluoro-2-methoxybenzeneboronic acid, while the remaining starting materials, reagents and preparation methods were the same as in Example 36 to obtain compound 43 in 38% yield. $^1$H NMR (400 MHz, CDCl$_3$) δ7.80 (d, J=8 Hz, 1H), 7.26 (m, 1H), 6.86 (d, J=8 Hz, 1H), 6.77 (m, 2H), 3.80 (s, 3H), 3.30 (m, 2H), 2.14 (m, 1H), 1.67 (m, 1H), 1.28 (m, 1H). LRMS (ESI) m/z 368 ([M+H]$^+$).

Example 44 Preparation of 8-chloro-3-((2,2-difluorocyclopropyl)methyl)-7-(3-fluoro-4-methoxyphenyl)-[1,2,4]triazole[4,3-a]pyridine (Compound 44)

3-methylbenzeneboronic acid was replaced by 3-fluoro-4-methoxybenzeneboronic acid, while the remaining starting materials, reagents and preparation methods were the same as in Example 36 to obtain compound 44 in 37% yield. $^1$H NMR (400 MHz, CDCl$_3$) δ7.94 (d, J=8 Hz, 1H), 7.29 (m, 2H), 708 (t, J=10 Hz, 1H), 6.92 (d, J=8 Hz, 1H), 3.95 (s, 3H), 3.33 (m, 2H), 2.13 (m, 1H), 1.65 (m, 1H), 1.30 (m, 1H). LRMS (ESI) m/z 368 ([M+H]$^+$).

Example 45 Preparation of methyl 4-(8-chloro-3-((2,2-difluorocyclopropyl)methyl)-[1,2,4]triazole[4,3-a]pyridin-7-yl)-3-fluoro benzonate (Compound 45)

3-methylbenzeneboronic acid was replaced by 2-fluoro-4-methoxycarbonylbenzeneboronic acid, while the remaining starting materials, reagents and preparation methods were the same as in Example 36 to obtain compound 45 in 38% yield. $^1$H NMR (400 MHz, CDCl$_3$) δ8.02 (d, J=8 Hz, 1H), 7.98 (dd, J=4 Hz, J=8 Hz, 1H), 7.90 (dd, J=8 Hz, J=8 Hz, 1H), 7.48 (m, 1H), 6.92 (d, J=4 Hz, 1H), 3.99 (s, 3H), 3.35 (m, 2H), 2.17 (m, 1H), 1.69 (m, 1H), 1.31 (m, 1H). LRMS (ESI) m/z 396 (1M+H$^+$).

Example 46 Preparation of methyl 3-chloro-4-(8-chloro-3-((2,2-difluorocyclopropyl)methyl)-[1,2,4]triazole[4,3-a]pyridin-7-yl)benzonate (Compound 46)

3-methylbenzeneboronic acid was replaced by 2-chloro-4-methoxycarbonylbenzeneboronic acid, while the remaining starting materials, reagents and preparation methods were the same as in Example 36 to obtain compound 46 in 41% yield. $^1$H NMR (400 MHz, CDCl$_3$) δ8.21 (d, 1H), 8.05 (m, 2H), 7.46 (m, 1H), 6.85 (d, J=4 Hz, 1H), 3.97 (s, 3H), 3.37 (m, 2H), 2.17 (m, 1H), 1.67 (m, 1H), 1.30 (m, 1H). LRMS (ESI) m/z 412 ([M+H]$^+$).

Example 47 Preparation of 8-chloro-3-((2,2-difluorocyclopropyl)methyl)-7-(2,3-benzodihydrofuran-5-yl)-[1,2,4]triazole[4,3-a]pyridine (Compound 47)

3-methylbenzeneboronic acid was replaced by 2,3-dihydrobenzofuran-5-benzeneboronic acid, while the remaining starting materials, reagents and preparation methods were the same as in Example 36 to obtain compound 47 in 41% yield. $^1$H NMR (400 MHz, CDCl$_3$) δ7.94 (d, J=4 Hz, 1H), 7.41 (s, 1H), 7.30 (d, J=4 Hz, 1H), 6.97 (d, J=8 Hz, 1H), 6.91 (d, J=4 Hz, 1H), 4.68 (t, J=8 Hz, 2H), 3.33 (m, 4H), 2.14 (m, 1H), 1.69 (m, 1H), 1.30 (m, 1H). LRMS (ESI) m/z 362 ([M+H]$^+$).

Example 48 Preparation of 8-chloro-3-((2,2-difluorocyclopropyl)methyl)-7-(2,3-benzodihydrofuran-7-yl)-[1,2,4]triazole[4,3-a]pyridine (Compound 48)

3-methylbenzeneboronic acid was replaced by 2,3-dihydrobenzofuran-7-benzeneboronic acid, while the remaining starting materials, reagents and preparation methods were the same as in Example 36 to obtain compound 48 in 40% yield. $^1$H NMR (400 MHz, CDCl$_3$) δ7.93 (d, J=8 Hz, 1H), 7.32 (dd, J=4 Hz, J=8 Hz, 1H), 7.28 (d, J=8 Hz, 1H), 7.03 (d, J=4 Hz, 1H), 7.00 (t, J=6 Hz, 1H), 4.64 (t, J=8 Hz, 2H), 3.32 (m, 4H), 2.14 (m, 1H), 1.67 (m, 1H), 1.30 (m, 1H). LRMS (ESI) m/z 362 ([M+H]$^+$).

Example 49 Preparation of 8-(8-Chloro-3-((2,2-difluorocyclopropyl)methyl)-[1,2,4]triazo[4,3-a]pyridin-7-yl)quinoline (Compound 49)

3-methylbenzeneboronic acid was replaced by quinoline-8-boronic acid, while the remaining starting materials, reagents and preparation methods were the same as in Example 36 to obtain compound 49 in 35% yield. $^1$H NMR (400 MHz, CDCl$_3$) δ8.88 (dd, J=4 Hz, J=4 Hz, 1H), 8.27 (dd, J=8 Hz, J=8 Hz, 1H), 7.96 (m, 2H), 7.81 (dd, J=4 Hz, J=8 Hz, 1H), 7.68 (m, 1H), 7.47 (dd, J=8 Hz, J=8 Hz, 1H), 7.04 (d, J=4 Hz, 1H), 3.34 (m, 2H), 2.16 (m, 1H), 1.67 (m, 1H), 1.29 (m, 1H). LRMS (ESI) m/z 371 ([M+H]$^+$).

Example 50 Preparation of 8-(8-Chloro-3-((2,2-difluorocyclopropyl)methyl)-[1,2,4]triazo[4,3-a]pyridin-7-yl)quinoline (Compound 50)

3-methylbenzeneboronic acid was replaced by benzo[d][1,3]dioxol-5-boronic acid, while the remaining starting materials, reagents and preparation methods were the same as in Example 36 to obtain compound 50 in 38% yield. $^1$H NMR (400 MHz, CDCl$_3$) δ7.94 (d, J=8 Hz, 1H), 7.01 (d, J=8 Hz, 2H), 6.94 (d, J=8 Hz, 2H), 6.06 (s, 2H), 3.30 (m, 2H), 2.13 (m, 1H), 1.68 (m, 1H), 1.30 (m, 1H). LRMS (ESI) m/z 364 ([M+H]$^+$).

Example 51 Preparation of 3-((2,2-difluorocyclopropyl)methyl)-8-methyl-7-(m-tolyl)-[1,2,4]triazole[4,3-a]pyridine (Compound 51)

2-fluoro-4-chloropyridine was replaced by 2-fluoro-4-iodo-3-methylpyridine, and 4-phenylpiperidine was replaced by 3-methylbenzeneboronic acid, N,N-diisopropylethylenediamine was replaced by sodium bicarbonate, and acetonitrile was replaced with 1,4-dioxane, and reacted in microwave at 150° C. for 90 minutes. The remaining starting materials, reagents and preparation methods were the same as in Example 1 to obtain compound 51 in 38% yield. $^1$H NMR (400 MHz, CDCl$_3$) δ7.83 (d, J=8 Hz, 1H), 7.36 (m, 1H), 7.23 (d, J=8 Hz, 1H), 7.16 (d, J=8 Hz, 2H), 6.96 (d, J=8 Hz, 1H), 3.32 (m, 2H), 2.62 (s, 3H), 2.43 (s, 3H), 2.13 (m, 1H), 1.64 (m, 1H), 1.28 (m, 1H). LRMS (ESI) m/z 314 ([M+H]$^+$).

Example 52 Preparation of 3-((2,2-Difluorocyclopropyl)methyl)-8-methyl-7-(3-fluorophenyl)-[1,2,4]triazole[4,3-a]pyridine (Compound 52)

3-methylbenzeneboronic acid was replaced by 3-fluorobenzeneboronic acid, while the remaining starting materials, reagents and preparation methods were the same as in Example 51 to obtain compound 52 in 35% yield. $^1$H NMR (400 MHz, CDCl$_3$) δ7.86 (d, J=8 Hz, 1H), 7.46 (m, 1H), 7.09 (m, 3H), 6.85 (d, J=4 Hz, 1H), 3.32 (m, 2H), 2.63 (s, 3H), 2.14 (m, 1H), 1.64 (m, 1H), 1.28 (m, 1H). LRMS (ESI) m/z 318 ([M+H]$^+$).

Example 53 Preparation of 3-((2,2-Difluorocyclopropyl)methyl)-8-methyl-7-(4-fluorophenyl)-[1,2,4]triazole[4,3-a]pyridine (Compound 53)

3-methylbenzeneboronic acid was replaced 4-fluorobenzeneboronic acid, while the remaining starting materials, reagents and preparation methods were the same as in Example 51 to obtain compound 53 in 35% yield. $^1$H NMR (400 MHz, CDCl$_3$) δ7.86 (d, J=8 Hz, 1H), 7.35 (m, 2H), 7.18 (m, 2H), 6.86 (d, J=8 Hz, 1H), 3.27 (m, 2H), 2.63 (s, 3H), 2.14 (m, 1H), 1.67 (m, 1H), 1.28 (m, 1H). LRMS (ESI) m/z 318 ([M+H]$^+$).

Example 54 Preparation of 2-(4-(3-((2,2-difluorocyclopropyl)methyl)-8-methyl-[1,2,4]triazole[4,3-a]pyridin-7-yl)phenyl)propan-2-ol (Compound 54)

The 3-methylbenzeneboronic acid was replaced by 4-(2-hydroxypropan-2-yl)-benzeneboronic acid, while the remaining starting materials, reagents and preparation methods were the same as in Example 51 to obtain compound 54 in 33% yield. $^1$H NMR (400 MHz, DMSO-d$_6$) δ8.36 (d, J=8 Hz, 1H), 7.60 (d, J=8 Hz, 2H), 7.40 (d, J=8 Hz, 2H), 6.94 (d, J=8 Hz, 1H), 5.12 (s, 1H), 3.30 (m, 2H), 2.50 (s, 3H), 2.27 (m, 1H), 1.70 (m, 1H), 1.48 (s, 6H), 1.37 (m, 1H). LRMS (ESI) m/z 358 ([M+H]$^+$).

Example 55 Preparation of 3-((2,2-Difluorocyclopropyl)methyl)-7-(4-fluoro-2-methylphenyl)-8-methyl-[1,2,4]triazole[4,3-a]pyridine (Compound 55)

3-methylbenzeneboronic acid was replaced by 4-fluoro-2-methylbenzeneboronic acid, while the remaining starting materials, reagents and preparation methods were the same as in Example 51 to obtain compound 55 in 39% yield. $^1$H NMR (400 MHz, CDCl$_3$) δ7.83 (dd, J=8 Hz, J=8 Hz, 1H), 7.04 (m, 3H), 6.68 (d, J=8 Hz, 1H), 3.32 (m, 2H), 2.40 (s, 3H), 2.13 (m, 1H), 1.64 (m, 1H), 1.28 (m, 1H). LRMS (ESI) m/z 332 ([M+H]$^+$).

Example 56 Preparation of 3-((2,2-Difluorocyclopropyl)methyl)-7-(4-fluoro-3-methylphenyl)-8-methyl-[1,2,4]triazole[4,3-a]pyridine (Compound 56)

3-methylbenzeneboronic acid was replaced by 4-fluoro-3-methylbenzeneboronic acid, while the remaining starting materials, reagents and preparation methods were the same as in Example 51 to obtain compound 56 in 39% yield. $^1$H NMR (400 MHz, CDCl$_3$) δ7.83 (d, J=8 Hz, 1H), 7.13 (m, 3H), 6.82 (d, J=8 Hz, 1H), 3.32 (m, 2H), 2.60 (s, 3H), 2.34 (s, 3H), 2.12 (m, 1H), 1.64 (m, 1H), 1.25 (m, 1H). LRMS (ESI) m/z 332 ([M+H]$^+$).

Example 57 Preparation of 3-((2,2-Difluorocyclopropyl)methyl)-7-(3-fluoro-4-methoxyenyl)-8-methyl-[1,2,4]triazole[4,3-a]pyridine (Compound 57)

3-methylbenzeneboronic acid was replaced by 3-fluoro-4-methoxybenzeneboronic acid, while the remaining starting materials, reagents and preparation methods were the same as in Example 51 to obtain compound 57 in 37% yield. $^1$H NMR (400 MHz, CDCl$_3$) δ7.82 (m, 1H), 7.08 (m, 3H), 6.79 (m, 1H), 3.95 (s, 3H), 3.23 (m, 2H), 2.62 (s, 3H), 2.12 (m, 1H), 1.64 (m, 1H), 1.25 (m, 1H). LRMS (ESI) m/z 348 ([M+H]$^+$).

Example 58 Preparation of methyl 4-(3-((2,2-difluorocyclopropyl)methyl)-8-methyl-[1,2,4]triazole[4,3-a]pyridin-7-yl)-3-fluor obenzonate (Compound 58)

3-methylbenzeneboronic acid was replaced by 2-fluoro-4-methoxycarbonylbenzeneboronic acid, while the remaining starting materials, reagents and preparation methods were the same as in Example 51 to obtain compound 58 in 40% yield. $^1$H NMR (400 MHz, CDCl$_3$) δ7.93 (dd, J=4 Hz, J=8 Hz, 1H), 7.87 (m, 2H), 7.39 (t, J=8 Hz, 1H), 6.81 (d, J=8 Hz, 1H), 3.97 (s, 3H), 3.32 (m, 2H), 2.55 (s, 3H), 2.15 (m, 1H), 1.64 (m, 1H), 1.28 (m, 1H). LRMS (ESI) m/z 376 ([M+H]$^+$).

Example 59 Preparation of methyl 3-chloro-4-(3-((2,2-difluorocyclopropyl)methyl)-8-methyl-[1,2,4]triazole[4,3-a]pyridin-7-yl)benzonate (Compound 59)

3-methylbenzeneboronic acid was replaced by 2-chloro-4-methoxycarbonylbenzeneboronic acid, while the remaining starting materials, reagents and preparation methods were the same as in Example 51 to obtain compound 59 in 40% yield. $^1$H NMR (400 MHz, CDCl$_3$) δ8.17 (s, 1H), 8.00 (m, 1H), 7.87 (d, J=8 Hz, 1H), 7.34 (dd, J=4 Hz, J=8 Hz, 1H), 6.73 (d, J=8 Hz, 1H), 3.95 (s, 3H), 3.32 (m, 2H), 2.43 (s, 3H), 2.16 (m, 1H), 1.64 (m, 1H), 1.26 (m, 1H). LRMS (ESI) m/z 392 ([M+H]$^+$).

Example 60 Preparation of 3-((2,2-difluorocyclopropyl)methyl)-7-(2,3-benzodihydrofuran-5-yl)-8-methyl-[1,2,4]triazole[4,3-a]pyridine (Compound 60)

3-methylbenzeneboronic acid was replaced by 2,3-dihydrobenzofuran-5-benzeneboronic acid, while the remaining starting materials, reagents and preparation methods were the same as in Example 51 to obtain compound 60 in 37% yield. $^1$H NMR (400 MHz, CDCl$_3$) δ7.81 (d, J=8 Hz, 1H), 7.18 (s, 1H), 7.09 (dd, J=8 Hz, J=8 Hz, 1H), 8.84 (dd, J=8 Hz, J=8 Hz, 2H), 4.63 (t, J=8 Hz, 2H), 3.29 (m, 4H), 2.61 (s, 3H), 2.12 (m, 1H), 1.61 (m, 1H), 1.26 (m, 1H). LRMS (ESI) m/z 342 ([M+H]$^+$).

Example 61 Preparation of 7-(benzo[d][1,3]dioxol-5-yl)-3-((2,2-difluorocyclopropyl)methyl)-8-methyl-[1,2,4]triazole[4,3-a]pyridine (Compound 61)

3-methylbenzeneboronic acid was replaced by benzo[d][1,3]dioxol-5-boronic acid, while the remaining starting materials, reagents and preparation methods were the same as in Example 51 to obtain compound 61 in 38% yield. $^1$H NMR (400 MHz, CDCl$_3$) δ7.82 (d, J=4 Hz, 1H), 6.89 (m, 1H), 6.81 (m, 3H), 6.02 (s, 2H), 3.32 (m, 2H), 2.60 (s, 3H), 2.15 (m, 1H), 1.61 (m, 1H), 1.25 (m, 1H). LRMS (ESI) m/z 344 ([M+H]$^+$).

Example 62 Preparation of 3-((2,2-difluorocyclopropyl)methyl)-8-fluoro-7-(4-phenylpiperidin-1-yl)-[1,2,4]triazole[4,3-a]pyridine (Compound 62)

2-Fluoro-4-chloropyridine was replaced by 4-chloro-2,3-difluoropyridine, while the remaining starting materials, reagents and preparation methods were the same as in Example 1 to obtain compound 62 in 36% yield. $^1$H NMR (400 MHz, CDCl$_3$) δ8.21 (d, J=8 Hz, 1H), 7.27-7.30 (m, 5H), 6.90 (d, J=8 Hz, 1H), 3.00 (m, 4H), 2.78 (m, 1H), 2.50 (m, 2H), 1.80 (m, 4H), 1.14 (m, 1H), 0.40 (m, 2H). LRMS (ESI) m/z 387 ([M+H]$^+$).

Example 63 Preparation of 7-(4-(4-chlorophenyl)piperidin-1-yl)-3-((2,2-difluorocyclopropyl)methyl)-8-fluoro-[1,2,4]triazole[4,3-a]pyridine (compound 62)

4-phenylpyridine was replaced by 4-chlorophenylpiperidine, while the remaining raw materials, reagents and the preparation method was the same as in example 62 to give compound 63, yield 37%. (400 MHz, CDCl$_3$) δ8.21 (d, J=8 Hz, 1H), 7.41 (d, J=8 Hz, 2H), 7.24 (d, J=8 Hz, 2H), 6.90 (d, J=8 Hz, 1H), 3.00 (m, 4H), 2.78 (m, 1H), 2.50 (m, 2H), 1.80 (m, 4H), 1.14 (m, 1H), 0.40 (m, 2H). LRMS (ESI) m/z 421 ([M+]$^+$).

Example 64 Preparation of 4-(1-3-((2,2-difluorocyclopropyl)methyl)-8-fluoro-[1,2,4]triazole pyridine-7-yl)piperidin-4-yl)benzonitrile (Compound 64)

4-phenylpyridine was replaced by 4-(piperidin-4-yl)benzonitrile, while the remaining raw materials, reagents and the preparation method was the same as in example 62 to give compound 64, yield 33%. (400 MHz, CDCl$_3$) δ8.21 (d, J=8 Hz, 1H), 7.56 (d, J=8 Hz, 2H), 7.48 (d, J=8 Hz, 2H), 6.90 (d, J=8 Hz, 1H), 3.00 (m, 4H), 2.78 (m, 1H), 2.50 (m, 2H), 1.80 (m, 4H), 1.14 (m, 1H), 0.40 (m, 2H). LRMS (ESI) m/z 412 ([M+]$^+$).

Example 65 Preparation of 3-((2,2-Difluorocyclopropyl)methyl)-8-fluoro-7-(4-(2-(trifluoromethyl)phenyl)piperidin-1-yl)-[1,2,4]triazole[4,3-a]pyridine (Compound 65)

4-Phenylpiperidine was replaced with 4-(2-(trifluoromethyl)phenyl)piperidine, while the remaining starting materials, reagents and preparation methods were the same as in Example 62 to obtain compound 65 in 33% yield. (400 MHz, CDCl$_3$) δ8.21 (d, J=8 Hz, 1H), 7.54 (m, 1H), 7.37 (m, 1H), 7.23 (m, 1H), 7.20 (m, 1H), 6.90 (d, J=8 Hz, 1H), 3.00 (m, 4H), 2.78 (m, 1H), 2.50 (m, 2H), 1.80 (m, 4H), 1.14 (m, 1H), 0.40 (m, 2H). LRMS (ESI) m/z 455 ([M+]$^+$).

Example 66 Preparation of 3-((2,2-Difluorocyclopropyl)methyl)-8-fluoro-7-(4-(2-(trifluoromethyl)phenyl)piperidin-1-yl)-[1,2,4]triazole[4,3-a]pyridine (Compound 66)

4-phenylpyridine was replaced by 4-phenylpiperidin-4-ol, while the remaining raw materials, reagents and the preparation method was the same as in example 62 to give compound 66, yield 30%. (400 MHz, DMSO-d$_6$) δ8.21 (d, J=8 Hz, 1H), 7.54 (m, 2H), 7.38 (m, 3H), 6.90 (d, J=8 Hz, 1H), 3.65 (s, 1H), 3.00 (m, 4H), 2.50 (m, 2H), 1.80 (m, 4H), 1.14 (m, 1H), 0.40 (m, 2H). LRMS (ESI) m/z 403 ([M+]$^+$).

Example 67 Preparation of 3-((2,2-difluorocyclopropyl)methyl)-8-fluoro-7-(4-phenylpiperazin-1-yl)-[1,2,4]triazole[4,3-a]pyridine (Compound 67)

4-phenylpyridine was replaced by 4-phenylpiperazine, piperazine the remaining raw materials, reagents and the preparation method was the same as in example 62 to give compound 67, yield 30%. (400 MHz, CDCl$_3$) δ8.21 (d, J=8 Hz, 1H), 7.27 (d, J=8 Hz, 2H), 6.94 (d, J=8 Hz, 2H), 6.90 (d, J=8 Hz, 1H), 6.79 (m, 1H), 3.57 (m, 4H), 3.28 (m, 4H), 2.50 (m, 2H), 1.14 (m, 1H), 0.40 (m, 2H). LRMS (ESI) m/z 488 ([M+H]$^+$).

Example 68 Preparation of 3-((2,2-difluorocyclopropyl)methyl)-8-fluoro-7-(m-tolyl)-[1,2,4]triazole[4,3-a]pyridine (Compound 68)

2-fluoro-4-chloropyridine was replaced by 4-chloro-2,3-difluoropyridine, and 4-phenylpiperidine was replaced by 3-methylbenzeneboronic acid, N,N-diisopropylethylenediamine was replaced by sodium bicarbonate, and acetonitrile was replaced with 1,4-dioxane, and reacted in microwave at 150° C. for 90 minutes. The remaining starting materials, reagents and preparation methods were the same as in Example 1 to obtain compound 68 in 35% yield. (400 MHz, CDCl$_3$) δ8.42 (d, J=8 Hz, 1H), 7.79 (m, 1H), 7.73 (d, J=8 Hz, 1H), 7.36 (m, 2H), 7.19 (m, 1H), 2.50 (m, 2H), 2.34 (s, 3H), 1.14 (m, 1H), 0.40 (m, 2H). LRMS (ESI) m/z 318 ([M+H]$^+$).

Example 69 Preparation of 3-((2,2-Difluorocyclopropyl)methyl)-8-fluoro-7-(4-(trifluoromethyl)phenyl)-[1,2,4]triazole[4,3-a]pyridine (Compound 69)

3-methylbenzeneboronic acid was replaced by 4-trifluoromethylbenzeneboronic acid, while the remaining starting materials, reagents and preparation methods were the same as in example 68 to obtain compound 69 in 33% yield. (400 MHz, CDCl$_3$) δ8.42 (d, J=8 Hz, 1H), 7.73 (d, J=8 Hz, 1H), 7.68 (m, 2H), 7.38 (m, 2H), 2.50 (m, 2H), 1.14 (m, 1H), 0.40 (m, 2H). LRMS (ESI) m/z 372 ([M+H]$^+$).

Example 70 Preparation of 4-(3-((2,2-difluorocyclopropyl)methyl)-8-fluoro-[1,2,4]triazo[4,3-a]pyridin-7-yl)benzonitrile (Compound 70)

3-methylbenzeneboronic acid was replaced by 4-cyanobenzeneboronic acid, while the remaining starting materials, reagents and preparation methods were the same as in Example 68 to obtain compound 70 in 30% yield. (400 MHz, CDCl$_3$) δ8.42 (d, J=8 Hz, 1H), 7.84 (m, 2H), 7.82 (m, 2H), 7.73 (d, J=8 Hz, 1H), 2.50 (m, 2H), 1.14 (m, 1H), 0.40 (m, 2H). LRMS (ESI) m/z 329 ([M+H]$^+$).

Example 71 Preparation of 2-(4-(3-((2,2-difluorocyclopropyl)methyl)-8-fluoro-[1,2,4]triazole[4,3-a]pyridin-7-yl)phenyl)propan-2-ol (Compound 71)

The 3-methylbenzeneboronic acid was replaced by 4-(2-hydroxypropan-2-yl)-benzeneboronic acid, while the remaining starting materials, reagents and preparation methods were the same as in Example 68 to obtain compound 71 in 31% yield. (400 MHz, DMSO-d$_6$) δ8.42 (d, J=8 Hz, 1H), 7.73 (d, J=8 Hz, 1H), 7.42 (m, 2H), 7.38 (m, 2H), 2.50 (m, 2H), 1.14 (m, 1H), 0.40 (m, 2H). LRMS (ESI) m/z 362 ([M+H]$^+$).

Example 72 Preparation of 3-((2,2-Difluorocyclopropyl)methyl)-8-fluoro-7-(4-fluoro-2-methylphenyl)-[1,2,4]triazole[4,3-a]pyridine (Compound 72)

3-methylbenzeneboronic acid was replaced by 4-fluoro-2-methylbenzeneboronic acid, while the remaining materials, reagents and preparation methods were the same as in Example 68 to obtain compound 72 in 36% yield. (400 MHz, CDCl$_3$) δ8.42 (d, J=8 Hz, 1H), 7.73 (d, J=8 Hz, 1H), 7.65 (m, 1H), 7.11 (m, 1H), 6.83 (m, 1H), 2.59 (s, 3H), 2.50 (m, 2H), 1.14 (m, 1H), 0.40 (m, 2H). LRMS (ESI) m/z 336 ([M+H]$^+$).

Example 73 Preparation of methyl 4-(3-((2,2-Difluorocyclopropyl)methyl)-8-fluoro)-8-fluoro-[1,2,4]triazole[4,3-a]pyridin-7-yl) -3-fluorobenzoate (Compound 73)

3-methylbenzeneboronic acid was replaced by 2-fluoro-4-methylcarbonylbenzeneboronic acid, while the remaining starting materials, reagents and preparation methods were the same as in Example 68 to obtain compound 73 in 34% yield. (400 MHz, CDCl$_3$) δ8.42 (d, J=8 Hz, 1H), 7.73 (d, J=8 Hz, 1H), 7.88 (m, 1H), 7.71 (m, 1H), 7.69 (m, 1H), 3.89 (s, 3H), 2.50 (m, 2H), 1.14 (m, 1H), 0.40 (m, 2H). LRMS (ESI) m/z 380 ([M+H]$^+$).

Example 74 Preparation of 3-((2,2-difluorocyclopropyl)methyl)-7-(2,3-benzodihydrofuran-5-yl)-8-fluoro-[1,2,4]triazol e[4,3-a]pyridine (Compound 74)

3-methylbenzeneboronic acid was replaced by 2,3-benzodihydrofuran-5-boronic acid, while the remaining starting materials, reagents and preparation methods were the same as in Example 68 to obtain compound 74 in 32% yield. (400

MHz, CDCl$_3$) δ8.42 (d, J=8 Hz, 1H), 7.73 (m, 2H), 7.50 (m, 1H), 7.00 (m, 1H), 4.27 (m, 2H), 2.97 (m, 2H), 2.50 (m, 2H), 1.14 (m, 1H), 0.40 (m, 2H). LRMS (ESI) m/z 346 ([M+]$^+$).

Example 75 Preparation of 6-(3-((2,2-difluorocyclopropyl)methyl)-8-fluoro-[1,2,4]triazo[4,3-a]pyridin-7-yl)quinoline (Compound 75)

3-methylbenzeneboronic acid was replaced by quinoline-6-boronic acid, while the remaining starting materials, reagents and preparation methods were the same as in Example 68 to obtain compound 75 in 32% yield. (400 MHz, CDCl$_3$) δ8.83 (m, 1H), 8.42 (d, J=8 Hz, 1H), 8.38 (m, 1H), 8.21 (m, 1H), 8.04 (m, 1H), 7.90 (m, 1H), 7.73 (d, J=8 Hz, 1H), 7.58 (m, 1H), 2.50 (m, 2H), 1.14 (m, 1H), 0.40 (m, 2H). LRMS (ESI) m/z 355 ([M+]$^+$).

Example 76 Preparation of 7-(benzo[d][1,3]dioxol-5-yl)-3-((2,2-difluorocyclopropyl)methyl)-8-fluoro-[1,2,4]triazole[4,3-a]pyridine (Compound 76)

3-methylbenzeneboronic acid was replaced by benzo[d][1,3]dioxol-5-boronic acid, while the remaining starting materials, reagents and preparation methods were the same as in Example 68 to obtain compound 76 in 33% yield. (400 MHz, CDCl$_3$) δ8.42 (d, J=8 Hz, 1H), 7.73 (d, J=8 Hz, 1H), 7.24 (m, 1H), 6.94 (m, 2H), 6.07 (s, 2H), 2.50 (m, 2H), 1.14 (m, 1H), 0.40 (m, 2H). LRMS (ESI) m/z 348 ([M+]$^+$).

Example 77 Preparation of 8-bromo-3-((2,2-difluorocyclopropyl)methyl)-7-(4-(2-methylphenyl)piperidin-1-yl)-[1,2,4]triazole[4,3-a]pyridine (Compound 77)

2-Fluoro-4-chloropyridine was replaced by 3,4-dibromo-2-fluoropyridine, and 4-phenylpiperidine was replaced by 4-(2-tolyl)piperidine, while the remaining starting materials, reagents and preparation methods were the same as in Example 1 to obtain compound 77 in 31% yield. $^1$H NMR (400 MHz, CDCl$_3$) δ8.62 (d, J=8 Hz, 1H), 7.38 (m, 1H), 7.26 (d, J=8 Hz, 1H), 7.16 (m, 3H), 3.00 (m, 4H), 2.78 (m, 1H), 2.50 (m, 2H), 2.34 (s, 3H), 1.80 (m, 4H), 1.14 (m, 1H), 0.40 (m, 2H). LRMS (ESI) m/z 461 ([M+]$^+$).

Example 78 Preparation of 4-(1-(8-bromo-3-((2,2-difluorocyclopropyl)methyl)-[1,2,4]triazole[4,3-a]pyridine-7-yl)piperidin-4-yl)benzonitrile (Compound 78)

4-(2-Tolyl)piperidine was replaced by 4-(piperidin-4-yl)benzonitrile, while the remaining raw materials, reagents and the preparation method was the same as in example 77 to give compound 78, yield 30%. $^1$H NMR (400 MHz, CDCl$_3$) δ8.62 (d, J=8 Hz, 1H), 7.56 (m, 2H), 7.48 (m, 2H), 7.26 (d, J=8 Hz, 1H), 3.00 (m, 4H), 2.78 (m, 1H), 2.50 (m, 2H), 1.80 (m, 4H), 1.14 (m, 1H), 0.40 (m, 2H). LRMS (ESI) m/z 472 ([M+]$^+$).

Example 79 Preparation of 8-bromo-3-((2,2-difluorocyclopropyl)methyl)-7-(4-(2-trifluoromethylphenyl)piperidin-1-yl)-[1,2,4]triazole[4,3-a]pyridine (Compound 79)

4-(2-Methylphenyl)piperidine was replaced with 4-(2-trifluoromethylphenyl)piperidine, while the remaining starting materials, reagents and preparation methods were the same as in Example 77 to obtain compound 79 in 31% yield. $^1$H NMR (400 MHz, CDCl$_3$) δ8.62 (d, J=8 Hz, 1H), 7.54 (m, 1H), 7.37 (m, 1H), 7.26 (d, J=8 Hz, 1H), 7.22 (m, 2H), 3.00 (m, 4H), 2.78 (m, 1H), 2.50 (m, 2H), 1.80 (m, 4H), 1.14 (m, 1H), 0.40 (m, 2H). LRMS (ESI) m/z 515 ([M+H]$^+$).

Example 80 Preparation of 1-(8-bromine-3-((2,2-difluorocyclopropyl)methyl)-[1,2,4]triazole[4,3-a]pyridin-7-yl)-4-phenylpiperidin-4-ol (Compound 80)

4-(2-Methylphenyl)piperidine was replaced by 4-phenylpiperidin-4-ol, while the remaining raw materials, reagents and the preparation method was the same as in example 77 to give compound 80, yield 29%. (400 MHz, DMSO-d$_6$) δ8.62 (d, J=8 Hz, 1H), 7.54 (m, 2H), 7.38 (m, 3H), 7.26 (d, J=8 Hz, 1H), 3.65 (s, 1H), 3.00 (m, 4H), 2.50 (m, 2H), 1.80 (m, 4H), 1.14 (m, 1H), 0.40 (m, 2H). LRMS (ESI) m/z 463 ([M+]$^+$).

Example 81 Preparation of 8-bromo-7-(4-(2-chlorophenyl)piperazin-1-yl)-3-((2,2-difluorocyclopropyl)methyl)-[1,2,4]triazole[4,3-a]pyridine (Compound 81)

4-(2-Tolyl)piperidine was replaced by 4-(2-chlorophenyl)piperazine, while the remaining raw materials, reagents and the preparation method was the same as in example 77 to give compound 81, yield 28%. $^1$H NMR (400 MHz, CDCl$_3$) δ8.62 (d, J=8 Hz, 1H), 7.47 (m, 1H), 7.26 (d, J=8 Hz, 1H), 7.15 (m, 1H), 6.72 (m, 2H), 3.57 (m, 4H), 3.28 (m, 4H), 2.50 (m, 2H), 1.14 (m, 1H), 0.40 (m, 2H). LRMS (ESI) m/z 482 ([M+]$^+$).

Example 82 Preparation of 4-(8-bromo-3-((2,2-difluorocyclopropyl)methyl)-[1,2,4]triazo[4,3-a]pyridin-7-yl)benzonitrile (Compound 82)

2-fluoro-4-chloropyridine was replaced by 3,4-dibromo-2-fluoropyridine, and 4-phenylpiperidine was replaced by 4-cyanobenzeneboronic acid, N,N-diisopropylethylenediamine was replaced by sodium bicarbonate, and acetonitrile was replaced with 1,4-dioxane, and reacted in microwave at 150° C. for 90 minutes. The remaining starting materials, reagents and preparation methods were the same as in Example 1 to obtain compound 82 in 35% yield. (400 MHz, CDCl$_3$) δ8.83 (d, J=8 Hz, 1H), 8.09 (d, J=8 Hz, 1H), 7.83 (m, 4H), 2.50 (m, 2H), 1.14 (m, 1H), 0.40 (m, 2H). LRMS (ESI) m/z 389 ([M+H]$^-$).

Example 83 Preparation of 8-bromo-3-((2,2-difluorocyclopropyl)methyl)-7-(2-methyl-4-(trifluoromethyl)phenyl))-[1,2,4]triazole[4,3-a]pyridine (Compound 83)

4-cyanobenzeneboronic acid was replaced by 2-methyl-4-trifluoromethylbenzeneboronic acid, while the remaining starting materials, reagents and preparation methods were the same as in example 82 to obtain compound 83 in 36% yield. (400 MHz, CDCl$_3$) δ8.83 (d, J=8 Hz, 1H), 8.09 (d, J=8 Hz, 1H), 7.60 (m, 1H), 7.55 (m, 1H), 7.49 (m, 1H), 2.59 (s, 3H), 2.50 (m, 2H), 1.14 (m, 1H), 0.40 (m, 2H). LRMS (ESI) m/z 446 ([M+]$^+$).

Example 84 Preparation of 2-(4-(8-bromo-3-((2,2-difluorocyclopropyl)methyl)-[1,2,4]triazole[4,3-a]pyridin-7-yl)-3-fluorophenyl)propan-2-ol (Compound 84)

The 4-cyanobenzeneboronic acid was replaced by 2-fluoro-4-(2-hydroxypropan-2-yl)benzeneboronic acid, while the remaining starting materials, reagents and preparation methods were the same as in Example 82 to obtain compound 84 in 33% yield. (400 MHz, DMSO-$d_6$) δ8.83 (d, J=8 Hz, 1H), 8.09 (d, J=8 Hz, 1H), 7.70 (m, 1H), 7.19 (m, 1H), 6.96 (m, 1H), 3.65 (s, 1H), 2.50 (m, 2H), 1.30 (s, 6H), 1.14 (m, 1H), 0.40 (m, 2H). LRMS (ESI) m/z 440 ([M+]+).

Example 85 Preparation of methyl 4-(8-bromo-3-((2,2-difluorocyclopropyl)methyl)-[1,2,4]triazole[4,3-a]pyridin-7-yl)-3-chlorobenzonate (Compound 85)

4-cyanobenzeneboronic acid was replaced by 2-chloro-4-methoxycarbonylbenzeneboronic acid, while the remaining starting materials, reagents and preparation methods were the same as in Example 82 to obtain compound 85 in 36% yield. (400 MHz, CDCl$_3$) δ8.83 (d, J=8 Hz, 1H), 8.09 (d, J=8 Hz, 1H), 8.03 (m, 1H), 7.83 (m, 2H), 3.89 (s, 3H), 2.50 (m, 2H), 1.14 (m, 1H), 0.40 (m, 2H). LRMS (ESI) m/z 455 ([M+H]+).

Example 86 Preparation of 8-bromo-3-((2,2-difluorocyclopropyl)methyl)-7-(2,3-benzodihydrofuran-5-yl)-[1,2,4]triazole[4,3-a]pyridine (Compound 86)

4-cyanobenzeneboronic acid was replaced by 2,3-benzodihydrofuran-5-boronic acid, while the remaining starting materials, reagents and preparation methods were the same as in Example 82 to obtain compound 86 in 34% yield. (400 MHz, CDCl$_3$) δ8.83 (d, J=8 Hz, 1H), 8.09 (d, J=8 Hz, 1H), 7.74 (m, 1H), 7.50 (m, 1H), 7.00 (m, 1H), 4.27 (m, 2H), 2.97 (m, 2H), 2.50 (m, 2H), 1.14 (m, 1H), 0.40 (m, 2H). LRMS (ESI) m/z 406 ([M+]+).

Example 87 Preparation of 8-(8-bromo-3-((2,2-difluorocyclopropyl)methyl)-[1,2,4]triazo[4,3-a]pyridin-7-yl)quinoline (Compound 87)

4-cyanobenzeneboronic acid was replaced by quinoline-6-boronic acid, while the remaining starting materials, reagents and preparation methods were the same as in Example 82 to obtain compound 87 in 33% yield. (400 MHz, CDCl$_3$) δ8.83 (m, 2H), 8.38 (m, 1H), 8.21 (m, 1H), 8.05 (m, 2H), 7.90 (m, 1H), 7.58 (m, 1H), 2.50 (m, 2H), 1.14 (m, 1H), 0.40 (m, 2H). LRMS (ESI) m/z 415 ([M+H]+).

Example 88 Preparation of 7-(benzo[d][1,3]dioxol-5-yl)-8-bromo-3-((2,2-difluorocyclopropyl)methyl)-[1,2,4]triazole[4,3-a]pyridine (Compound 88)

4-cyanobenzeneboronic acid was replaced by benzo[d][1,3]dioxol-5-boronic acid, while the remaining starting materials, reagents and preparation methods were the same as in Example 82 to obtain compound 88 in 34% yield. (400 MHz, CDCl$_3$) δ8.83 (m, 2H), 8.38 (m, 1H), 8.21 (m, 1H), 8.05 (m, 2H), 7.90 (m, 1H), 7.58 (m, 1H), 2.50 (m, 2H), 1.14 (m, 1H), 0.40 (m, 2H). LRMS (ESI) m/z 408 ([M+H]+).

Example 89 Preparation of 3-((2,2-Difluorocyclopropyl)methyl)-7-(4-(2-(trifluoromethyl)phenyl)piperidin-1-yl)-[1,2,4]triazole[4,3-a]pyridine-8-carbonitrile (Compound 89)

2-fluoro-4-chloropyridine was replaced by 4-chloro-2-fluorocyanopyridine, and 4-phenylpiperidine was replaced by 4-(2-trifluoromethylphenyl)piperidine, while the remaining starting materials, reagents and preparation methods were the same as in Example 1 to obtain compound 89 in 36% yield. $^1$H NMR (400 MHz, CDCl$_3$) δ8.94 (d, J=8 Hz, 1H), 7.54 (m, 1H), 7.36 (m, 2H), 7.22 (m, 2H), 3.00 (m, 4H), 2.78 (m, 1H), 2.50 (m, 2H), 1.80 (m, 4H), 1.14 (m, 1H), 0.40 (m, 2H). LRMS (ESI) m/z 462 ([M+H]+).

Example 90 Preparation of 3-((2,2-difluorocyclopropyl)methyl)-7-(4-hydroxy-4-phenylpiperidin-1-yl)-[1,2,4]triazole[4,3-a]pyridine-8-carbonitrile (Compound 90)

4-(2-trifluoromethylphenyl)piperidine was replaced by 4-phenylpiperidin-4-ol, while the remaining raw materials, reagents and the preparation method was the same as in example 89 to give compound 90, yield 30%. $^1$H NMR (400 MHz, DMSO-$d_6$) δ8.94 (d, J=8 Hz, 1H), 7.54 (m, 2H), 7.37 (m, 4H), 3.65 (s, 1H), 3.00 (m, 4H), 2.50 (m, 2H), 1.80 (m, 4H), 1.14 (m, 1H), 0.40 (m, 2H). LRMS (ESI) m/z 410 ([M+H]+).

Example 91 Preparation of 7-(4-(2-chlorophenyl)piperazin-1-yl)-3-((2,2-difluorocyclopropyl)methyl)-[1,2,4]triazole[4,3-a]pyridine-8-carbonitrile (Compound 91)

4-(2-Trifluoromethylphenyl)piperidine was replaced by 4-(2-chlorophenyl)piperazine, while the remaining raw materials, reagents and the preparation method was the same as in example 89 to give compound 91, yield 30%. $^1$H NMR (400 MHz, CDCl$_3$) δ8.94 (d, J=8 Hz, 1H), 7.47 (m, 1H), 7.35 (d, J=8 Hz, 1H), 7.15 (m, 1H), 6.72 (m, 2H), 3.57 (m, 4H), 3.28 (m, 4H), 2.50 (m, 2H), 1.14 (m, 1H), 0.40 (m, 2H). LRMS (ESI) m/z 429 ([M+H]+).

Example 92 Preparation of 3-((2,2-Difluorocyclopropyl)methyl)-7-(3-fluorophenyl)-[1,2,4]triazole[4,3-a]pyridine-8-carbonitrile (Compound 92)

2-fluoro-4-chloropyridine was replaced by 4-chloro-2-fluorocyanopyridine, and 4-phenylpiperidine was replaced by 3-fluorobenzeneboronic acid, N,N-diisopropylethylenediamine was replaced by sodium bicarbonate, and acetonitrile was replaced with 1,4-dioxane, and reacted in microwave at 150° C. for 90 minutes. The remaining starting materials, reagents and preparation methods were the same as in Example 1 to obtain compound 92 in 37% yield. (400 MHz, CDCl$_3$) δ9.15 (d, J=8 Hz, 1H), 8.18 (d, J=8 Hz, 1H), 7.50 (m, 2H), 7.29 (m, 1H), 7.20 (m, 1H), 2.50 (m, 2H), 1.14 (m, 1H), 0.40 (m, 2H). LRMS (ESI) m/z 329 ([M+H]+).

Example 93 Preparation of 3-((2,2-Difluorocyclopropyl)methyl)-7-(4-(2-hydroxypropan-2-yl)phenyl)-[1,2,4]triazole[4,3-a]pyridine-8-carbonitrile (Compound 93)

The 3-fluorobenzeneboronic acid was replaced by 2-fluoro-4-(2-hydroxypropan-2-yl)benzeneboronic acid, while the remaining starting materials, reagents and preparation methods were the same as in Example 92 to obtain compound 93 in 37% yield. (400 MHz, DMSO-$d_6$) δ9.15 (d, J=8 Hz, 1H), 8.18 (d, J=8 Hz, 1H), 7.40 (m, 4H), 3.65 (s, 1H), 2.50 (m, 2H), 1.30 (s, 6H), 1.14 (m, 1H), 0.40 (m, 2H). LRMS (ESI) m/z 369 ([M+H]+).

Example 94 Preparation of 3-((2,2-difluorocyclopropyl)methyl)-7-(2,3-benzodihydrofuran-5-yl)-8-fluoro-[1,2,4]triazol e[4,3-a]pyridine-8-carbonitrile (Compound 94)

3-fluorobenzeneboronic acid was replaced by 2,3-benzodihydrofuran-5-boronic acid, while the remaining starting materials, reagents and preparation methods were the same as in Example 92 to obtain compound 94 in 35% yield. (400 MHz, CDCl$_3$) δ9.15 (d, J=8 Hz, 1H), 8.18 (d, J=8 Hz, 1H), 7.74 (m, 1H), 7.50 (m, 1H), 7.00 (m, 1H), 4.27 (m, 2H), 2.97 (m, 2H), 2.50 (m, 2H), 1.14 (m, 1H), 0.40 (m, 2H). LRMS (ESI) m/z 353 ([M+H]$^+$).

Example 95 Preparation of 3-((2,2-difluorocyclopropyl)methyl)-7-(quinolin-6-yl)-[1,2,4]triazole[4,3-a]pyridine-8-carbonitrile (Compound 95)

3-fluorobenzeneboronic acid was replaced by quinoline-6-boronic acid, while the remaining starting materials, reagents and preparation methods were the same as in Example 92 to obtain compound 95 in 31% yield. (400 MHz, CDCl$_3$) δ9.15 (d, J=8 Hz, 1H), 8.83 (m, 1H), 8.38 (m, 1H), 8.21 (m, 1H), 8.18 (d, J=8 Hz, 1H), 8.04 (m, 1H), 7.90 (m, 1H), 7.58 (m, 1H), 2.50 (m, 2H), 1.14 (m, 1H), 0.40 (m, 2H). LRMS (ESI) m/z 362 ([M+H]$^+$).

Example 96 Preparation of 7-(benzo[d][1,3]dioxol-5-yl)-3-((2,2-difluorocyclopropyl)methyl)-[1,2,4]triazole[4,3-a]pyridine-8-carbonitrile (Compound 96)

3-flurorbenzeneboronic acid was replaced by benzo[d][1,3]dioxol-5-boronic acid, while the remaining starting materials, reagents and preparation methods were the same as in Example 92 to obtain compound 96 in 32% yield. (400 MHz, CDCl$_3$) δ9.15 (d, J=8 Hz, 1H), 8.18 (d, J=8 Hz, 1H), 7.24 (m, 1H), 6.95 (m, 2H), 6.07 (s, 2H), 2.50 (m, 2H), 1.14 (m, 1H), 0.40 (m, 2H). LRMS (ESI) m/z 355 ([M+H]$^+$).

Example 97 Preparation of 3-((2,2-Difluorocyclopropyl)methyl)-7-(3-fluorophenyl)-8-(trifluoromethyl)-[1,2,4]triazole[ 4,3-a]pyridine (Compound 97)

2-fluoro-4-chloropyridine was replaced by 4-chloro-2-fluoro-3-trifluoromethylpyridine, and 4-phenylpiperidine was replaced by 3-fluorobenzeneboronic acid, N,N-diisopropylethylenediamine was replaced by sodium bicarbonate, and acetonitrile was replaced with 1,4-dioxane, and reacted in microwave at 150° C. for 90 minutes. The remaining starting materials, reagents and preparation methods were the same as in Example 1 to obtain compound 97 in 38% yield. (400 MHz, CDCl$_3$) δ8.40 (d, J=8 Hz, 1H), 7.75 (d, J=8 Hz, 1H), 7.50 (m, 2H), 7.29 (m, 1H), 7.20 (m, 1H), 2.50 (m, 2H), 1.14 (m, 1H), 0.40 (m, 2H). LRMS (ESI) m/z 372 ([M]$^+$).

Example 98 Preparation of 2-(4-(3-((2,2-difluorocyclopropyl)methyl)-8-(trifluoromethyl)-[1,2,4]triazole[4,3-a]pyridin-7-yl)phenyl)propan-2-ol (Compound 98)

The 3-fluorobenzeneboronic acid was replaced by 2-fluoro-4-(2-hydroxypropan-2-yl)benzeneboronic acid, while the remaining starting materials, reagents and preparation methods were the same as in Example 97 to obtain compound 98 in 34% yield. (400 MHz, DMSO-d$_6$) δ8.40 (d, J=8 Hz, 1H), 7.75 (d, J=8 Hz, 1H), 7.40 (m, 4H), 3.65 (s, 1H), 2.50 (m, 2H), 1.30 (s, 6H), 1.14 (m, 1H), 0.40 (m, 2H). LRMS (ESI) m/z 412 ([M+H]$^+$).

Example 99 Preparation of 3-((2,2-difluorocyclopropyl)methyl)-7-(3-fluoro-4-methoxyenyl)-8-(trifluoromethyl)-[1,2,4]triazole[4,3-a]pyridine (Compound 99)

3-fluorobenzeneboronic acid was replaced by 3-fluoro-4-methoxybenzeneboronic acid, while the remaining starting materials, reagents and preparation methods were the same as in Example 97 to obtain compound 99 in 36% yield. (400 MHz, CDCl$_3$) δ8.40 (d, J=8 Hz, 1H), 7.75 (d, J=8 Hz, 1H), 7.43 (m, 2H), 7.31 (m, 1H), 3.83 (s, 3H), 2.50 (m, 2H), 1.14 (m, 1H), 0.40 (m, 2H). LRMS (ESI) m/z 402 ([M+H]$^+$).

Example 100 Preparation of methyl 4-(3-((2,2-difluorocyclopropyl)methyl)-8-(trifluoromethyl)-[1,2,4]triazole[4,3-a]pyridin-7-yl)-3-fluorobenzonate (Compound 100)

3-fluorobenzeneboronic acid was replaced by 2-fluoro-4-methoxycarbonylbenzeneboronic acid, while the remaining starting materials, reagents and preparation methods were the same as in Example 97 to obtain compound 100 in 37% yield. (400 MHz, CDCl$_3$) δ8.40 (d, J=8 Hz, 1H), 7.88 (m, 1H), 7.75 (d, J=8 Hz, 1H), 7.70 (m, 2H), 3.89 (s, 3H), 2.50 (m, 2H), 1.14 (m, 1H), 0.40 (m, 2H). LRMS (ESI) m/z 430 ([M+H]$^+$).

Example 101 Preparation of 3-((2,2-difluorocyclopropyl)methyl)-7-(2,3-benzodihydrofuran-5-yl)-8-(trifluoromethyl)-[1,2,4]triazole[4,3-a]pyridine (Compound DC561501)

3-fluorobenzeneboronic acid was replaced by 2,3-benzodihydrofuran-5-boronic acid, while the remaining starting materials, reagents and preparation methods were the same as in Example 97 to obtain compound 101 in 37% yield. (400 MHz, CDCl$_3$) δ8.40 (d, J=8 Hz, 1H), 7.75 (m, 2H), 7.50 (m, 1H), 7.00 (m, 1H), 4.27 (m, 2H), 2.97 (m, 2H), 2.50 (m, 2H), 1.14 (m, 1H), 0.40 (m, 2H). LRMS (ESI) m/z 396 ([M+H]$^+$).

Example 102 Preparation of 6-(3-((2,2-difluorocyclopropyl)methyl)-8-(trifluoromethyl)-[1,2,4]triazo[4,3-a]pyridin-7-yl) quinoline (Compound 102)

3-fluorobenzeneboronic acid was replaced by quinoline-6-boronic acid, while the remaining starting materials, reagents and preparation methods were the same as in Example 97 to obtain compound 102 in 34% yield. (400 MHz, CDCl$_3$) δ8.83 (m, 1H), 8.40 (m, 2H), 8.21 (m, 1H), 8.04 (m, 1H), 7.90 (m, 1H), 7.75 (m, 1H), 7.58 (m, 1H), 2.50 (m, 2H), 1.14 (m, 1H), 0.40 (m, 2H). LRMS (ESI) m/z 405 ([M+H]$^+$).

Example 103 Preparation of 7-(benzo[d][1,3]dioxol-5-yl)-3-((2,2-difluorocyclopropyl)methyl)-8-(trifluoromethyl)-[1,2,4]triazole[4,3-a]pyridine (Compound 103)

3-flurorbenzeneboronic acid was replaced by benzo[d][1,3]dioxol-5-boronic acid, while the remaining starting materials, reagents and preparation methods were the same as in Example 97 to obtain compound 103 in 33% yield. (400 MHz, CDCl$_3$) δ8.40 (d, J=8 Hz, 1H), 7.75 (d, J=8 Hz, 1H), 7.24 (m, 1H), 6.95 (m, 2H), 6.07 (s, 2H), 2.50 (m, 2H), 1.14 (m, 1H), 0.40 (m, 2H). LRMS (ESI) m/z 398 ([M+H]$^+$).

Example 104 Preparation of 3-((2,2-difluorocyclopropyl)methyl)-7-(pyrimidin-2-yl)-8-(trifluoromethyl)-[1,2,4]triazole[4,3-a]pyridine (Compound 104)

3-fluorobenzeneboronic acid was replaced by pyrimidine-2-boronic acid, while the remaining starting materials, reagents and preparation methods were the same as in Example 97 to obtain compound 104 in 30% yield. (400 MHz, CDCl$_3$) δ9.08 (m, 2H), 8.40 (d, J=8 Hz, 1H), 7.75 (d, J=8 Hz, 1H), 7.67 (m, 1H), 2.50 (m, 2H), 1.14 (m, 1H), 0.40 (m, 2H). LRMS (ESI) m/z 356 ([M+H]$^+$).

Example 105 Preparation of 3-((2,2-difluorocyclopropyl)methyl)-7-(isoindoline-2-yl)-8-(trifluoromethyl)-[1,2,4]triazole [4,3-a]pyridine (Compound 105)

2-fluoro-4-chloropyridine was replaced by 4-chloro-2-fluoro-3-trifluoromethylpyridine, and 4-phenylpiperidine was replaced by iso-indoline, N,N-diisopropylethylenediamine was replaced by sodium bicarbonate, and acetonitrile was replaced with 1,4-dioxane, and reacted in microwave at 150° C. for 90 minutes. The remaining starting materials, reagents and preparation methods were the same as in Example 1 to obtain compound 105 in 33% yield. (400 MHz, CDCl$_3$) δ8.19 (d, J=8 Hz, 1H), 7.40 (m, 4H), 6.92 (d, J=8 Hz, 1H), 4.32 (s, 4H), 2.50 (m, 2H), 1.14 (m, 1H), 0.40 (m, 2H). LRMS (ESI) m/z 395 ([M+H]$^+$).

Example 106 Preparation of 3-((2,2-difluorocyclopropyl)methyl)-7-(isoindoline-2-yl)-8-(trifluoromethyl)-[1,2,4]triazole [4,3-a]pyridine (Compound 106)

The isoindoline was replaced with morpholine, while the remaining starting materials, reagents and preparation methods were the same as in Example 105 to obtain compound 106 in 31% yield. (400 MHz, CDCl$_3$) δ8.19 (d, J=8 Hz, 1H), 6.92 (d, J=8 Hz, 1H), 3.65 (t, 4H), 3.18 (t, 4H), 2.50 (m, 2H), 1.14 (m, 1H), 0.40 (m, 2H). LRMS (ESI) m/z 363 ([M+H]$^+$).

Pharmacological Activity Test Example

Example 107. Physical and Chemical Properties of the Compound

TABLE 1

Parameters of the physicochemical properties of the compounds

| Number of the compound | LogP | CLogP | tPSA |
|---|---|---|---|
| 1 | 4.4 | 3.71185 | 31.2 |
| 2 | 4.56 | 3.85485 | 31.2 |
| 3 | 4.96 | 4.42485 | 31.2 |
| 4 | 4.96 | 4.42485 | 31.2 |
| 5 | 5.32 | 4.59485 | 31.2 |
| 6 | 3.19 | 2.07485 | 51.43 |
| 7 | 3.35 | 2.21785 | 51.43 |
| 8 | 3.75 | 2.78785 | 51.43 |
| 9 | 4.67 | 3.47085 | 51.43 |
| 10 | 4.02 | 3.32524 | 27.96 |
| 11 | 3.69 | 2.96941 | 27.96 |
| 12 | 4.46 | 3.70954 | 27.96 |
| 13 | 3.69 | 2.96941 | 27.96 |
| 14 | 4.46 | 3.70954 | 27.96 |
| 15 | 3.57 | 2.25963 | 51.75 |

TABLE 1-continued

Parameters of the physicochemical properties of the compounds

| Number of the compound | LogP | CLogP | tPSA |
|---|---|---|---|
| 16 | 2.85 | 2.26568 | 45.03 |
| 17 | 3.36 | 2.79555 | 54.26 |
| 18 | 4.01 | 3.63355 | 54.26 |
| 19 | 3.41 | 2.74559 | 37.19 |
| 20 | 2.96 | 1.78824 | 48.19 |
| 21 | 3.5 | 2.49624 | 48.19 |
| 22 | 4.51 | 3.77424 | 27.96 |
| 23 | 3.57 | 2.82841 | 37.19 |
| 24 | 3.57 | 3.02841 | 37.19 |
| 25 | 3.57 | 2.46841 | 37.19 |
| 26 | 4.18 | 3.16841 | 27.96 |
| 27 | 4.18 | 3.46841 | 27.96 |
| 28 | 4.25 | 3.43247 | 27.96 |
| 29 | 3.51 | 2.93861 | 54.26 |
| 30 | 3.91 | 3.25861 | 54.26 |
| 31 | 3.39 | 2.88059 | 37.19 |
| 32 | 3.39 | 2.88059 | 37.19 |
| 33 | 3.62 | 2.71324 | 40.32 |
| 34 | 3.62 | 2.71324 | 40.32 |
| 35 | 3.32 | 2.79137 | 46.42 |
| 36 | 4.58 | 3.78999 | 27.96 |
| 37 | 4.25 | 3.43402 | 27.96 |
| 38 | 4.25 | 3.43402 | 27.96 |
| 39 | 4.13 | 2.72404 | 51.75 |
| 40 | 4.06 | 2.96099 | 48.19 |
| 41 | 4.74 | 3.63302 | 27.96 |
| 42 | 4.74 | 3.63302 | 27.96 |
| 43 | 4.13 | 2.93312 | 37.19 |
| 44 | 4.13 | 2.93312 | 37.19 |
| 45 | 4.07 | 3.40304 | 54.26 |
| 46 | 4.21 | 2.6070 | 64.93 |
| 47 | 3.95 | 3.34533 | 37.19 |
| 48 | 3.95 | 3.34533 | 37.19 |
| 49 | 4.18 | 3.17799 | 40.32 |
| 50 | 3.87 | 3.25611 | 46.42 |
| 51 | 4.51 | 3.52424 | 27.96 |
| 52 | 4.18 | 3.16841 | 27.96 |
| 53 | 4.18 | 3.16841 | 27.96 |
| 54 | 3.99 | 2.69524 | 48.19 |
| 55 | 4.67 | 3.36741 | 27.96 |
| 56 | 4.67 | 3.36741 | 27.96 |
| 57 | 4.06 | 3.02741 | 37.19 |
| 58 | 4 | 3.13761 | 54.26 |
| 59 | 4.4 | 3.45761 | 54.26 |
| 60 | 3.39 | 2.88059 | 37.19 |
| 61 | 3.8 | 2.99037 | 46.42 |
| 62 | 4.56 | 3.86353 | 31.2 |
| 63 | 5.11 | 4.57653 | 31.2 |
| 64 | 4.59 | 3.29653 | 54.99 |
| 65 | 5.48 | 4.57653 | 31.2 |
| 66 | 3.35 | 2.22653 | 51.43 |
| 67 | 4.14 | 3.06553 | 34.44 |
| 68 | 4.18 | 3.46999 | 27.96 |
| 69 | 4.62 | 3.85403 | 27.96 |
| 70 | 3.73 | 2.40404 | 51.75 |
| 71 | 3.66 | 2.64099 | 48.19 |
| 72 | 4.34 | 3.31302 | 27.96 |
| 73 | 3.67 | 3.08304 | 54.26 |
| 74 | 3.55 | 3.02533 | 37.19 |
| 75 | 3.78 | 2.85799 | 40.32 |
| 76 | 3.47 | 2.93611 | 46.42 |
| 77 | 5.71 | 5.03253 | 31.2 |
| 78 | 5.26 | 4.01653 | 54.99 |
| 79 | 6.15 | 5.46653 | 31.2 |
| 80 | 4.02 | 2.94653 | 51.43 |
| 81 | 5.36 | 4.66933 | 34.44 |
| 82 | 4.4 | 2.82404 | 51.75 |
| 83 | 5.77 | 4.47303 | 27.96 |
| 84 | 4.49 | 3.20402 | 48.19 |
| 85 | 4.74 | 3.82304 | 54.26 |
| 86 | 4.22 | 3.44533 | 37.19 |
| 87 | 4.45 | 3.27799 | 40.32 |
| 88 | 4.14 | 3.35611 | 46.42 |
| 89 | 5.35 | 4.09739 | 54.99 |
| 90 | 3.22 | 1.57739 | 75.22 |

TABLE 1-continued

Parameters of the physicochemical properties of the compounds

| Number of the compound | LogP | CLogP | tPSA |
|---|---|---|---|
| 91 | 4.57 | 3.30019 | 58.23 |
| 92 | 3.73 | 2.52024 | 51.75 |
| 93 | 3.53 | 2.04722 | 71.98 |
| 94 | 3.42 | 2.43184 | 60.98 |
| 95 | 3.65 | 2.26422 | 64.11 |
| 96 | 3.35 | 2.34244 | 70.21 |
| 97 | 4.62 | 3.90654 | 27.96 |
| 98 | 4.42 | 3.43352 | 48.19 |
| 99 | 4.49 | 3.7657 | 37.19 |
| 100 | 4.44 | 3.87557 | 54.26 |
| 101 | 4.31 | 3.81802 | 37.19 |
| 102 | 4.54 | 3.65052 | 40.32 |
| 103 | 4.24 | 3.7287 | 46.42 |
| 104 | 3.41 | 1.51971 | 52.68 |
| 105 | 4.25 | 3.32633 | 31.2 |
| 106 | 2.67 | 1.84333 | 40.43 |
| JNJ-40411813 | 2.89 | 4.86191 | 23.55 |

Note:
The physical and chemical properties of the compounds (LogP, CLogP and tPSA values) are estimates obtained from Chemdraw software in the ChemOffice package.
The results show that the physical and chemical properties of these compounds (LogP, CLogP and tPSA, etc.) are equivalent to the positive drug (JNJ-40411813; CAS number: 1127498-03-6), thus also possessing good druggability.

Example 108. In Vitro Activity Test for mGluR2

Experimental materials: HEK/mGluR2 cell line (human GluR2 transfected HEK cell line), DMEM (FBS) medium, positive control LY487379 (purchased from sigma; CAS: to 352317-17-1)

Experimental instrument: FLIPR Tetra real-time fluorescence imaging analysis system Experimental method: HDB Fluo-8 calcium fluorescence detection method Experimental principle: HDB Fluo-8 calcium ion fluorescence detection method is a fast, simple and reliable fluorescence detection method of intracellular calcium concentration changes. The Fluo 8-AM fluorescent dye is an acetyl methyl ester derivative of Fluo 8 which can easily penetrate into the cell membrane by culture. The fluorescent dye in the cell will be hydrolyzed by intracellular esterase, the resulting Fluo 8 as a polar molecule, cannot easily pass through the lipid bimolecular membrane, and will be retained in the cell, and combine with calcium ($Ca^{2+}$) to produce fluoresces.

Cells expressing GPCR receptor protein (mGluR2) were first calibrated with a calcium ion sensitive fluorescent probe and then stimulated with the compound. After stimulation, the receptor activates the calcium ion mobilization, and the fluorescent probe captures the calcium ion to induce the fluorescence signal. The signal can be read by a fluoroscopy plate. The fluorescent plate reader contains a sample addition for compound addition, thus enabling the change of the fluorescence value of the compound be read in real time. If the selected compound activates mGluR2, the calcium flow reaction can be greatly increased; conversely, if the selected compound is able to antagonize mGluR2, the calcium flow reaction can be greatly reduced. Experimental results indicate that the $EC_{50}$ for mGluR2 of the compounds 1 to 106 of the present invention are between 0.02 μM-10 μM, preferably between 0.02 μM-1 μm. Further, the experimental results show that the activities of the fluorine-containing triazolopyridine compound 1-106 according to the present invention to mGluR2 is about 8-15 times higher than that of the fluorine-free triazolopyridine compound corresponding to each compound. The representative experimental results are shown in the following table 2.

TABLE 2

Activating effects of compounds to mGluR2

| No. | mGluR2 $EC_{50}(\mu M)$ |
|---|---|
| 10 | 0.143 |
| 11 | 0.704 |
| 13 | 0.381 |
| 21 | 0.226 |
| 23 | 0.849 |
| 26 | 0.781 |
| 27 | 0.868 |
| 29 | 0.541 |
| 31 | 0.368 |
| 32 | 0.825 |
| 34 | 0.612 |
| 35 | 0.108 |
| 36 | 0.13 |
| 37 | 0.1902 |
| 41 | 0.856 |
| 44 | 0.118 |
| 45 | 0.0879 |
| 46 | 0.23 |
| 47 | 0.215 |
| 50 | 0.0623 |
| D35 | 0.97 |
| D45 | 0.91 |
| D50 | 0.89 |
| LY487379 | 0.23 |

Note:
LY487379 is a positive control, and the structures of the comparative compounds D35, D45, and D50 are as follows:

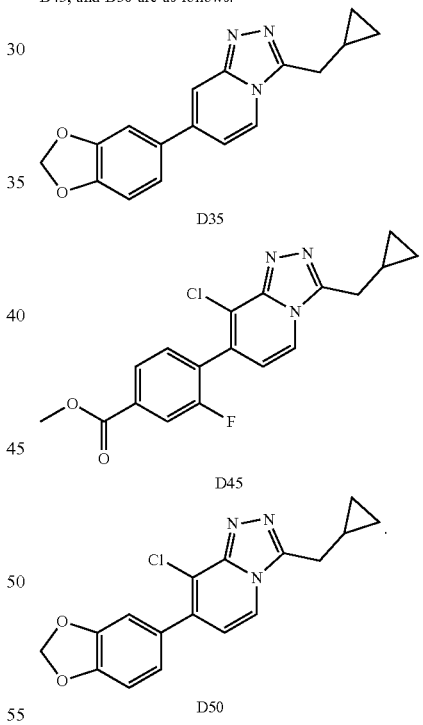

D35

D45

D50

Example 109. hERG Potassium Channel Toxicity Assay

Experimental method: hERG patch clamp detection method

Experimental procedure: Compound preparation: the stock solution of a compound was diluted with extracellular fluid, 2 μL of the compound stock solution was added to 998 μL extracellular fluid, and then serially diluted 5 times in an extracellular fluid containing 0.2% DMSO to obtain the final concentration to be tested. The highest test concentration of the compound was 40 μM, and there were 6 concentrations, 40, 8, 1.6, 0.32, 0.064, and 0.0128 μM, respectively.

The DMSO content in the final test concentration did not exceed 0.2%, and this concentration of DMSO did not affect the hERG potassium channel.

Experimental results:

TABLE 3

Effects of compounds on hERG potassium channel

| No. | Inhibition rate[a] (%) | IC$_{50}$ (μM) |
|---|---|---|
| 10 | 38.11 | >40 |
| 11 | 45.91 | >40 |
| 13 | 52.8 | 31.88 |
| 21 | 52.8 | 31.88 |
| 23 | 46.04 | >40 |
| 26 | 49.39 | >40 |
| 27 | 49.94 | >40 |
| 29 | 62.38 | 17.26 |
| 30 | — | — |
| 31 | 48.14 | >40 |
| 32 | 50.97 | >40 |
| 34 | 36 | >40 |
| 35 | 39.96 | >40 |
| 36 | 48.89 | >40 |
| 37 | 57.05 | 15.04 |
| 38 | — | — |
| 40 | — | — |
| 41 | 80.06 | 11.21 |
| 42 | — | — |
| 44 | 64.48 | 16.13 |
| 45 | 68.88 | 13.44 |
| 46 | 82.45 | 10.75 |
| 47 | 96.42 | 4.88 |
| 48 | — | — |
| 49 | — | — |
| 50 | 88.68 | 4.67 |
| Cisapride[b] | 96.58 | 0.13 |

[a]maximum concentration C$_{max}$ (40 μM) inhibition rate of test compounds;
[b]Cisapride (CAS: 81098-60-4) is a positive compound with a maximum test concentration of 3 μM and 6 concentrations in total, 3, 0.6, 0.12, 0.024, 0.0048, 0.00096 μM, respectively. IC$_{50}$ greater than 40 μM generally indicates no hERG inhibitory activity.

The experimental results show that the fluorine-containing triazolopyridines 1 to 106 according to the present invention have significantly lower toxicity than the positive control. When counted in IC$_{50}$, the safety of the compound 50 of the present invention is about 36 times of that of the positive control, and the safety of most of the compounds according to the present invention can be more than 300 times that of the positive control.

Experiment 110. Mouse Swimming Depression Test

Experiment objectives: to observe the effect of the test compound on the depressive status of mice Experimental animals: ICR mice, 20-28 g, both male and female Experimental equipment: plexiglass tube: cylindrical, 25 cm high, 15 cm inner diameter Sample treatment: The test compounds were ground with 1% CMC (sodium carboxymethyl cellulose) to prepare a homogeneous solution. In vivo dose was 5 mg/kg, 10 mg/kg and 20 mg/kg, the compound was orally administrated at 0.1 ml/10 g volume/body weight. Positive control drugs (amitriptyline and fluoxetine) were dissolved with 0.9% saline, in vivo dose was 10 mg/kg, intraperitoneal injected at 0.1 ml/10 g volume/body weight. (Note: mice were given the compound after fasted for 8 hours without water-fasted.)

Experimental principle: The mouse is placed in a limited space which can not escape to swim, thus inducing animals to non-movement state which reflects the animal's desperate behavior.

Experimental Methods: mice were grouped randomly, 15 minutes swimming depression was modeled at the first day, and equivalent mice were selected. The second day of the test, 1 hour after the animals were orally administered the compound (0.5 hours after intraperitoneal injection) and then the animals were put in water to record the non-movement time in the later 4 min of 6 min. The compound was tested whether it can significantly shorten the non-movement time of forced swimming mice, thus reflecting whether the tested compound has antidepressant effects.

Experimental Results:

| Group | Dose mg/kg | Number of animals | non-movement time (%) Mean ± SEM |
|---|---|---|---|
| Control | / | 10 | 100.00 ± 17.27 |
| Amitriptyline | 10 | 10 | 5.32 ± 2.08*** |
| Fluoxetine | 10 | 10 | 33.98 ± 9.84** |
| 45 | 5 | 10 | 63.99 ± 11.00 |
|  | 10 | 10 | 34.88 ± 6.57 |
|  | 20 | 10 | 56.29 ± 17.56 |
| 50 | 5 | 9 | 84.06 ± 10.65 |
|  | 10 | 10 | 52.10 ± 15.86 |
|  | 20 | 10 | 57.08 ± 17.80 |

Experimental Conclusion:

1. Positive control: Amitriptyline significantly improved the "no movement time" of mice swimming.

2. Tested compound: Compound 45 was able to effectively shorten the "no movement time" of swimming in mice, and Compound 45 showed a significant antidepressant effect.

Example 111. Mouse Open Field Experiment

Experiment objectives: to observe the anti-anxiety effect of the test compound on the mice by open field experiment.

Experimental animals: male C57BL/6 mice, 10 weeks old, purchased from Beijing Huafukang Biotechnology Co., Ltd.

Animal rearing: The temperature in the animal room was maintained at 20-25° C., the humidity was maintained at 40-70%, and the photoperiod was 12 hours light and 12 hours dark. During feeding, the mice were housed in standard mouse cages, with colored labels on each cage clearly indicating the item number, and the basic information such as the responsible person, group, animal number and animal gender. All animals were given free access to pure water and standard certified rodent feed. Before the start of the experiment, the experimental animals were adapted to the feeding environment for at least one week.

Dosage: Positive control, diazepam, intraperitoneally administrated, 0.5 mg/kg. The compound to be tested, intraperitoneally administered, 30 mg/kg.

Experimental principle: Based on the instincts of rodents tending to avoid light and fear of exploring open fields. When the experimental animals were first placed in the open field, the central area was a potential threat to the animals, while the peripheral area was relatively safe, and rats and mice were more likely to move along the perimeter of the field. Therefore, if the animal is of high anxiety level, it tends to stay in the peripheral area. Conversely, the number and time of exploration in the central area will increase.

Experimental grouping and administration: Experimental animals were randomly divided into 5 groups as follows:

| Group | Number of animals | Medicine | dosage (mg/Kg) | Frequency of administration | method of administration | Time point |
|---|---|---|---|---|---|---|
| 1 | 10 | Solvent | 10 | acute | i.p. | 1 hour before the field experiment |
| 2 | 10 | Diazepam | 0.5 | acute | i.p. | Half an hour before the field experiment |
| 3 | 10 | 35 | 30 | acute | i.p. | 1 hour before the field experiment |
| 4 | 10 | 45 | 30 | acute | i.p. | 1 hour before the field experiment |
| 5 | 10 | 50 | 30 | acute | i.p. | 1 hour before the field experiment |

Experimental method: after treated for one hour with the vehicle and the test compound or treated for 30 minutes with diazepam, the experimental animals are placed in the open field for detection. During the 30-minute test period, the total distance traveled by the experimental animals, the central area dwell time, and the percentage of the central area travel distance will be detected and recorded.

Experimental results:

| Group | Dose mg/kg | Number of animals | Total moving distance (cm) Mean ± SEM | Central area traveling distance percentage (%) Mean ± SEM | Central area dwell time (s) Mean ± SEM |
|---|---|---|---|---|---|
| Vehicle | 10 | 10 | 4745.8 ± 415.3 | 13.23 ± 1.47 | 74.7 ± 9.8 |
| Diazepam | 0.5 | 10 | 6391.6 ± 363.2 | 19.27 ± 0.97* | 158.4 ± 16.8 |
| DC561435 | 30 | 10 | 3491.2 ± 650.6 | 15.41 ± 1.99 | 102.6 ± 20.8 |
| DC561445 | 30 | 10 | 5043.2 ± 457.5 | 19.39 ± 1.63* | 110 ± 13.0 |
| DC561450 | 30 | 10 | 4407.2 ± 390.5 | 13.91 ± 0.96 | 81.1 ± 10.2 |

*$p < 0.05$, compared with the vehicle group. Data analysis was performed using one-way analysis of variance.

Experimental conclusion:
1. As a positive control drug, diazepam showed a very significant anti-anxiety effect in the open field experiment.
2. Compound 45 was able to significantly increase the central region's range of motion at a dosage of 30 mg/kg. Therefore, this compound can be used as an effective anti-anxiety drug.

All literatures mentioned in the present application are incorporated herein by reference, as though each one is individually incorporated by reference. Additionally, it should be understood that after reading the above teachings, those skilled in the art can make various changes and modifications to the present invention. These equivalents also fall within the scope defined by the appended claims.

The invention claimed is:

1. A fluorine-containing triazolopyridine represented by formula (I) and a racemate, R-stereoisomer, S-stereoisomer, pharmaceutically acceptable salt, or mixture thereof:

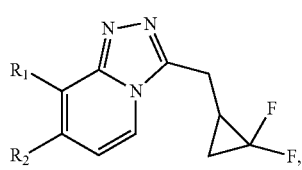

(I)

wherein:
$R_1$ is selected from the group consisting of a hydrogen, halogen, substituted or unsubstituted C1-C6 alkyl and cyano;

$R_2$ is select from the group consisting of a hydrogen, halogen, substituted or unsubstituted phenyl, substituted or unsubstituted heteroaryl, substituted or unsubstituted 3-7 membered heterocyclic group, substituted or unsubstituted 5-7 membered aryl-methylene and 3-7 membered heterocycle-methylene, wherein each of the heterocyclic groups independently contains 1 to 4 heteroatoms selected from oxygen, sulfur or nitrogen;

or the $R_2$ is selected from the group consisting of:

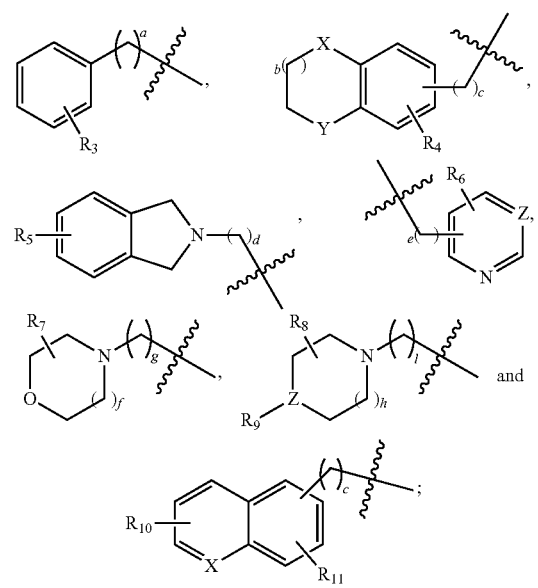

wherein $R_3$, $R_4$, $R_5$, $R_6$, $R_7$ and $R_8$ each independently represents 0-4 substituents on any position of the ring, and each substituent is selected from the group consisting of a halogen, substituted or unsubstituted C1-C6 alkyl, substituted or unsubstituted C1-C6 alkoxy, C1-C6 alkoxycarbonyl, cyano and hydroxy;

R$_9$ is selected from the group consisting of a hydrogen, halogen, substituted or unsubstituted C1-C6 alkyl, substituted or unsubstituted C2-C4 alkenyl, substituted or unsubstituted C2-C4 alkynyl, substituted or unsubstituted C3-C6 cycloalkyl, substituted or unsubstituted 3- to 9-membered heterocyclic group, substituted or unsubstituted aryl, substituted or unsubstituted heteroaryl;

R$_{10}$ and R$_{11}$ respectively represents 0-4 substituents on any position of the ring, and each R$_{10}$ and R$_{11}$ is independently selected from the group consisting of a halogen, substituted or unsubstituted C1-C6 alkyl, substituted or unsubstituted C1-C6 alkoxy, C1-C6 alkylcarbonyl, C1-C6 alkoxycarbonyl, cyano and hydroxy;

X, Y are each independently selected from CH$_2$, O, NH or S;

Z is selected from CH or N; and a, b, c, d, e, f, g, h and i are each independently selected from the group consisting of 0 and 1; wherein the X, Y and Z can be substituted by R$_3$, R$_4$, R$_5$, R$_6$, R$_7$, R$_8$, R$_9$, R$_{10}$ and R$_{11}$;

and the "substituted" means one or more hydrogen atoms of the group are substituted by substituents selected from the group consisting of a halogen, C1-C6 alkyl, halogen-substituted C1-C6 alkyl, hydroxy substituted C1-C6 alkyl, C1-C6 alkoxy, C1-C6 alkoxycarbonyl, halogen-substituted C1-C6 alkoxy, hydroxy-substituted C1-C6 alkoxy, cyano-substituted C1-C6 alkoxy, C2-C6 alkenyl, C2-C6 alkynyl, C3-C8 cycloalkyl, cyano, nitro, amino, hydroxy, carboxy, mercapto, sulfonyl, C6-C10 aryl, and 3-12 membered heterocyclic group; wherein the heterocyclic group each independently contain 1-4 heteroatoms selected from oxygen, sulfur or nitrogen;

provided that the compound of formula (I) is other than

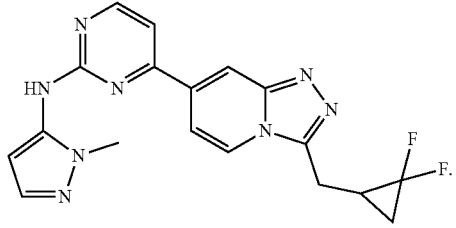 [SMILES: Cn1nccc1Nc1nccc(-c2ccn3c(CC4CC4(F)F)nnc3c2)n1]

2. The compound of claim 1, wherein R$_2$ is selected from the group consisting of a hydrogen, halogen, substituted or unsubstituted phenyl, substituted or unsubstituted heteroaryl, substituted or unsubstituted 3-7 membered heterocyclic group, substituted or unsubstituted 5-7 membered aryl-methylene and 3-7 membered heterocyclyl-methylene, while each heterocyclic group independently contains 1-4 heteroatoms selected from oxygen, sulfur or nitrogen.

3. The compound of claim 1, wherein the R$_1$ is selected from the group consisting of a hydrogen, halogen, CH$_3$, CN and CF$_3$.

4. The compound of claim 1, wherein the R$_2$ is selected from the group consisting of: a hydrogen, halogen, substituted or unsubstituted phenyl, substituted or unsubstituted heteroaryl, substituted or unsubstituted piperidinyl, and substituted or unsubstituted piperazinyl.

5. The compound of claim 1, wherein the R$_2$ is selected from the following group:

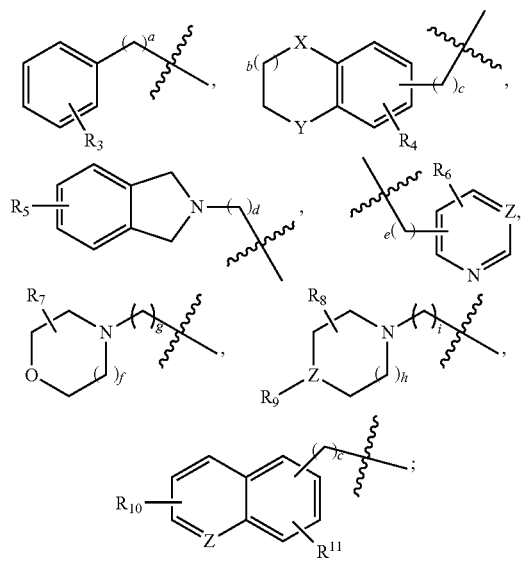

wherein the R$_3$, R$_4$, R$_5$, R$_6$, R$_7$ and R$_8$ each independently represents 0-4 substituents on any position of the ring, and each substituent is selected from the group consisting of a halogen, substituted or unsubstituted C1-C6 alkyl, substituted or unsubstituted C1-C6 alkoxy, C1-C6 alkoxycarbonyl, cyano and hydroxy; R$_9$ is selected from the group consisting of a hydrogen, halogen, substituted or unsubstituted C1-C6 alkyl, substituted or unsubstituted C2-C4 alkenyl, substituted or unsubstituted C2-C4 alkynyl, substituted or unsubstituted C3-C6 cycloalkyl, substituted or unsubstituted 3- to 9-membered heterocyclic group, substituted or unsubstituted aryl, substituted or unsubstituted heteroaryl; X, Y are each independently selected from CH$_2$, O, NH or S; Z is selected from CH or N; and a, b, c, d, e, f, g, h, and i are each independently selected from the group consisting of 0 and 1.

6. The compound of claim 1, wherein the compound is selected from the following group:

3-(2,2-difluorocyclopropyl)methyl)-7-(4-phenylpiperidin-1-yl)-[1,2,4]triazole[4,3-a]pyridine 3-(2,2-Difluorocyclopropyl)methyl)-7-(4-(4-fluorophenyl)piperidin-1-yl)-[1,2,4]triazole[4,3-a]pyridine 7-(4-(4-Chlorophenyl)piperidin-1-yl)-3-(2,2-difluorocyclopropyl)methyl)-[1,2,4]triazole[4,3-a]pyridine 7-(4-(3-Chlorophenyl)piperidin-1-yl)-3-(2,2-difluorocyclopropyl)methyl)-[1,2,4]triazole[4,3-a]pyridine 3-(2,2-Difluorocyclopropyl)methyl)-7-(4-(2-(trifluoromethyl)phenyl)piperidin-1-yl)-[1,2,4]triazole[4,3-a]pyridine 1-(3-(2,2-difluorocyclopropyl)methyl)-[1,2,4]triazole[4,3-a]pyridin-7-yl)-4-phenylpiperidin-4-ol 1-(3-(2,2-difluorocyclopropyl)methyl)-[1,2,4]triazole[4,3-a]pyridin-7-yl)-4-(4-fluorophenyl)piperidin-4-ol 4-(4-Chlorophenyl)-1-(3-((2,2-difluorocyclopropyl)methyl)-[1,2,4]triazole[4,3-a]pyridine-7-yl)piperidin-4-ol 4-(4-chloro-3-(trifluoromethyl)phenyl)-1-(3-(2,2-difluorocyclopropyl)methyl)-[1,2,4]triazole[4,3-a]pyridin-7-yl)piperidin-4-ol 3-(2,2-difluorocyclopropyl)methyl)-7-(m-tolyl)-[1,2,4]triazole[4,3-a]pyridine 3-(2,2-Difluorocyclopropyl)methyl)-7-(3-fluorophenyl)-[1,2,4]triazole[4,3-a]pyridine
3-(2,2-Difluorocyclopropyl)methyl)-7-(3-(trifluoromethyl)phenyl)-[1,2,4]triazole[4,3-a]pyridine
3-(2,2-difluorocyclopropyl)methyl)-7-(4-fluorophenyl)-[1,2,4]triazole[4,3-a]pyridine
3-(2,2-difluorocyclopropyl)methyl)-7-(4-(trifluoromethyl)phenyl)-[1,2,4]triazole[4,3-a]pyridine
4-(3-(2,2-difluorocyclopropyl)methyl)-[1,2,4]triazole[4,3-a]pyridin-7-yl)benzonitrile
1-(4-(3-((2,2-difluorocyclopropyl)methyl)-[1,2,4]triazole[4,3-a]pyridin-7-yl)phenyl)ethanone
methyl 4-(3-((2,2-difluorocyclopropyl)methyl)-[1,2,4]triazole[4,3-a]pyridin-7-yl)benzoate
isopropyl 4-(3-((2,2-difluorocyclopropyl)methyl)-[1,2,4]triazole[4,3-a]pyridin-7-yl)benzonate
3-(2,2-Difluorocyclopropyl)methyl)-7-(4-methoxyphenyl)-[1,2,4]triazole[4,3-a]pyridine
(4-(3-((2,2-difluorocyclopropyl)methyl)-[1,2,4]triazole[4,3-a]pyridin-7-yl)phenyl)methanol
2-(4-(3-((2,2-difluorocyclopropyl)methyl)-[1,2,4]triazole[4,3-a]pyridin-7-yl)phenyl)propan-2-ol
3-(2,2-difluorocyclopropyl)methyl)-7-(3,4-dimethylphenyl)-[1,2,4]triazole[4,3-a]pyridine
3-(2,2-difluorocyclopropyl)methyl)-7-(3-fluoro-4-methoxyphenyl)-[1,2,4]triazole[4,3-a]pyridine
3-(2,2-difluorocyclopropyl)methyl)-7-(2-fluoro-4-methoxyphenyl)-[1,2,4]triazole[4,3-a]pyridine
3-(2,2-difluorocyclopropyl)methyl)-7-(4-fluoro-2-methoxyphenyl)-[1,2,4]triazole[4,3-a]pyridine
3-(2,2-difluorocyclopropyl)methyl)-7-(4-fluoro-2-methylphenyl)-[1,2,4]triazole[4,3-a]pyridine
3-(2,2-difluorocyclopropyl)methyl)-7-(4-fluoro-3-methylphenyl)-[1,2,4]triazole[4,3-a]pyridine
7-(2-Chloro-4-fluorophenyl)-3-(2,2-difluorocyclopropyl)methyl)-[1,2,4]triazole[4,3-a]pyridine
Methyl 4-(3-((2,2-difluorocyclopropyl)methyl)-[1,2,4]triazolo[4,3-a]pyridin-7-yl)-3-fluorobenzoate
Methyl 3-Chloro-4-(3-((2,2-difluorocyclopropyl)methyl)-[1,2,4]triazole[4,3-a]pyridin-7-yl)benzonate
3-(2,2-difluorocyclopropyl)methyl)-7-(2,3-benzodihydrofuran-5-yl)-[1,2,4]triazole[4,3-a]pyridine
3-(2,2-difluorocyclopropyl)methyl)-7-(2,3-benzodihydrofuran-7-yl)-[1,2,4]triazole[4,3-a]pyridine
6-(3-(2,2-difluorocyclopropyl)methyl)-[1,2,4]triazole[4,3-a]pyridin-7-yl)quinoline
8-(3-(2,2-difluorocyclopropyl)methyl)-[1,2,4]triazole[4,3-a]pyridin-7-yl)quinoline
7-(Benzo[d][1,3]dioxol-5-yl)-3-(2,2-difluorocyclopropyl)methyl)-[1,2,4]triazole[4,3-a]pyridine
8-chloro-3-(2,2-difluorocyclopropyl)methyl)-7-(m-tolyl)-[1,2,4]triazole[4,3-a]pyridine
8-chloro-3-(2,2-difluorocyclopropyl)methyl)-7-(3-fluorophenyl)-[1,2,4]triazole[4,3-a]pyridine
8-chloro-3-(2,2-difluorocyclopropyl)methyl)-7-(4-fluorophenyl)-[1,2,4]triazole[4,3-a]pyridine
4-(8-chloro-3-((2,2-difluorocyclopropyl)methyl)-[1,2,4]triazole[4,3-a]pyridin-7-yl)cyanobenzene
2-(4-(8-chloro-3-(2,2-difluorocyclopropyl)methyl)-[1,2,4]triazole[4,3-a]pyridine-7-yl)phenyl)isopropyl-2-ol
8-chloro-3-(2,2-difluorocyclopropyl)methyl)-7-(4-fluoro-2-methylphenyl)-[1,2,4]triazole[4,3-a]pyridine
8-chloro-3-(2,2-difluorocyclopropyl)methyl)-7-(4-fluoro-3-methylphenyl)-[1,2,4]triazole[4,3-a]pyridine
8-chloro-3-(2,2-difluorocyclopropyl)methyl)-7-(4-fluoro-2-methoxyphenyl)-[1,2,4]triazole[4,3-a]pyridine
8-chloro-3-(2,2-difluorocyclopropyl)methyl)-7-(3-fluoro-4-methoxyphenyl)-[1,2,4]triazole[4,3-a]pyridine
Methyl 4-(8-Chloro-3-((2,2-difluorocyclopropyl)methyl)-[1,2,4]triazole[4,3-a]pyridin-7-yl)-3-fluorobenzoate
Methyl 3-Chloro-4-(8-chloro-3-((2,2-difluorocyclopropyl)methyl)-[1,2,4]triazole[4,3-a]pyridine-7-yl)benzoate
8-chloro-3-((2,2-difluorocyclopropyl)methyl)-7-(2,3-benzodihydrofuran-5-yl)-[1,2,4]triazole[4,3-a]pyridine
8-chloro-3-((2,2-difluorocyclopropyl)methyl)-7-(2,3-benzodihydrofuran-7-yl)-[1,2,4]triazole[4,3-a]pyridine
8-(8-chloro-3-((2,2-difluorocyclopropyl)methyl)-[1,2,4]triazole[4,3-a]pyridin-7-yl)quinoline
7-(Benzo[d][1,3]dioxol-5-yl)-8-chloro-3-((2,2-difluorocyclopropyl)methyl)-[1,2,4]triazole[4,3-a]pyridine
3-(2,2-difluorocyclopropyl)methyl)-8-methyl-7-(m-tolyl)-[1,2,4]triazole[4,3-a]pyridine
3-((2,2-difluorocyclopropyl)methyl)-8-methyl-7-(3-fluorophenyl)-[1,2,4]triazole[4,3-a]pyridine
3-(2,2-difluorocyclopropyl)methyl)-8-methyl-7-(4-fluorophenyl)-[1,2,4]triazole[4,3-a]pyridine
2-(4-(3-((2,2-difluorocyclopropyl)methyl)-8-methyl-[1,2,4]triazole[4,3-a]pyridine-7-yl)phenyl)propan-2-ol
3-(2,2-difluorocyclopropyl)methyl)-7-(4-fluoro-2-methylphenyl)-8-methyl-[1,2,4]triazole[4,3-a]pyridine
3-(2,2-difluorocyclopropyl)methyl)-7-(4-fluoro-3-methylphenyl)-8-methyl-[1,2,4]triazole[4,3-a]pyridine
3-(2,2-difluorocyclopropyl)methyl)-7-(3-fluoro-4-methoxyphenyl)-8-methyl-[1,2,4]triazole[4,3-a]pyridine
Methyl 4-(3-((2,2-Difluorocyclopropyl)methyl)-8-methyl-[1,2,4]triazole[4,3-a]pyridin-7-yl)-3-fluorobenzoate
methyl 3-Chloro-4-(3-((2,2-difluorocyclopropyl)methyl))-8-methyl-[1,2,4]triazole[4,3-a]pyridin-7-yl)-benzonate
3-(2,2-difluorocyclopropyl)methyl)-7-(2,3-benzodihydrofuran-5-yl)-8-methyl-[1,2,4]triazole[4,3-a]pyridine
7-(Benzo[d][1,3]dioxol-5-yl)-3-((2,2-difluorocyclopropyl)methyl)-8-methyl-[1,2,4]triazole[4,3-a]pyridine
3-(2,2-difluorocyclopropyl)methyl)-8-fluoro-7-(4-phenylpiperidin-1-yl)-[1,2,4]triazole[4,3-a]pyridine
7-(4-(4-Chlorophenyl)piperidin-1-yl)-3-(2,2-difluorocyclopropyl)methyl)-8-fluoro-[1,2,4]triazole[4,3-a]pyridine
4-(1-(3-((2,2-difluorocyclopropyl)methyl)-8-fluoro-[1,2,4]triazole[4,3-a]pyridin-7-yl)piperidin-4-yl)benzonitrile
3-(2,2-difluorocyclopropyl)methyl)-8-fluoro-7-(4-(2-(trifluoromethyl)phenyl)piperidin-1-yl)-[1,2,4]triazole[4,3-a]pyridine
1-(3-((2,2-difluorocyclopropyl)methyl)-8-fluoro-[1,2,4]triazole[4,3-a]pyridin-7-yl)-4-phenylpiperidine-4-ol
3-(2,2-difluorocyclopropyl)methyl)-8-fluoro-7-(4-phenylpiperazin-1-yl)-[1,2,4]triazole[4,3-a]pyridine
3-(2,2-difluorocyclopropyl)methyl)-8-fluoro-7-(m-tolyl)-[1,2,4]triazole[4,3-a]pyridine
3-(2,2-difluorocyclopropyl)methyl)-8-fluoro-7-(4-(trifluoromethyl)phenyl)-[1,2,4]triazole[4,3-a]pyridine
4-(3-((2,2-difluorocyclopropyl)methyl)-8-fluoro-[1,2,4]triazole[4,3-a]pyridin-7-yl)benzonitrile
2-(4-(3-(2,2-difluorocyclopropyl)methyl)-8-fluoro-[1,2,4]triazole[4,3-a]pyridine-7-yl)phenyl)propan-2-ol
3-(2,2-difluorocyclopropyl)methyl)-8-fluoro-7-(4-fluoro-2-methylphenyl)-[1,2,4]triazole[4,3-a]pyridine Methyl 4-(3-((2,2-difluorocyclopropyl)methyl)-8-fluoro)-8-fluoro-[1,2,4]triazole[4,3-a]pyridin-7-yl)-3-fluorobenzonate 3-(2,2-difluorocyclopropyl)methyl)-7-(2,3-benzodihydrofuran-5-yl)-8-fluoro-[1,2,4]triazole[4,3-a]pyridine 6-(3-((2,2-difluorocyclopropyl)methyl)-8-fluoro-[1,2,4]triazole[4,3-a]pyridine-7-yl)quinoline 7-(Benzo[d][1,3]dioxole-5-yl)-3-((2,2-difluorocyclopropyl)methyl)-8-fluoro-[1,2,4]triazolo[4,3-a]pyridine 8-bromo-3-(2,2-difluorocyclopropyl)methyl)-7-(4-(2-methylphenyl)piperidin-1-yl)-[1,2,4]triazolo[4,3-a]pyridine 4-(1-(8-bromo-3-((2,2-difluorocyclopropyl)methyl))-[1,2,4]triazole[4,3-a]pyridine-7-yl)piperidin-4-yl)benzonitrile 8-Bromo-3-((2,2-difluorocyclopropyl)methyl)-7-(4-(2-(trifluoromethylphenyl)piperidin-1-yl)-[1,2,4]triazolo[4,3-a]pyridine 1-(8-Bromo-3-((2,2-difluorocyclopropyl)methyl)-[1,2,4]triazolo[4,3-a]pyridin-7-yl)-4-phenylpiperidin-4-ol 8-bromo-7-(4-(2-chlorophenyl)piperazin-1-yl)-3-((2,2-difluorocyclopropyl)methyl)-[1,2,4]triazolo[4,3-a]pyridine 4-(8-Bromo-3-((2,2-difluorocyclopropyl)methyl)-[1,2,4]triazole[4,3-a]pyridine-7-benzonitrile 8-Bromo-3-((2,2-difluorocyclopropyl)methyl)-7-(2-methyl-4-(trifluoromethyl)phenyl)-[1,2,4]triazole[4,3-a]pyridine 2-(4-(8-bromo-3-((2,2-difluorocyclopropyl)methyl)-[1,2,4]triazole[4,3-a]pyridin-7-yl)-3-fluorophenyl)propan-2-ol Methyl 4-(8-Bromo-3-((2,2-difluorocyclopropyl)methyl)-[1,2,4]triazole[4,3-a]pyridine-7-yl)-3-chlorobenzoate 8-Bromo-3-((2,2-difluorocyclopropyl)methyl)-7-(2,3-benzodihydrofuran-5-yl)-[1,2,4]triazole[4,3-a]pyridine 6-(8-Bromo-3-(2,2-difluorocyclopropyl)methyl)-[1,2,4]triazole[4,3-a]pyridine-7-quinoline 7-(Benzo[d][1,3]dioxole-5-yl)-8-bromo-3-((2,2-difluorocyclopropyl)methyl)-[1,2,4]triazole[4,3-a]pyridine 3-(2,2-difluorocyclopropyl)methyl)-7-(4-(2-(trifluoromethyl)phenyl)piperidin-1-yl)-[1,2,4]triazole[4,3-a]pyridine-8-carbonitrile 3-((2,2-difluorocyclopropyl)methyl)-7-(4-hydroxy-4-phenylpiperidin-1-yl)-[1,2,4]triazole[4,3-a]pyridine-8-carbonitrile 7-(4-(2-Chlorophenyl)piperazin-1-yl)-3-((2,2-difluorocyclopropyl)methyl)-[1,2,4]triazole[4,3-a]pyridine-8-carbonitrile 3-(2,2-difluorocyclopropyl)methyl)-7-(3-fluorophenyl)-[1,2,4]triazole[4,3-a]pyridine-8-carbonitrile 3-(2,2-difluorocyclopropyl)methyl)-7-(4-(2-hydroxypropan-2-yl)phenyl)-[1,2,4]triazole[4,3-a]pyridine-8-carbonitrile 3-((2,2-difluorocyclopropyl)methyl)-7-(2,3-benzodihydrofuran-5-yl)-[1,2,4]triazole[4,3-a]pyridine-8-carbonitrile 3-(2,2-difluorocyclopropyl)methyl)-7-(quinolin-6-yl)-[1,2,4]triazole[4,3-a]pyridine-8-carbonitrile 7-(Benzo[d][1,3]dioxole-5-yl)-3-((2,2-difluorocyclopropyl)methyl)-[1,2,4]triazole[4,3-a]pyridine-8-carbonitrile 3-(2,2-difluorocyclopropyl)methyl)-7-(3-fluorophenyl)-8-(trifluoromethyl)-[1,2,4]triazole[4,3-a]pyridine 2-(4-(3-((2,2-difluorocyclopropyl)methyl)-8-(trifluoromethyl)-[1,2,4]triazole[4,3-a]pyridine-7-yl)phenyl)propan-2-ol 3-(2,2-difluorocyclopropyl)methyl)-7-(3-fluoro-4-methoxyphenyl)-8-(trifluoromethyl)-[1,2,4]triazole[4,3-a]pyridine Methyl 4-(3-((2,2-difluorocyclopropyl)methyl)-8-(trifluoromethyl)-[1,2,4]triazole[4,3-a]pyridin-7-yl)-3-fluorobenzonate 3-(2,2-difluorocyclopropyl)methyl)-7-(2,3-benzodihydrofuran-5-yl)-8-(trifluoromethyl)-[1,2,4]triazole[4,3-a]pyridine 6-(3-(2,2-difluorocyclopropyl)methyl)-8-(trifluoromethyl)-[1,2,4]triazole[4,3-a]pyridin-7-yl)quinoline 7-(Benzo[d][1,3]dioxol-5-yl)-3-(2,2-difluorocyclopropyl)methyl)-8-(trifluoromethyl)-[1,2,4]triazole[4,3-a]pyridine 3-(2,2-difluorocyclopropyl)methyl)-7-(pyrimidin-2-yl)-8-(trifluoromethyl)-[1,2,4]triazole[4,3-a]pyridine 3-(2,2-difluorocyclopropyl)methyl)-7-(isoindoline-2-yl)-8-(trifluoromethyl)-[1,2,4]triazole[4,3-a]pyridine; and 4-(3-(2,2-difluorocyclopropyl)methyl)-8-(trifluoromethyl)-[1,2,4]triazole[4,3-a]pyridin-7-yl)morpholine.

7. A pharmaceutical composition, wherein the pharmaceutical composition comprises: (a) a therapeutically effective amount of a compound of the claim 1 of the invention, or a pharmaceutically acceptable salt, racemate, R-isomer, S-isomer thereof, or combination thereof, and (b) pharmaceutically acceptable carriers.

8. A method for treating diseases associated with mGLuR2, comprising administering to a subject in need thereof a compound of claim 1, or a racemate, R-isomer, S-isomer, pharmaceutically acceptable salt, or mixture thereof; and the disease is anxiety and/or depression.

9. The compound of claim 5, wherein the substituted or unsubstituted C1-C6 alkyl is halogen-substituted C1-C6 alkyl or hydroxy-substituted C1-C6 alkyl.

* * * * *